US008748351B2

(12) United States Patent
Kunert et al.

(10) Patent No.: US 8,748,351 B2
(45) Date of Patent: Jun. 10, 2014

(54) METHOD FOR IDENTIFYING HETERO-MULTIMERIC MODIFIED UBIQUITIN PROTEINS WITH BINDING CAPABILITY TO LIGANDS

(75) Inventors: Anja Kunert, Halle/Saale (DE); Jörg Narkamp, Halle/Saale (DE); Arnd Steuernagel, Göttingen (DE); Markus Fiedler, Halle/Saale (DE); Erik Fiedler, Halle/Saale (DE); Thomas Göttler, Halle/Saale (DE)

(73) Assignee: Scil Proteins GmbH, Halle (DE)

( * ) Notice: Subject to any disclaimer, the term of this patent is extended or adjusted under 35 U.S.C. 154(b) by 0 days.

(21) Appl. No.: 13/144,809

(22) PCT Filed: Dec. 14, 2010

(86) PCT No.: PCT/EP2010/069674

§ 371 (c)(1), (2), (4) Date: Sep. 29, 2011

(87) PCT Pub. No.: WO2011/073214

PCT Pub. Date: Jun. 23, 2011

(65) Prior Publication Data

US 2013/0157878 A1 Jun. 20, 2013

(30) Foreign Application Priority Data

Dec. 14, 2009 (EP) .................................... 09179147
May 7, 2010 (EP) .................................... 10162264
Oct. 8, 2010 (EP) .................................... 10186980

(51) Int. Cl.

*C40B 30/04* (2006.01)
*G01N 33/68* (2006.01)
*C07K 14/435* (2006.01)
*C07K 14/47* (2006.01)
*C12N 15/10* (2006.01)
*C40B 40/10* (2006.01)
*C40B 50/06* (2006.01)

(52) U.S. Cl.

CPC ........ *C12N 15/1034* (2013.01); *C12N 15/1037* (2013.01); *C12N 15/1041* (2013.01); *C07K 14/435* (2013.01); *C07K 14/47* (2013.01); *G01N 33/6845* (2013.01); *G01N 33/6878* (2013.01)

USPC .................. 506/7; 506/18; 506/26; 436/501; 435/320.1

(58) Field of Classification Search

CPC .. C07K 14/435; C07K 14/47; C12N 15/1037; C12N 15/1041; C12N 15/1034; C12N 15/1062; G01N 33/6845; G01N 33/6878

USPC .............................................. 506/7, 9, 18, 26

See application file for complete search history.

(56) References Cited

U.S. PATENT DOCUMENTS

| | | | |
|---|---|---|---|
| 4,873,192 | A | 10/1989 | Kunkel |
| 5,789,166 | A | 8/1998 | Bauer et al. |
| 5,958,684 | A | 9/1999 | Van Leeuwen et al. |
| 6,569,677 | B1 | 5/2003 | Legrand et al. |
| 6,673,901 | B2 | 1/2004 | Koide |
| 6,799,121 | B2 | 9/2004 | Chu et al. |
| 7,250,297 | B1 | 7/2007 | Beste et al. |
| 7,601,803 | B1 | 10/2009 | Fiedler et al. |
| 7,838,629 | B2 | 11/2010 | Fiedler et al. |
| 2003/0045681 | A1 | 3/2003 | Neri et al. |
| 2003/0073623 | A1 | 4/2003 | Drmanac et al. |
| 2004/0043386 | A1 | 3/2004 | Pray et al. |
| 2006/0058510 | A1 | 3/2006 | Skerra et al. |
| 2006/0099686 | A1 | 5/2006 | Fiedler et al. |
| 2007/0111287 | A1 | 5/2007 | Fiedler et al. |
| 2007/0248536 | A1 | 10/2007 | Fiedler et al. |
| 2008/0171851 | A1 | 7/2008 | Fiedler et al. |
| 2010/0130720 | A1 | 5/2010 | Schraeml et al. |
| 2013/0011334 | A1 | 1/2013 | Steuernagel et al. |
| 2013/0097737 | A1 | 4/2013 | Kovalic et al. |

FOREIGN PATENT DOCUMENTS

| | | | |
|---|---|---|---|
| AU | 2010332932 | | 6/2011 |
| AU | 2010332938 | | 6/2011 |
| CN | 1956996 | | 5/2007 |
| FR | 2 761 688 | A | 10/1998 |
| WO | WO97/16556 | | 5/1997 |
| WO | WO98/54312 | | 12/1998 |
| WO | WO01/04144 | | 1/2001 |
| WO | WO2004/106368 | | 12/2004 |
| WO | WO2005/044845 | | 5/2005 |
| WO | WO2005/059131 | | 6/2005 |

(Continued)

OTHER PUBLICATIONS

Rahighi et al. (Cell, 2009, 136:1098-1109).*

(Continued)

*Primary Examiner* — Christopher M Babic
*Assistant Examiner* — Jeremy C Flinders
(74) *Attorney, Agent, or Firm* — Jenkins, Wilson, Taylor & Hunt, P.A.

(57) ABSTRACT

The present invention refers to a method for identifying hetero-multimeric ubiquitins with binding capability to a ligand. Furthermore, the invention provides DNA libraries encoding for a population of said hetero-multimeric ubiquitins as well as protein libraries obtained by expression of said DNA libraries, cells and phages containing said DNA or proteins, polynucleotides encoding for said fusion proteins and vectors comprising said polynucleotides. Further new binding proteins based on hetero-multimeric ubiquitin being able to bind specifically with high affinity to selected ligands are provided.

13 Claims, 29 Drawing Sheets

(56) References Cited

FOREIGN PATENT DOCUMENTS

| | | |
|---|---|---|
| WO | WO2006/040129 | 4/2006 |
| WO | WO2006/119897 | 11/2006 |
| WO | WO2007/115837 | 10/2007 |
| WO | WO2007/128563 | 11/2007 |
| WO | WO2008/022759 | 2/2008 |
| WO | WO2008/059011 | 5/2008 |
| WO | WO2008/096012 | 8/2008 |
| WO | WO2011/073208 | 6/2011 |
| WO | WO2011/073209 | 6/2011 |

OTHER PUBLICATIONS

Lo et al. (Mol. Cell, 2009, 33:602-615).*
Dikic et al. (Nat. Rev. Mol. Cell Biol., 2009, 10:659-671).*
International Preliminary Report on Patentability corresponding to International Patent Application No. PCT/EP2010/069674 dated Jun. 28, 2012.
International Search Report corresponding to International Patent Application No. PCT/EP2010/069674 dated Jun. 17, 2011.
Abedi et al, "Green fluorescent protein as a scaffold for intracellular presentation of peptides," Nucleic Acids Research. vol. 26, No. 2 pp. 623-630 (1998).
Advisory Action corresponding to U.S. Appl. No. 10/030,605 dated Oct. 13, 2006.
Advisory Action corresponding to U.S. Appl. No. 12/072,959 dated May 18, 2010.
Advisory Action corresponding to U.S. Appl. No. 11/732,632 dated Jun. 30, 2010.
Baker et al., "Protein Expression Using Cotranslational Fusion and Cleavage of Ubiquitin," The Journal of Biological Chemistry. vol. 269, No. 41 pp. 25381-25386 (1994).
Beal et al., "Surface hydrophobic residues of multiubiquitin chains essential for proteolytic targeting," PNAS. vol. 93 pp. 861-866 (1996).
Beste, et al., "Small antibody-like proteins with prescribed ligand specificities derived from the lipocalin fold," PNAS. vol. 96 pp. 1898-1903 (1999).
Bird et al., "Single-Chain Antigen-Binding Proteins," Science. vol. 242 pp. 423-426 (1988).
Bofill et al., "Engineering Stabilising beta-Sheet Interactions into a Conformationally Flexible Region of the Folding Transition State of Ubiquitin," Journal of Molecular Biology, London, GB, vol. 353, No. 2, pp. 373-384 (Oct. 21, 2005), XP005086541 ISSN: 0022-2836.
Bolton et al., "Structure and Properties of a Dimeric N-terminal Fragment of Human Ubiquitin," Journal of Molecular Biology. vol. 314 pp. 773-787 (2001).
Brinkmann et al., "A recombinant immunotoxin containing a disulfide-stabilized Fv-fragment," PNAS. vol. 90 pp. 7538-7542 (1993).
Brinkmann et al., "Stabilization of a Recombinant Fv Fragment by Base-Loop Interconnection and VH-VL Permutation," Journal of Molecular Biology. vol. 268 pp. 107-117 (1997).
Buchberger et al., "The UBX Domain: A Widespread Ubiquitin-Like Module," Journal of Molecular Biology. vol. 307, No. 1 pp. 17-24 (2001).
Burch, T.J., and Haas, A.L., "Site-directed mutagenesis of ubiquitin. Differential roles for arginine in the interaction with ubiquitin-activating enzyme," Biochemistry. vol. 33, No. 23 pp. 7300-7308 (1994) [Abstract].
Campion et al., "Biochemical Properties of Site-Directed Mutants of Human Epidermal Growth Factor: Importance of Solvent-Exposed Hydrophobic Residues of the Amino-Terminal Domain in Receptor Binding," Biochemistry. vol. 29, No. 42 pp. 9988-9993 (1990).
Connolly, "Solvent-Accessible Surfaces of Proteins and Nucleic Acids." Science. vol. 221, No. 4612 pp. 709-713 (1983).
Daugherty et al., "Antibody affinity maturation using bacterial surface display," Protein Engineering. vol. 11, No. 9 pp. 825-832 (1998).
de Kruif et al., "Selection and Application of Human Single Chain Fv Antibody Fragments from a Semi-synthetic Phage Antibody Display Library with Designed CDR3 Regions," Journal of Molecular Biology. vol. 248 pp. 97-105 (1995).
Ebersbach et al., "Affilin-Novel Binding Molecules Based on Human (-B-Crystallin, an All (-Sheet Protein," Journal of Molecular Biology. vol. 372 pp. 172-185 (2007).
Ecker et al., "Gene Synthesis, Expression, Structures, and Functional Activities of Site-specific Mutants of Ubiquitin," The Journal of Biological Chemistry, vol. 262, No. 29 pp. 14213-14221 (1987).
Ermolenko et al., "Noncharged amino acid residues at the solvent-exposed positions in the middle and at the C terminus of the alpha-helix have the same helical propensity," Protein Science, vol. 12, No. 6, pp. 1169-1176 (Jun. 2003), XP00243791 T ISSN: 0961-8368.
European Office Action corresponding to European Patent Application No. 00 944 034.8-2401 dated Oct. 7, 2004. [not in English; P13840].
European Search Report corresponding to European Patent Application No. EP 10181802.9-2401 dated Feb. 10, 2011.
Fiedler et al., "AffilinTM Molecules: Novel Ligands for Bioseparation," Trans IChemE, Part C, Food and Bioproducts Processing. vol. 84, No. C1 pp. 3-8 (2006).
Finucane et al., "Core-Directed Protein Design. I. An Experimental Method for Selecting Stable Proteins from Combinatorial Libraries," Biochemistry. vol. 38 pp. 11604-11612 (1999).
Finucane, et al., "Core-Directed Protein Design. II. Rescue of a Multiply Mutated and Destabilized Variant of Ubiquitin." Biochemistry. vol. 38, No. 36 pp. 11613-11623 (1999).
Gebauer, M., and Skerra, A., "Engineered protein scaffolds as next-generation antibody therapeutics," Current Opinion in Chemical Biology. vol. 13 pp. 245-255 (2009).
Grabulovski et al., "A Novel, Non-immunogenic Fyn SH3-derived Binding Protein with Tumor Vascular Targeting Properties," The Journal of Biological Chemistry. vol. 282, No. 5 pp. 3196-3204 (2007).
Guo et al., "Protein tolerance to random amino acid change," PNAS. vol. 101, No. 25 pp. 9205-9210 (2004).
Hanes, J., and Pluckthun, A., "In vitro selection and evolution of functional proteins by using ribosome display," PNAS. vol. 94 pp. 4937-4942 (1997).
Hanes et al., "Picomolar affinity antibodies from a fully synthetic naive library selected and evolved by ribosome display," Nature Biotechnology. vol. 18 pp. 1287-1292 (2000).
Hanes et al., "Ribosome display efficiently selects and evolves high-affinity antibodies in vitro from immune libraries," PNAS. vol. 95 pp. 14130-14135 (1998).
He and Taussig, "Antibody-ribosome-mRNA(ARM) complexes as efficient selection particles for in vitro display and evolution of antibody combining sites," Nucleic Acids Research. vol. 25, No. 24 pp. 5132-5134 (1997).
Hey et al., "Artificial, non-antibody binding proteins for pharmaceutical and industrial applications," Trends in Biotechnology. vol. 23, No. 10 pp. 514-522 (2005).
http://scop.mrc-lmb.cam.ac.uk/scop/data/scop.b.e.ca.html, "Fold: beta-Grasp (ubiquitin-like)," Mar. 15, 2004. [Abstract].
International Preliminary Report on Patentability corresponding to International Application No. PCT/EP2007/062375 dated May 19, 2009.
International Search Report corresponding to International Patent Application No. PCT/EP2004/005730 dated Oct. 5, 2004.
International Search Report corresponding to International Patent Application No. PCT/EP2000/006698 dated Feb. 2, 2001.
International Search Report corresponding to International Patent Application No. PCT/EP2005/010932 dated Apr. 11, 2006.
Jackson "Ubiquitin: a small protein folding paradigm." *Org. Biomol. Chem.* vol. 4(10) pp. 1845-1853 (2006).
Jentsch, S., and Pyrowolakis, G., "Ubiquitin and its kin: how close are the family ties?" Trends in Cell Biology. vol. 10 pp. 335-342 (2000).
Khorasanizadeh et al., "Folding and stability of a tryptophan-containing mutant of ubiquitin." *Biochemistry* 32(27): 7054-63 (1993).
Kiel, C., and Serrano, L., "The Ubiquitin Domain Superfold: Structure-based Sequence Alignments and Characterization of Binding Epitopes," J. Mol. Biol. vol. 355 pp. 821-844 (2006).

(56) References Cited

OTHER PUBLICATIONS

Knappik et al., "Fully Synthetic Human Combinatorial Antibody Libraries (HuCAL) Based on Modular Consensus Frameworks and CDRs Randomized with Trinucleotides," Journal of Molecular Biology. vol. 296 pp. 57-86 (2000).
Koide et al., "The Fibronectin Type III Domain as a Scaffold for Novel Binding Proteins," Journal of Molecular Biology. vol. 284 pp. 1141-1151 (1998).
Krantz et al., "Discerning the Structure and Energy of Multiple Transition States in Protein Folding using Ψ-Analysis," J. Mol. Biol. vol. 337 pp. 463-475 (2004).
Ku, J., and Schultz, P.G., "Alternate protein frameworks for molecular recognition," PNAS. vol. 92 pp. 6552-6556 (1995).
Larsen et al., "The Ubiquitin Superfamily: Members, Features, and Phylogenies," Journal of Proteome Research. vol. 1 pp. 411-419 (2002).
Laub et al., "Localized solution structure refinement of an F45W variant of ubiquitin using stochastic boundary molecular dynamics and NMR distance restraints," Protein Science. vol. 4 pp. 973-982 (1995).
Lazar, C.N., and Wang, H., "De novo design of the hydrophobic core of ubiquitin," Protein Science. vol. 6 pp. 1167-1178 (1997).
Lipovsek, D., and Pluckthun, A., "In-vitro protein evolution by ribosome display and mRNA display," J. Immunol. Methods. vol. 290 pp. 51-67(2004).
Loladze et al., "Both helical propensity and side-chain hydrophobicity at a partially exposed site in alpha-helix contribute to the thermodynamic stability of ubiquitin," Proteins, vol. 58, No. 1, pp. 1-6 (Jan. 1, 2005), XP002437914 ISSN: 1097-0134.
Mayr et al., "Domain Interactions and Connecting Peptides in Lens Crystallins," Journal of Molecular Biology. vol. 235 pp. 84-88 (1994).
McConnell, S.J., and Hoess, R.H. "Tendamistat as a Scaffold for Conformationally Constrained Phage Peptide Libraries," The Journal of Molecular Biology. vol. 250 pp. 460-470 (1995).
Miura et al., "Characterization of the Binding Interface between Ubiquitin and Class I Human Ubiquitin-conjugating Enzyme 2b by Multidimensional Heteronuclear NMR Spectroscopy in Solution," Journal of Molecular Biology. vol. 290 pp. 213-228 (1999).
Müller et al., "SUMO, ubiquitin's mysterious cousin," Nat. Rev. Mol. Cell Biol. vol. 2 pp. 202-210 (2001).
Müller, H.N., and Skerra, A., "Grafting of a High-Affinity Zn(II)-Binding Site on the β-Barrel of Retional-Binding Protein Results in Enhanced Folding Stability and Enables Simplified Purification," Biochemistry. vol. 33, No. 47 pp. 14126-14135 (1994).
Nord et al., "Binding proteins selected from combinatorial libraries of an (-helical bacterial receptor domain," Nature Biotechnology. vol. 15 pp. 772-777 (1997).
Notice of Allowance corresponding to U.S. Appl. No. 10/030,605 dated Apr. 14, 2009.
Notice of Allowance corresponding to U.S. Appl. No. 11/732,632 dated Aug. 23, 2010.
Notification of Transmittal of Translation of the International Preliminary Report on Patentability (Chapter I of the Patent Cooperation Treaty) corresponding to International Patent Application No. PCT/EP2004/005730 dated Apr. 13, 2006.
Notification of Transmittal of Translation of the International Preliminary Report on Patentability (Chapter I or Chapter II of the Patent Cooperation Treaty) corresponding to International Application No. PCT/EP2005/010932 dated May 3, 2007.
Notification of Transmittal of the International Search Report and the Written Opinion of the International Searching Authority, or the Declaration corresponding to International Patent Application No. PCT/EP2010/069674 dated Jun. 17, 2011.
Nygren, P., and Uhlen, M., "Scaffolds for engineering novel binding sites in proteins," Current Opinion in Structural Biology. vol. 7 pp. 463-469 (1997).
Official Action corresponding to U.S. Appl. No. 12/072,959 dated Jan. 27, 2009.
Official Action corresponding to U.S. Appl. No. 10/030,605 dated Sep. 21, 2004.
Official Action corresponding to U.S. Appl. No. 10/030,605 dated Feb. 15, 2005.
Official Action corresponding to U.S. Appl. No. 10/030,605 dated Aug. 10, 2005.
Official Action corresponding to U.S. Appl. No. 10/030,605 dated Apr. 12, 2006.
Official Action corresponding to U.S. Appl. No. 10/030,605 dated Feb. 28, 2007.
Official Action corresponding to U.S. Appl. No. 10/030,605 dated Nov. 16, 2007.
Official Action corresponding to U.S. Appl. No. 11/656,646 dated Sep. 1, 2009.
Official Action corresponding to U.S. Appl. No. 11/656,646 dated May 25, 2010.
Official Action corresponding to U.S. Appl. No. 10/030,605 dated Jul. 1, 2008.
Official Action corresponding to U.S. Appl. No. 11/656,646 dated Nov. 13, 2009.
Official Action corresponding to U.S. Appl. No. 11/283,332 dated Jan. 9, 2008.
Official Action corresponding to U.S. Appl. No. 11/283,332 dated May 30, 2008.
Official Action corresponding to U.S. Appl. No. 11/283,332 dated Nov. 28, 2008.
Official Action corresponding to U.S. Appl. No. 11/283,332 dated Sep. 4, 2009.
Official Action corresponding to U.S. Appl. No. 12/072,959 dated Jul. 24, 2008.
Official Action corresponding to U.S. Appl. No. 11/283,332 dated Mar. 3, 2010.
Official Action corresponding to U.S. Appl. No. 12/072,959 dated Jan. 5, 2010.
Official Action corresponding to U.S. Appl. No. 11/732,632 dated Jun. 3, 2009.
Official Action corresponding to U.S. Appl. No. 11/732,632 dated Aug. 21, 2009.
Official Action corresponding to U.S. Appl. No. 11/732,632 dated Mar. 19, 2010.
Official Action corresponding to U.S. Appl. No. 12/514,550 dated Aug. 3, 2011.
Official Action corresponding to U.S. Appl. No. 12/514,550 dated Sep. 15, 2011.
Official Action corresponding to U.S. Appl. No. 12/514,550 dated Mar. 12, 2012.
Ohashi et al., "Efficient protein selection based on ribosome display system with purified components," Biochem. Biophys. Res. Commun. vol. 352 pp. 270-276 (2007).
Pack, P., and Pluckthun, A., "Miniantibodies: Use of Amphipathic Helices to Produce Functional, Flexibly Linked Dimeric Fv Fragments with High Avidity in *Escherichia coli,*" Biochemsitry. vol. 31, No. 6 pp. 1579-1584 (1992).
Paschke, M., and Höhne, W., "A twin-arginine translocation (Tat)-mediated phage display system," Gene. vol. 350, No. 1 pp. 79-88 (2005).
Richardson et al., "Looking at proteins: representations, folding, packing, and design," Biophysical Journal. vol. 63 pp. 1186-1209 (1992).
Riddle at al., "Functional rapidly folding proteins from simplified amino acid sequences," Nature Structural Biology. vol. 4, No. 10 pp. 805-809 (1997).
Schaffitzel et al., "In Vitro Selection and Evolution of Protein-Ligand Interactions by Ribosome Display," Protein-Protein Interactions, A Molecular Cloning Manual, E. Golemis, Ed. Cold Spring Harbor Laboratory Press, New York. Chapter 30 pp. 535-567 (2001).
Skerra and Plückthun, "Assembly of a Functional Immunoglobulin Fv Fragment in *Escherichia coli,*" Science vol. 240 pp. 1038-1041 (1988).
Skerra, "Engineered protein scaffolds for molecular recognition," Journal of Molecular Recognition. vol. 13, No. 4 pp. 167-187 (2000).

(56) References Cited

OTHER PUBLICATIONS

Smith et al., "Small Binding Proteins Selected from a Conbinatorial Repertoire of Knottins Displayed on Phage," Journal of Molecular Biology. vol. 277, No. 2 pp. 317-332 (1998).
Stemmer, "Rapid evolution of a protein in vitro by DNA shuffling," Nature. vol. 370 pp. 389-391 (1994).
Wells, "Additivity of Mutational Effects in Proteins," Biochemistry. vol. 29, No. 37 pp. 8509-8517 (1990).
Wells and Lowmann, "Rapid evolution of peptide and protein binding properties in vitro," Current Opinion in Biotechnology. vol. 3 pp. 355-362 (1992).
Winter, "Synthetic human antibodies and a strategy for protein engineering," FEBS Letters. vol. 430 pp. 92-94 (1998).
Yang at al., "Relationship between folding and function in a sequence-specific miniature DNA-binding protein," Biochemistry. vol. 44, No. 20, pp. 7469-7478 (May 24, 2005), XP002437916 ISSN: 0006-2960.
Yeh et al., "Ubiquitin-like proteins: new wines in new bottles," Gene. vol. 248, Nos. 1-2 pp. 1-14 (2000).
You, L., and Arnold, F.H., "Directed evolution of subtilisin E in *Bacillus subtilis* to enhance total activity in aqueous dimethylformamide," Protein Engineering. vol. 9, No. 1 pp. 77-83 (1994).
Young et al., "Thermal stabilization of a single-chain Fv antibody fragment by introduction of a disulphide bond," FEBS Letters. vol. 377 pp. 135-139 (1995).
Zahnd et al., "Ribosome display: selecting and evolving proteins in vitro that specifically bind to a target," Nature Methods. vol. 4, No. 3 pp. 269-279 (2007).
Zhang et al., "Directed evolution of a fucosidase from a galactosidase by DNA shuffling and screening," PNAS. vol. 94 pp. 4504-4509 (1997).
Branden, C., and Tooze, J., "Introduction to Protein Structure," Chapter 16, Garland Publishing Inc.: New York, New York p. 247 (1991).
Corrected Notice of Allowability corresponding to U.S. Appl. No. 11/656,646 dated Sep. 26, 2013.
Deed of Grant corresponding to Australian Patent No. 2010332932 dated May 2, 2013.
Deed of Grant corresponding to Australian Patent No. 2010332938 dated Apr. 4, 2013.
Hershko, A., and Ciechanover, A., "The Ubiquitin System," Annu. Rev. Biochem. vol. 67 pp. 425-479 (1998).
Intent to Grant corresponding to European Patent Application No. EP 10 787 815.9-1410 dated Aug. 13, 2013.
International Preliminary Report on Patentability (Chapter I of the Patent Cooperation Treaty) corresponding to International Patent Application No. PCT/EP2010/069665 dated Jun. 19, 2012.
International Search Report corresponding to International Patent Application No. PCT/EP2007/062375 dated Apr. 25, 2008.
International Search Report corresponding to International Patent Application No. PCT/EP2010/069665 dated Apr. 13, 2011.
Interview Summary correponding to U.S. Appl. No. 11/283,332 dated Dec. 13, 2013.
Interview Summary corresponding to U.S. Appl. No. 11/283,332 dated Oct. 10, 2013.
Interview Summary corresponding to U.S. Appl. No. 12/072,959 dated Dec. 13, 2013.
Interview Summary corresponding to U.S. Appl. No. 12/072,959 dated Oct. 15, 2013.
Interview Summary corresponding to U.S. Appl. No. 12/514,550 dated Dec. 13, 2011.
Interview Summary corresponding to U.S. Appl. No. 12/514,550 dated Jun. 12, 2012.
Notice of Allowance corresponding to U.S. Appl. No. 11/656,646 dated Aug. 27, 2013.
Notice of Allowance corresponding to U.S. Appl. No. 12/514,550 dated Sep. 10, 2013.
Notification Concerning Transmittal of International Preliminary Report on Patentability (Chapter I of the Patent Cooperation Treaty) corresponding to International Patent Application No. PCT/EP2010/069666 dated Jun. 28, 2012.
Official Action corresponding to Chinese Patent Application No. 201080056911.6 dated Jul. 31, 2013. [Translation].
Official Action corresponding to Korean Patent Application No. 10-2011-7018847 dated Jan. 30, 2013. [Translation].
Official Action corresponding to U.S. Appl. No. 11/283,332 dated Sep. 3, 2013.
Official Action corresponding to U.S. Appl. No. 12/072,959 dated Aug. 30, 2013.
Official Action corresponding to U.S. Appl. No. 13/142,195 dated Feb. 11, 2013.
Official Action corresponding to U.S. Appl. No. 13/142,195 dated May 29, 2013.
Search Report corresponding to Chinese Patent Application No. 201080056911.6 dated Jun. 14, 2013. [Translation].
Witkowski et al., "Conversion of a beta-ketoacyl synthanse to a malonyl decarboxylase by replacement of the active-site cysteine with glutamine," Biochemistry, vol. 38 pp. 11643-11650 (1999).

* cited by examiner

Figure 1: The recombination of the front monomer of clone 41B10 with a different rear monomer led to an increase of affinity as well as specificity
Figure 1A: Primary selection of SPW28-41B10
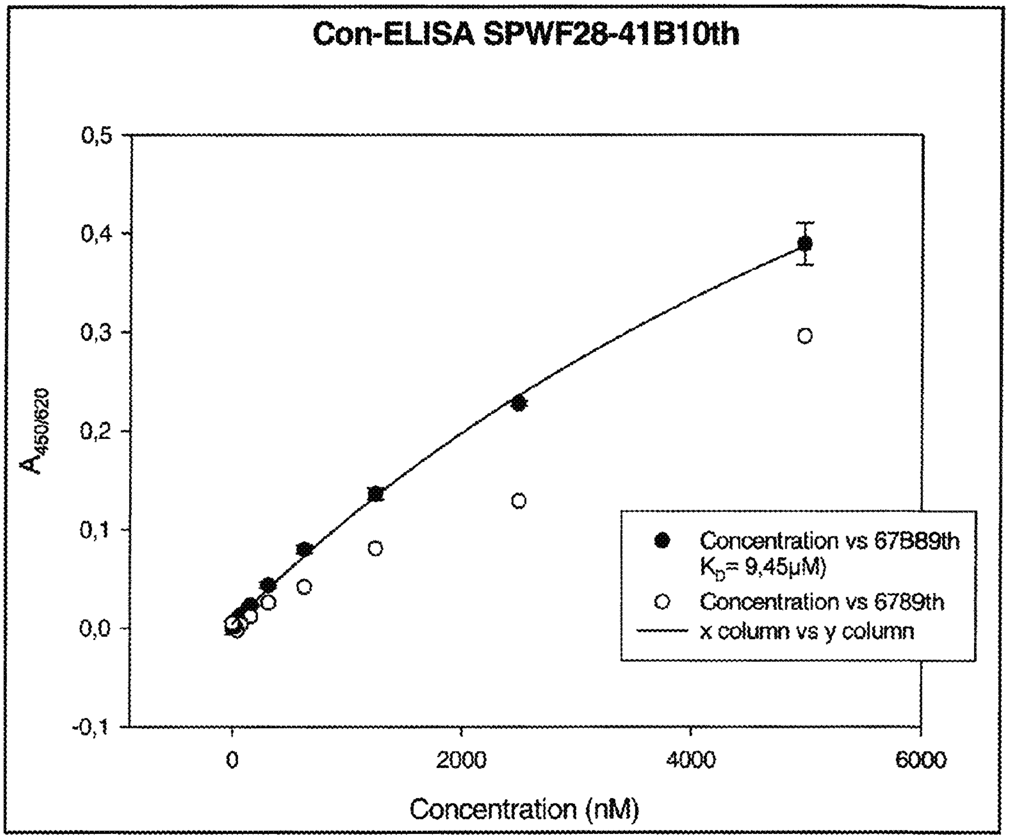

Figure 1B: After recombination with a different rear monomer (SPWF28-46H9)
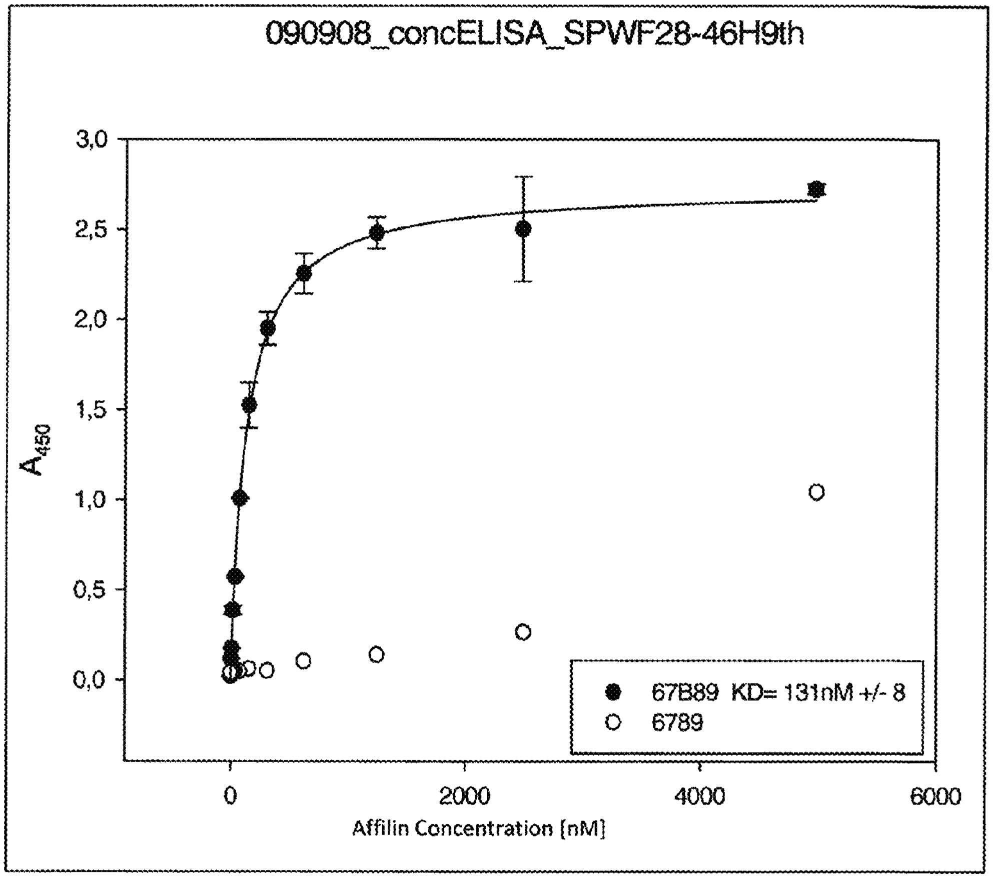
Affilin = modified ubiquitin-based ED-B binding protein concentration

Figure 2 – Affinity and Activity of a Modified ubiquitin-based ED-B binding protein Dimer Molecule fused to a Cytokine

- Apotosis inducing activity of Affilin® cytokine fusion: $EC_{50}$ 0,78 ±0,24 pM
- Apoptosis inducing activity of free cytokine: $EC_{50}$ 3,14 ± 3,59 pM

Figure 2 A shows the high affinity of modified ubiquitin based ED-B binding hetero-dimer 24H12 (Kd 50.7 nM = 50.7 x $10^{-9}$ M).
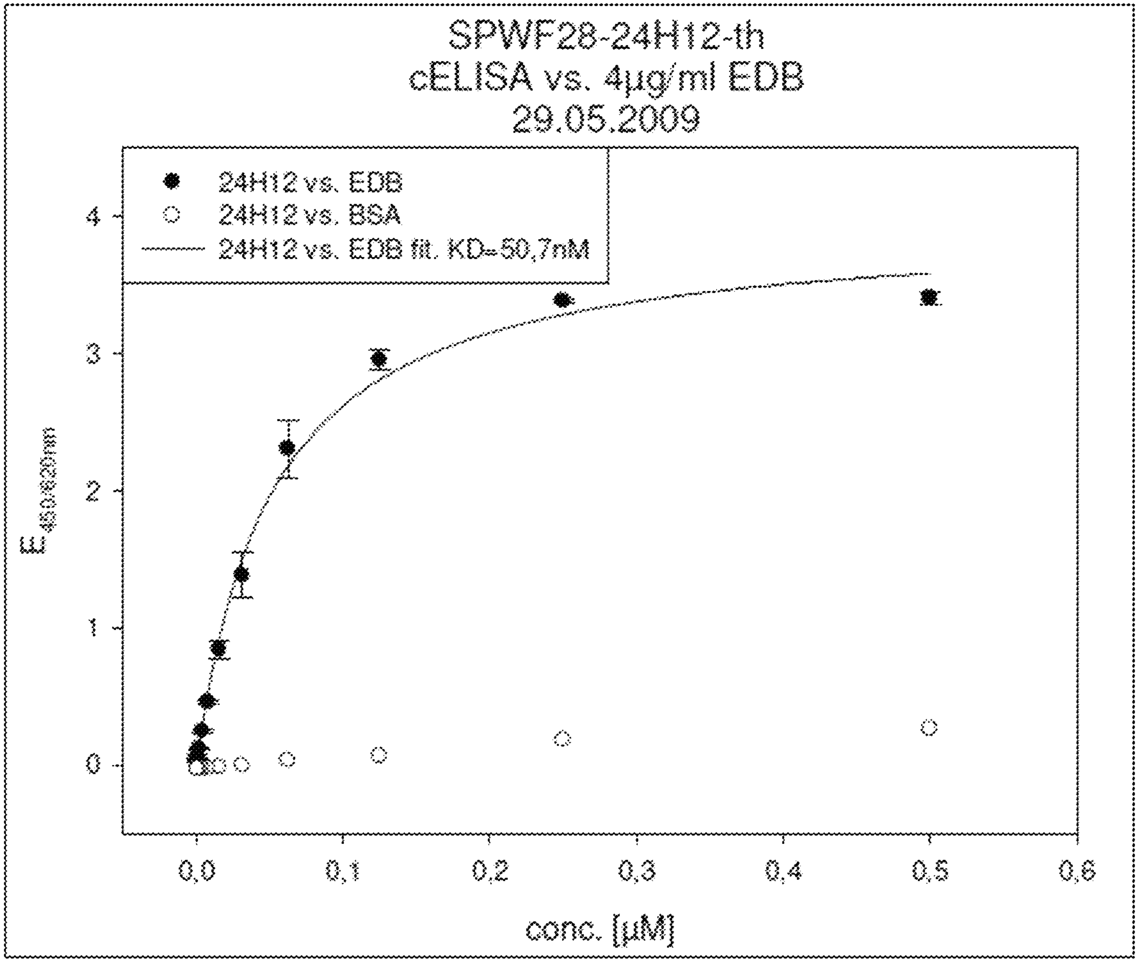

Figure 2 B shows the increased affinity of modified ubiquitin based ED-B binding heterodimer 24H12 fused to cytokine TNFalpha to result in a multimerisation of the heterodimer (Kd = 5.6 nM = 5.6 x $10^{-9}$ M.
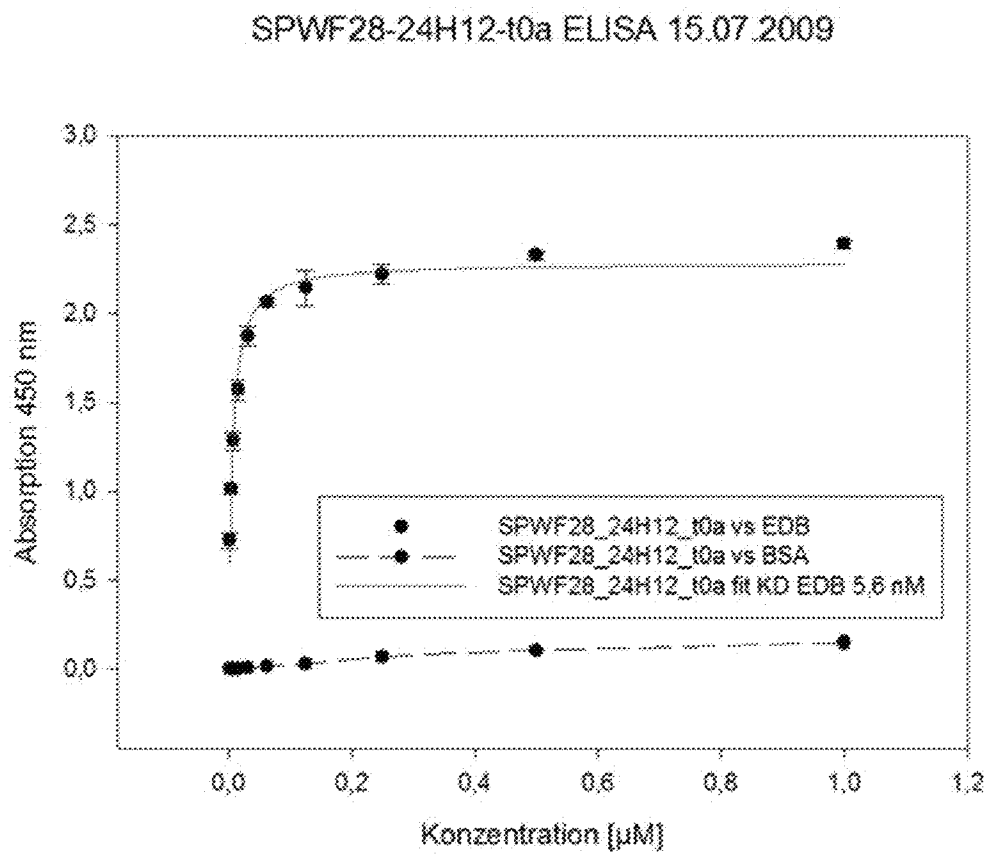

Figure 2 C Analysis of candidates from dimer library selection, for example 9E12 22D1 24H12 41B10

| Variant | Target ED_B | | | | Target c-FN |
|---|---|---|---|---|---|
| | $K_D$ ELISA | Biacore | | | $K_D$ ELISA |
| | | $K_{on}$ ($M^{-1}s^{-1}$) | $K_{off}$ ($s^{-1}$) | $K_D$ (nM) | |
| **9E12** | 9,5 nM | Not determinable | Not determinable | Not determinable | 61,2 nM |
| **22D1** | 594 nM | - | - | - | 711 nM |
| **24H12** | 50,7 nM | - | - | - | 286 nM |
| **41B10** | 310 nM | 293 | $1{,}82 \cdot 10^{-4}$ | 623 nM | 280 nM |

FIGURE 3: Contribution of different monomers to binding affinity and specificity
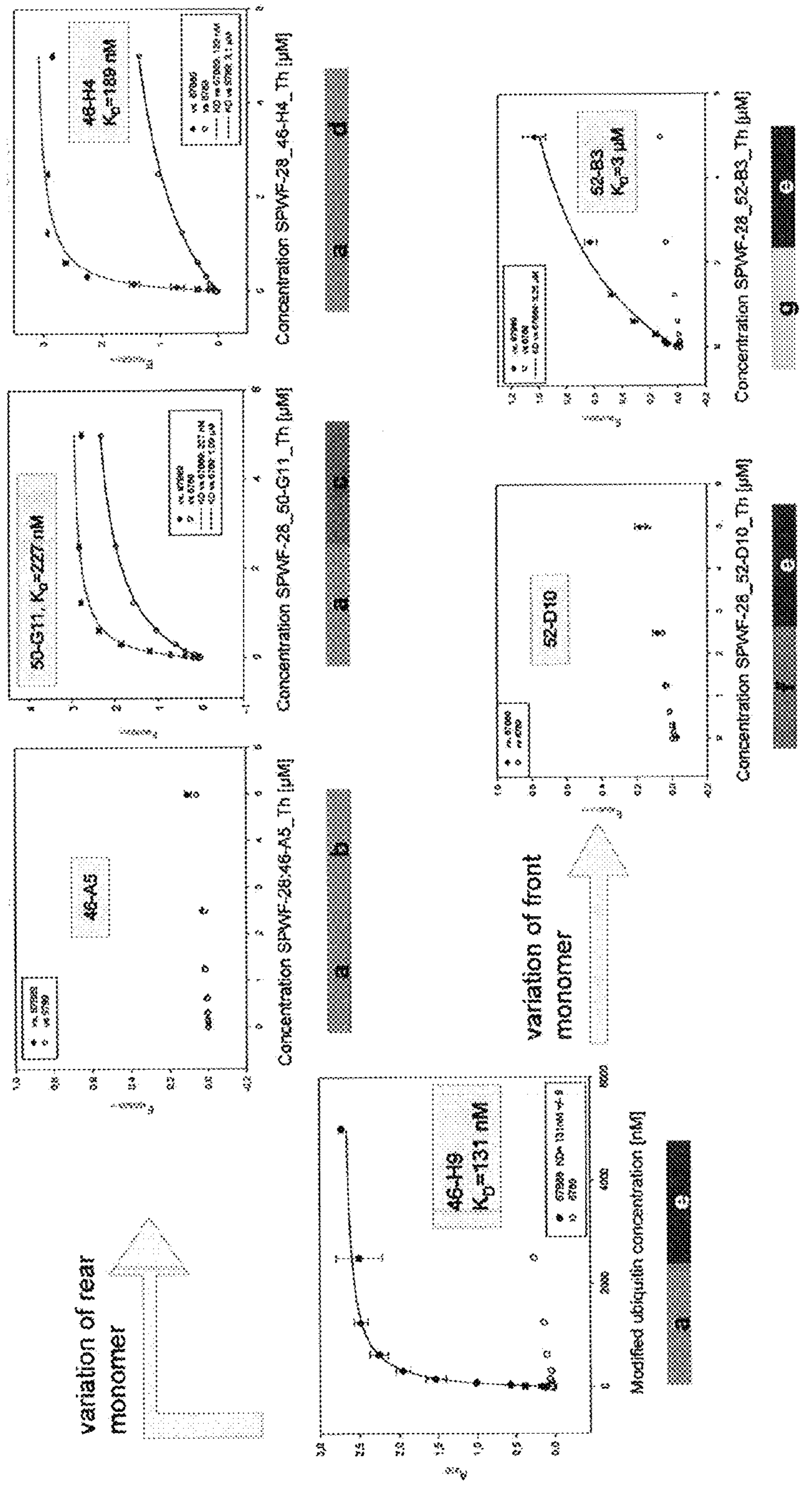

Multi-way Protein alignment
Sequences: 2 Scoring matrix BL O SUM 62

Sequence View: Similarity Format, Color behind non-matches

```
                  10        20        30        40        50        60        70        80        90
                   •         •         •         •         •         •         •         •         •
WubiHub-Protein   MQIFVKTLTGKTITLEVEPSDTIENVKAKIQDKEGIPPDQQRLIWAGKQLEDGRTLSDYNIQKESTLHLVLRLRGGSGGGGSGGGGIGMQ
pPR-IBAi-46H9_Ts  MGIYVRTLTGKTITLEVEPSDTIENVKAKIQDKEGIPPDQQRLIWAGKQLEDGRTLSDYNIPHPTLLHLVLRLRGGSGGGGSGGGGIGMQ

                  100       110       120       130       140       150       160
                   •         •         •         •         •         •         •
WubiHub-Protein   IFVKTLTGKTITLEVEPSDTIENVKAKIQDKEGIPPDQQRLIWAGKQLEDGRTLSDYNIQKESTLMLVLRLRGG
pPR-IBAi-46H9_Ts  IFVRTYTGKTITLEVEPSDTIENVKAKIQDKEGIPPDQQRLIWAGKQLEDGRTLSDYNIKPIAPLMLVLRLRGG
```

FIGURE 4

FIGURE 5: Sequence comparison of variant 1041-D11 with ubiquitin

```
1041-D11_TsX9          1  MQIFVWTWTGKTITLEVEPSDTIENVKAKIQDKEGIPPDQQRLIWAGKQLEDGRTLSDYN
Ub2_TsX9               1  MQIFVKTLTGKTITLEVEPSDTIENVKAKIQDKEGIPPDQQRLIWAGKQLEDGRTLSDYN
Ubi-Dimer wt (Pr       1  MQIFVKTLTGKTITLEVEPSDTIENVKAKIQDKEGIPPDQQRLIFAGKQLEDGRTLSDYN
Ubi-Monomer wt         1  MQIFVKTLTGKTITLEVEPSDTIENVKAKIQDKEGIPPDQQRLIFAGKQLEDGRTLSDYN

1041-D11_TsX9         61  IQRKFPLHLVLRLRGGIGMRIFVTTQTGKTITLEVEPSDTIENVKAKIQDKEGIPPDQQ
Ub2_TsX9              61  IQKESTLHLVLRLRGGIGMQIFVKTLTGKTITLEVEPSDTIENVKAKIQDKEGIPPDQQ
Ubi-Dimer wt (Pr      61  IQKESTLHLVLRLRGG----MQIFVKTLTGKTITLEVEPSDTIENVKAKIQDKEGIPPDQQ
Ubi-Monomer wt        61  IQKESTLHLVLRLRGG~~~~~~~~~~~~~~~~~~~~~~~~~~~~~~~~~~~~~~~~~~~~

1041-D11_TsX9        121  RLIWAGKQLEDGRTLSDYNIWSNWELHLVLRLRAA
Ub2_TsX9             121  RLIWAGKQLEDGRTLSDYNIQKESTLHLVLRLRAA
Ubi-Dimer wt (Pr     118  RLIFAGKQLEDGRTLSDYNIQKESTLHLVLRLRGG
Ubi-Monomer wt            ~~~~~~~~~~~~~~~~~~~~~~~~~~~~~~~~~~~
```

Figure 10
Fig. 10 A
4. SE-HPLC.
Complex with ED-B (67B89)
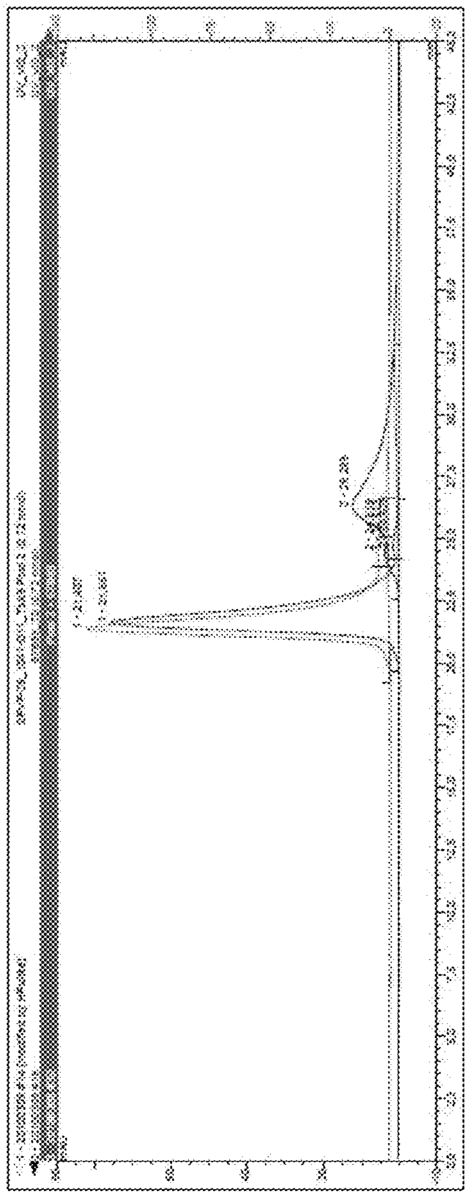
Fig. 10 B
No complex with control (6789)
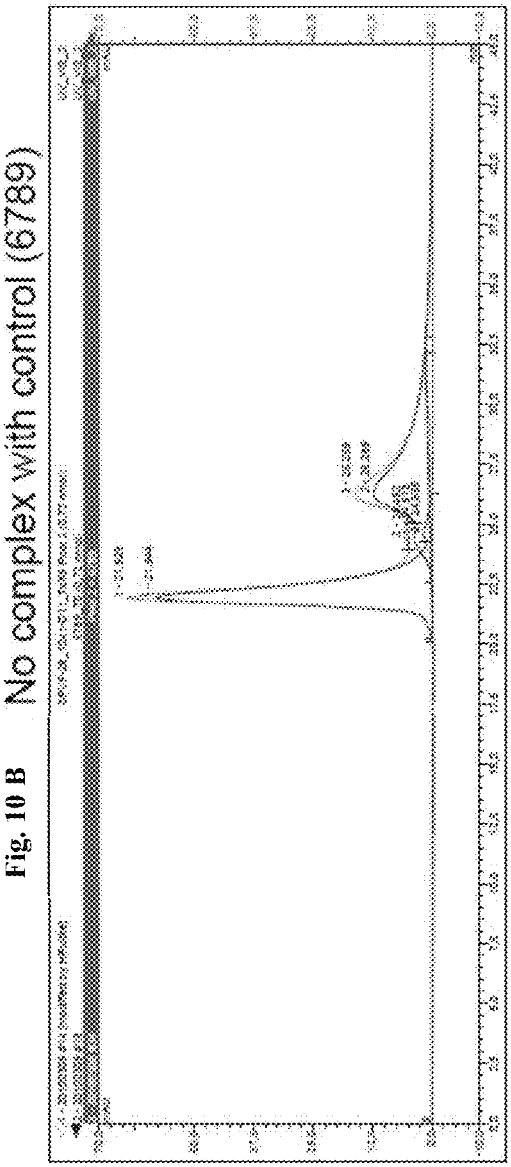

```
1111-B4_21231   1  ................gkva................................qd....................iw................krnpe..........aasggggsg....
1111-C9_21265   1  ................gkv.................................qd....................iw................krnpe..........aasggggsg....
1111-E10_21315  1  ..............ef....................................qd....................iw................gwhpe..........---------g...
1111-F6_21331   1  ..............pfw....................................qd....................iw................qprtl..........---------g...
1111-H12_21391  1  ..............efr....................................qd....................iw................qwhpe..........--e..
1111-H2_21371   1  ..............efr....................................qd....................iw................gwhpe..........---------g...

1111-B4_21231   89 ........rfm....................................................................etgvv..........
1111-C9_21265   89 ........rfm....................................................................etgvv..........
1111-E10_21315  80 ........r.e....................................................................lmgyv..........
1111-F6_21331   80 ........y.t....................................................................livai..........
1111-H12_21391  80 ........rfm....................................................................etgvv..........
1111-H2_21371   80 ........r.m....................................................................e-tgvv.........
```

Figure 13

| | Clone-ID | BDR1 | | linker | BDR2 | | Exchange |
|---|---|---|---|---|---|---|---|
| SPVF-31_1111-E10_TsX9 | 21315 | ef | gwhpe | ---------gggig | ze | lmgyv | |
| SPVF-31_1111-C9_TsX3 | 21265 | gv | krnpe | aasggggsggggig | zm | etgvv | |
| SPVF-31_1111-B4_TsX3 | 21231 | gv | krnpe | aasggggsggggig | zm | etgvv | T9A |
| SPVF-31_1111-F6_TsX9 | 21331 | pw | qprtl | ---------gggig | yt | llval | |
| | | | | | | | |
| SPVF-31_1111-H2_TsX9 | 21371 | ef | gwhpe | ---------gggig | zm | etgvv | |
| SPVF-31_1111-H12_TsX9 | 21391 | ef | gwhpe | ---------ggeig | zm | etgvv | G86E |

Figure 15A

Part A: Modifications in the first Ubiquitin monomer

Modifications in positions 2, 4, 6, 62-66
6-A12 1
mfiyvvtltgktitlevepsdtienvkakiqdkegippdqqrliwagkqledgrtlsdyniphyprlhlvlrlrggsggggsg
gggig Modifications in positions 2, 4, 6, 62-66, 68
16-A4 1
myivvltltgktitlevepsdtienvkakiqdkegippdqqrliwagkqledgrtlsdyniipqmalhlvlrlrggsggggsg
gggig Modifications in positions 2, 4, 6, 62-66, 72-74, and optionally 29
7-D1 1
mmiyvltltgktitlevepsdtienvkaeiqdkegippdqqrliwagkqledgrtlsdyniptdallhlvlrlrggsggggsg
gggig Modifications in positions 2, 4, 6, 62-66
14-D11 1
mliivgtltgktitlevepsdtienvkakiqdkegippdqqrliwagkqledgrtlsdyniptvnalhlvlrlrggsggggsg
gggig Modifications in positions 2, 4, 6, 62-66
12-E6 1
mligvrtltgktitlevepsdtienvkakiqdkegippdqqrliwagkqledgrtlsdynigrgtalhlvlrlrggsggggsg
gggig Modifications in positions 2, 4, 6, 62-66
12-G9 1
mfiwvvtltgktitlevepsdtienvkakiqdkegippdqqrliwagkqledgrtlsdynirsttmlhlvlrlrggsggggsg
gggig Modifications in positions 42, 44, 68, 70, 72-74, and optionally 5 further positions
1144-D11 1
mqifvktltgktitlevepsdtienveakiqdkegippdqqhltfagkqlgdgrtlsdyniqkestlslllgvwaa-------
-----

Modifications in positions 42, 44, 68, 70, 72-74, and optionally 3 further positions
1144-E9 1
mqifvktltgktitlevepsdtienvkakiqdkegippdqqnlhfagkqledgrtlsdyniqkestlklgltgfaa-------
-----

Modifications in positions 62-66, 70, 72-74
1076-H4 1
mfiyvvtltgktitlevepsdtienvkakiqdkegippdqqrliwagkqledgrtlsdyniphyprlqlklkhsaasggggsg
gggig Modifications in positions 2, 4, 6, 62-66, 70, 72-74
1081-B11 1
mfiyvvtltgktitlevepsdtienvkakiqdkegippdqqrliwagkqledgrtlsdyniphyprlqlqlkhdaasggggsg
gggig Modifications in positions 2, 4, 6, 62-66, 70, 72-74
1081-H11 1
mfiyvvtltgktitlevepsdtienvkakiqdkegippdqqrliwagkqledgrtlsdyniphyprlqlylksdaasggggsg
gggig Modifications in positions 2, 4, 6, 62-66, 70, 72-74
1082-A10 1
mfiyvvtltgktitlevepsdtienvkakiqdkegippdqqrliwagkqledgrtlsdyniphyprlqlslkddaasggggsg
gggig Modifications in positions 2, 4, 6, 62-66, 70, 72-74

Figure 15A (cont'd)

1082-A11 1
mfiyvvtltgktitlevepsdtienvkakiqdkegippdqqrliwagkqledgrtlsdyniphyprlhlrlqsqaasgggsg
ggslg Modifications in positions 2, 4, 6, 62-66, 70, 72-74
1088-A5 1
mfiyvvtltgktitlevepsdtienvkakiqdkegippdqqrliwagkqledgrtlsdyniphyprlhlklklaaasgggsg
ggslg Modifications in positions 2, 4, 6, 62-66, 70, 72-74
1091-A2 1
mfiyvvtltgktitlevepsdtienvkakiqdkegippdqqrliwagkqledgrtlsdyniphyprlhlhlhlhaasgggsg
ggslg Modifications in positions 2, 4, 6, 62-66, 70, 72-74
1094-D9 1
mfiyvvtltgktitlevepsdtienvkakiqdkegippdqqrliwagkqledgrtlsdyniphyprlhlkllhsaasgggsg
ggslg Part B: Modifications in the second Ubiquitin monomer Modifications in positions 6, 8, 62-66
6-A12 89
mqifvvtetgktitlevepsdtienvkakiqdkegippdqqrliwagkqledgrtlsdynilttgplhlvlrlrgg Modifications in positions 6, 8, 62-66
16-A4 89
mqifvvtetgktitlevepsdtienvkakiqdkegippdqqrliwagkqledgrtlsdynilrtgplhlvlrlrgg Modifications in positions 6, 8, 62-66
7-D1 89
mqifvvtstgktitlevepsdtienvkakiqdkegippdqqrliwagkqledgrtlsdynilthgplhlvlrlrgg Modifications in positions 6, 8, 62-66
14-D11 89
mqifvvtatgktitlevepsdtienvkakiqdkegippdqqrliwagkqledgrtlsdynilrtgplhlvlrlrgg Modifications in positions 6, 8, 62-66
12-E6 89
mqifvvtetgktitlevepsdtienvkakiqdkegippdqqrliwagkqledgrtlsdynilatgplhlvlrlrgg Modifications in positions 6, 8, 62-66
12-G9 89
mqifvvtetgktitlevepsdtienvkakiqdkegippdqqrliwagkqledgrtlsdynilrtgplhlvlrlrgg Modifications in positions 6, 8, 27, 62-66
1144-D11 77
mqifvetdtgktitlevepsdtienveakiqdkegippdqqrliwagkqledgrtlsdynigtdaalhlvlrlraa Modifications in positions 6, 8, 27, 62-66
1144-E9 77
mqifvctitgktitlevepsdtienvcakiqdkegippdqqrliwagkqledgrtlsdyniydqlslhlvlrlraa Modifications in positions 6, 8, 62-66
1076-H4 89
mqifvvtetgktitlevepsdtienvkakiqdkegippdqqrliwagkqledgrtlsdynilttgplhlvlrlraa Modifications in positions 6, 8, 62-66
1081-B11 89
mqifvvtetgktitlevepsdtienvkakiqdkegippdqqrliwagkqledgrtlsdynilttgplhlvlrlraa Modifications in positions 6, 8, 62-66
1081-H11 89
mqifvvtetgktitlevepsdtienvkakiqdkegippdqqrliwagkqledgrtlsdynilttgplhlvlrlraa Modifications in positions 6, 8, 62-66
1082-A10 89
mqifvvtetgktitlevepsdtienvkakiqdkegippdqqrliwagkqledgrtlsdynilttgplhlvlrlraa

Figure 15A (cont'd)

Modifications in positions 6, 8, 62-66
1082-A11 89
mqifvvtetgktitlevepsdtienvkakiqdkegippdqqrlifagkqledgrtlsdynilttgplhlvlrlraa Modifications in positions 6, 8, 62-66
1088-A5 89
mqifvvtetgktitlevepsdtienvkakiqdkegippdqqrlifagkqledgrtlsdynilttgplhlvlrlraa Modifications in positions 6, 8, 62-66
1091-A2 89
mqifvvtetgktitlevepsdtienvkakiqdkegippdqqrlifagkqledgrtlsdynilttgplhlvlrlraa Modifications in positions 6, 8, 62-66
1094-D9 89
mqifvvtetgktitlevepsdtienvkakiqdkegippdqqrlifagkqledgrtlsdynilttgplhlvlrlraa

FIGURE 15 B. TNFalpha binding of modified ubiquitin-based heterodimers

Figure A. Sequence of the heterodimeric ubiquitin binding protein SPWF-15_6-A12 with specificity for TNFalpha. Modifications are in positions 2, 4, 6, 62-66, 68 of the first ubiquitin monomer and in positions 6, 8, 62-66 in the second monomer. Linker between the two ubiquitin monomers: SGGGGSGGGGIG.

MFIYVVTLTGKTITLEVEPSDTIENVKAKIQDKEGIPPDQQRLIWAGKQLEDGRTLSDYNIPHYPRLQ
LVLRLRGGSGGGGSGGGGIGMQIFVVTETGKTITLEVEPSDTIENVKAKIQDKEGIPPDQQRLIWAGK
QLEDGRTLSDYNILTTGPLHLVLRLRGG

FIGURE 15 C. Concentration-dependent ELISA determines the high affinity binding of Kd 12 nM to TNF-alpha.

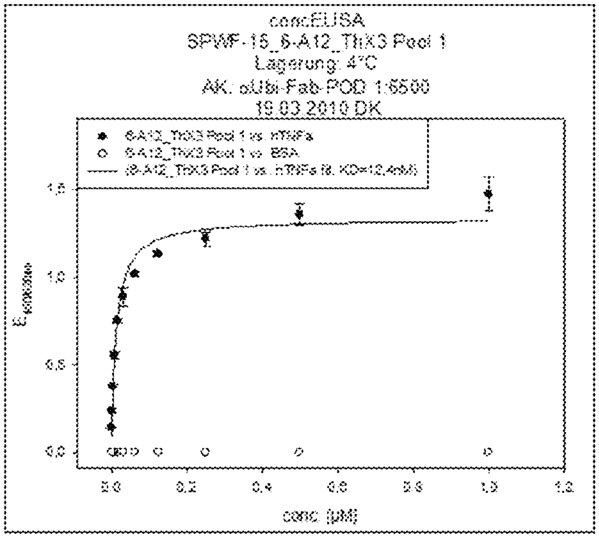

FIGURE 15 D. Sequence of the heterodimeric ubiquitin binding protein SPWF-15_16-D4_Th with specificity for TNFalpha. Modifications are in positions 2, 4, 6, 62-66 of the first ubiquitin monomer and in positions 6, 8, 62-66 in the second monomer. Linker between the two ubiquitin monomers: SGGGGSGGGGIG.

SPWF-15_16-D4_Th

MYIVVLTLTGKTITLEVEPSDTIENVKAKIQDKEGIPPDQQRLIWAGKQLEDGRTLSDYNIIPQMALH
LVLRLRGGSGGGGSGGGGIGMQIFVVTETGKTITLEVEPSDTIENVKAKIQDKEGIPPDQQRLIWAGK
QLEDGRTLSDYNILRTGPLHLVLRLRGG

FIGURE 15 E. Concentration-dependent ELISA determines the high affinity binding of Kd 1,7 nM to TNF-alpha.

FIGURE 16. NGF binding of modified ubiquitin-based heterodimers

Figure A. Sequence of the heterodimeric ubiquitin binding protein SPWF-9_1-B7_th with specificity for NGF. Modifications are in positions 2, 4, 6, 62-66 and in position 51 of the first ubiquitin monomer and in positions 6, 8, 62-66 in the second monomer. Linker between the two ubiquitin monomers: SGGGGSGGGGIG.

SPWF-9_1-B7_th

MMISVYTLTGKTITLEVEPSDTIENVKAKIQDKEGIPPDQQRLIWAGKQLDDGRTLSDYNIRSRGLLH
LVLRLRGGSGGGGSGGGGIGMQIFVLTHTGKTITLEVEPSDTIENVKAKIQDKEGIPPDQQRLIWAGK
QLEDGRTLSDYNISHSRTLHLVLRLRGG

Figure B. Concentration-dependent ELISA determines an affinity of Kd 0.9 µM to NGF

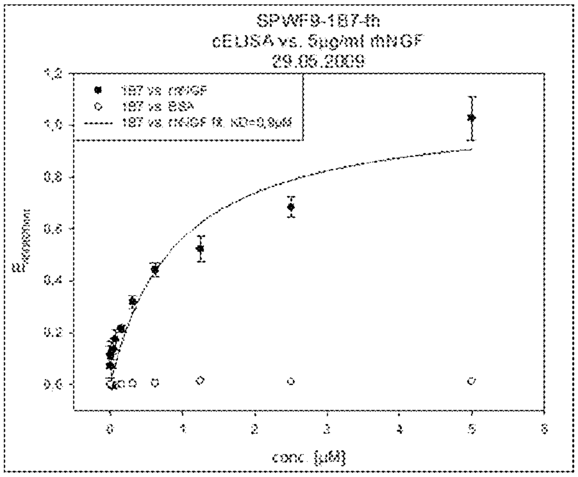

Figure C. Sequence of the heterodimeric ubiquitin binding protein SPWF-9_6-A2_th with specificity for NGF. Modifications are in positions 2, 4, 6, 62-66 of the first ubiquitin monomer and in positions 6, 8, 62-66 in the second monomer. Linker between the two ubiquitin monomers: SGGGGSGGGGIG.

SPWF-9_6-A2_th

MAIVVYTLTGKTITLEVEPSDTIENVSAKIQDKEGIPPDQQRLIWAGKQLEDGRTLSDYNIPMPVLLH
LVLRLRGGSGGGGSGGGGIGMQIFVNTSTGKTITLEVEPSDTIENVKAKIQDKEGIPPDQQRLIWAGK
QLEDGRTLSDYNIDQQRILHLVLRLRGG

Figure D. Concentration-dependent ELISA determines an affinity of Kd 180 nM to NGF The Kd was difficult to determine since the signal decreased at high concentrations.

FIGURE 17 Heterodimeric IgG binding proteins.

Figure A. Sequence of the heterodimeric ubiquitin binding protein SPVF-4_16-B2_ts with specificity for IgG. Modifications are in positions 6, 8, 62-66 of the first ubiquitin monomer and in positions 6, 8, 62-66 in the second monomer. Linker between the two ubiquitin monomers: SGGGGSGGGGIG.

SPVF-4_16-B2_ts

MQIFVDTLTGKTITLEVEPSDTIENVKAKIQDKEGIPPDQQRLIWAGKQLEDGRTLSDYNILIEWLLH
LVLRLRGGSGGGGSGGGGIGMQIFVDTLTGKTITLEVEPSDTIENVKAKIQDKEGIPPDQQRLIWAGK
QLEDGRTLSDYNIGADAPLHLVLRLRGG

Figure B. Concentration-dependent ELISA determines an affinity of Kd 3.8 μM to IgG

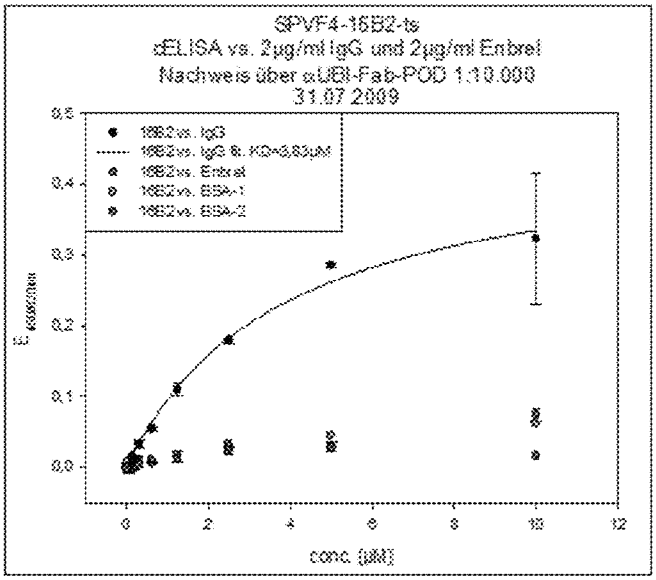

Figure C. Sequence of the heterodimeric ubiquitin binding protein SPVF-4_9-C6_ts with specificity for IgG. Modifications are in positions 6, 8, 62-66 of the first ubiquitin monomer and in positions 6, 8, 62-66 in the second monomer. Linker between the two ubiquitin monomers: SGGGGSGGGGIG.

SPVF-4_9-C6_ts

MQIFVDTDTGKTITLEVEPSDTIENVKAKIQDKEGIPPDQQRLIWAGKQLEDGRTLSDYNITFNPQLH
LVLRLRGGSGGGGSGGGGIGMQIFVWTTTGKTITLEVEPSDTIENVKAKIQDKEGIPPDQQRLIWAGK
QLEDGRTLSDYNIPHWRILHLVLRLRGG

Figure D. Concentration-dependent ELISA determines an affinity of Kd 4.1 µM to IgG

SEQUENCE LISTING

<160> NUMBER OF SEQ ID NOS: 96

<210> SEQ ID NO 1
<211> LENGTH: 76
<212> TYPE: PRT
<213> ORGANISM: artificial
<220> FEATURE:
<223> OTHER INFORMATION: Ubiquitin protein

<400> SEQUENCE: 1

Met Gln Ile Phe Val Lys Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Gln Lys Glu
50 55 60

Ser Thr Leu His Leu Val Leu Arg Leu Arg Gly Gly
65 70 75

<210> SEQ ID NO 2
<211> LENGTH: 91
<212> TYPE: PRT
<213> ORGANISM: artificial
<220> FEATURE:
<223> OTHER INFORMATION: ED-B domain of oncofetal fibronectin

<400> SEQUENCE: 2

Glu Val Pro Gln Leu Thr Asp Leu Ser Phe Val Asp Ile Thr Asp Ser
1 5 10 15

Ser Ile Gly Leu Arg Trp Thr Pro Leu Asn Ser Ser Thr Ile Ile Gly
20 25 30

Tyr Arg Ile Thr Val Val Ala Ala Gly Glu Gly Ile Pro Ile Phe Glu
35 40 45

Asp Phe Val Asp Ser Ser Val Gly Tyr Tyr Thr Val Thr Gly Leu Glu
50 55 60

Pro Gly Ile Asp Tyr Asp Ile Ser Val Ile Thr Leu Ile Asn Gly Gly
65 70 75 80

Glu Ser Ala Pro Thr Thr Leu Thr Gln Gln Thr
85 90

<210> SEQ ID NO 3
<211> LENGTH: 76
<212> TYPE: PRT
<213> ORGANISM: artificial
<220> FEATURE:
<223> OTHER INFORMATION: Ubiquitin variant 1H4

<400> SEQUENCE: 3

Met Trp Ile Lys Val His Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Thr Leu Ser
50 55 60

Arg Ser Leu His Leu Val Leu Arg Leu Arg Gly Gly 65 70 75

<210> SEQ ID NO 4
<211> LENGTH: 76
<212> TYPE: PRT
<213> ORGANISM: artificial
<220> FEATURE:
<223> OTHER INFORMATION: Ubiquitin variant 4B10

<400> SEQUENCE: 4

Met Leu Ile Leu Val Leu Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Ala Thr Lys
50 55 60

Pro Ile Leu His Leu Val Leu Arg Leu Arg Gly Gly
65 70 75

<210> SEQ ID NO 5
<211> LENGTH: 76
<212> TYPE: PRT
<213> ORGANISM: artificial
<220> FEATURE:
<223> OTHER INFORMATION: Ubiquitin variant 5E1

<400> SEQUENCE: 5

Met Val Ile Asn Val Phe Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Arg Ser Thr
50 55 60

Ser Lys Leu His Leu Val Leu Arg Leu Arg Gly Gly
65 70 75

<210> SEQ ID NO 6
<211> LENGTH: 164
<212> TYPE: PRT
<213> ORGANISM: artificial
<220> FEATURE:
<223> OTHER INFORMATION: Ubiquitin dimer 46H9

<400> SEQUENCE: 6

Met Gly Ile Val Val Arg Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Pro His Pro
50 55 60

Thr Leu Leu His Leu Val Leu Arg Leu Arg Gly Gly Ser Gly Gly Gly
65 70 75 80

Gly Ser Gly Gly Gly Gly Ile Gly Met Gln Ile Phe Val His Thr Met
85 90 95

```
Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Lys Pro Ile Ala Glu Leu His Leu Val Leu Arg
145                 150                 155                 160

Leu Arg Gly Gly


<210> SEQ ID NO 7
<211> LENGTH: 164
<212> TYPE: PRT
<213> ORGANISM: artificial
<220> FEATURE:
<223> OTHER INFORMATION: Ubiquitin dimer 9E12

<400> SEQUENCE: 7

Met Arg Ile Pro Val Tyr Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro Pro Phe
    50                  55                  60

Ala Arg Leu His Leu Val Leu Arg Leu Arg Gly Gly Ser Gly Gly Gly
65                  70                  75                  80

Gly Ser Gly Gly Gly Gly Ile Gly Met Gln Ile Phe Val Met Thr Arg
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Met Asn Ala Arg Leu Leu His Leu Val Leu Arg
145                 150                 155                 160

Leu Arg Gly Gly


<210> SEQ ID NO 8
<211> LENGTH: 164
<212> TYPE: PRT
<213> ORGANISM: artificial
<220> FEATURE:
<223> OTHER INFORMATION: Ubiquitin dimer 22D1

<400> SEQUENCE: 8

Met Leu Ile Leu Val Arg Thr Leu Thr Asp Lys Thr Ile Thr Leu Glu
1               5                   10                  15

Val Glu Pro Ser Asp Thr Ile Gly Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Ser Val Gly
    50                  55                  60

Ala Met Leu His Leu Val Leu Arg Leu Arg Gly Gly Ser Gly Gly Gly
65                  70                  75                  80
```

-continued

```
Gly Ser Gly Gly Gly Gly Ile Gly Met Gln Ile Phe Val Leu Thr Trp
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Arg Arg Leu Pro Pro Leu His Leu Val Leu Arg
145                 150                 155                 160

Leu Arg Gly Gly


<210> SEQ ID NO 9
<211> LENGTH: 65
<212> TYPE: DNA
<213> ORGANISM: artificial
<220> FEATURE:
<223> OTHER INFORMATION: Primer F1

<400> SEQUENCE: 9

ggagaccaca acggtttccc tctagaaata attttgttta actttaagaa ggagatatac     60

atatg                                                                 65


<210> SEQ ID NO 10
<211> LENGTH: 39
<212> TYPE: DNA
<213> ORGANISM: artificial
<220> FEATURE:
<223> OTHER INFORMATION: Primer WUBI(co)RD_xho

<400> SEQUENCE: 10

aaaaaaaaac tcgagaccgc cacgcagacg cagaaccag                            39


<210> SEQ ID NO 11
<211> LENGTH: 834
<212> TYPE: DNA
<213> ORGANISM: artificial
<220> FEATURE:
<223> OTHER INFORMATION: Construct His6-SUMO-TNFa

<400> SEQUENCE: 11

atgggcagca gccatcatca tcatcatcac ggcagcggcc tggtgccgcg cggcagcgct     60

agcatgtcgg actcagaagt caatcaagaa gctaagccag aggtcaagcc agaagtcaag    120

cctgagactc acatcaattt aaaggtgtcc gatggatctt cagagatctt cttcaagatc    180

aaaaagacca ctcctttaag aaggctgatg gaagcgttcg ctaaaagaca gggtaaggaa    240

atggactcct taagattctt gtacgacggt attagaattc aagctgatca gacccctgaa    300

gatttggaca tggaggataa cgatattatt gaggctcaca gagaacagat tggtggtgtg    360

cgtagcagca gccgtacccc gagcgataaa ccggtggcgc atgtggtggc gaatccgcag    420

gcggaaggcc agctgcagtg gctgaaccgt cgtgcgaatg cgctgctggc caacggcgtg    480

gaactgcgtg ataatcagct ggttgtgccg agcgaaggcc tgtatctgat ttatagccag    540

gtgctgttta aaggccaggg ctgcccgagc acccatgtgc tgctgaccca taccattagc    600

cgtattgcgg tgagctatca gaccaaagtg aacctgctgt ctgcgattaa aagcccgtgc    660

cagcgtgaaa ccccggaagg cgcggaagcg aaaccgtggt atgaaccgat ttatctgggc    720

ggcgtgtttc agctggaaaa aggcgatcgt ctgagcgcgg aaattaaccg tccggattat    780
```

ctggattttg cggaaagcgg ccaggtgtat tttggcatta ttgcgctgta ataa 834

<210> SEQ ID NO 12
<211> LENGTH: 27
<212> TYPE: DNA
<213> ORGANISM: artificial
<220> FEATURE:
<223> OTHER INFORMATION: Primer SUMO-EDB-TNFa-fw

<400> SEQUENCE: 12 tttttggat ccgtgcgtag cagcagc 27

<210> SEQ ID NO 13
<211> LENGTH: 28
<212> TYPE: DNA
<213> ORGANISM: artificial
<220> FEATURE:
<223> OTHER INFORMATION: Primer SUMO-EDB-TNFa-rev

<400> SEQUENCE: 13
cttgtctctc gaggcggccg cttattac 28

<210> SEQ ID NO 14
<211> LENGTH: 33
<212> TYPE: DNA
<213> ORGANISM: artificial
<220> FEATURE:
<223> OTHER INFORMATION: Primer SUMO-EDB-WUBI-fw

<400> SEQUENCE: 14
gttccaaggt ctcatggtat gcagatcttc gtg 33

<210> SEQ ID NO 15
<211> LENGTH: 42
<212> TYPE: DNA
<213> ORGANISM: artificial
<220> FEATURE:
<223> OTHER INFORMATION: Primer SUMO-EDB-Linker-rev

<400> SEQUENCE: 15
gtggtgggat ccaccgccac caccagaacc gccacgcaga cg 42

<210> SEQ ID NO 16
<211> LENGTH: 33
<212> TYPE: DNA
<213> ORGANISM: artificial
<220> FEATURE:
<223> OTHER INFORMATION: Primer SUMO-EDB-1H4-fw

<400> SEQUENCE: 16
gttccaaggt ctcatggtat gtggatcaag gtg 33

<210> SEQ ID NO 17
<211> LENGTH: 33
<212> TYPE: DNA
<213> ORGANISM: artificial
<220> FEATURE:
<223> OTHER INFORMATION: Primer SUMO-EDB-4B10-fw

<400> SEQUENCE: 17
gttccaaggt ctcatggtat gttgatcctg gtg 33

<210> SEQ ID NO 18
<211> LENGTH: 33
<212> TYPE: DNA
<213> ORGANISM: artificial
<220> FEATURE:

<223> OTHER INFORMATION: Primer SUMO-EDB-5E1-fw

<400> SEQUENCE: 18
gttccaaggt ctcatggtat ggttatcaat gtg 33

<210> SEQ ID NO 19
<211> LENGTH: 42
<212> TYPE: DNA
<213> ORGANISM: artificial
<220> FEATURE:
<223> OTHER INFORMATION: Primer Dimer-t0a-rev

<400> SEQUENCE: 19
gtggtgggat ccaccgccac caccagaacc accacgtaaa cg 42

<210> SEQ ID NO 20
<211> LENGTH: 33
<212> TYPE: DNA
<213> ORGANISM: artificial
<220> FEATURE:
<223> OTHER INFORMATION: Primer SUMO-EDB-WUBI-fw

<400> SEQUENCE: 20
gttccaaggt ctcatggtat gcagatcttc gtg 33

<210> SEQ ID NO 21
<211> LENGTH: 33
<212> TYPE: DNA
<213> ORGANISM: artificial
<220> FEATURE:
<223> OTHER INFORMATION: Primer 9E12-t0a-fw

<400> SEQUENCE: 21
gttccaaggt ctcatggtat gcgtatccct gtg 33

<210> SEQ ID NO 22
<211> LENGTH: 33
<212> TYPE: DNA
<213> ORGANISM: artificial
<220> FEATURE:
<223> OTHER INFORMATION: Primer 24H12-t0a-fw

<400> SEQUENCE: 22
gttccaaggt ctcatggtat ggttatcaag gtg 33

<210> SEQ ID NO 23
<211> LENGTH: 33
<212> TYPE: DNA
<213> ORGANISM: artificial
<220> FEATURE:
<223> OTHER INFORMATION: Primer 15G7-t0a-fw

<400> SEQUENCE: 23
gttccaaggt ctcatggtat ggagatcggt gtg 33

<210> SEQ ID NO 24
<211> LENGTH: 33
<212> TYPE: DNA
<213> ORGANISM: artificial
<220> FEATURE:
<223> OTHER INFORMATION: Primer 22D1-t0a-fw

<400> SEQUENCE: 24
gttccaaggt ctcatggtat gcttatcttg gtg 33

<210> SEQ ID NO 25

-continued

```
<211> LENGTH: 164
<212> TYPE: PRT
<213> ORGANISM: artificial
<220> FEATURE:
<223> OTHER INFORMATION: Variant 46-H4

<400> SEQUENCE: 25

Met Gly Ile Val Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro His Pro
    50                  55                  60

Thr Leu Leu His Leu Val Leu Arg Leu Arg Gly Gly Ser Gly Gly Gly
65                  70                  75                  80

Gly Ser Gly Gly Gly Gly Ile Gly Met Gln Ile Phe Val Gly Thr Trp
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Thr Gln Ala Thr Arg Leu His Leu Val Leu Arg
145                 150                 155                 160

Leu Arg Gly Gly


<210> SEQ ID NO 26
<211> LENGTH: 164
<212> TYPE: PRT
<213> ORGANISM: artificial
<220> FEATURE:
<223> OTHER INFORMATION: Variant 45-H9

<400> SEQUENCE: 26

Met Arg Ile Pro Val Tyr Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro Pro Phe
    50                  55                  60

Ala Arg Leu His Leu Val Leu Arg Leu Arg Gly Gly Ser Gly Gly Gly
65                  70                  75                  80

Gly Ser Gly Gly Gly Gly Ile Gly Met Gln Ile Phe Val Leu Thr Met
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Leu Ala Phe Ala Thr Leu His Leu Val Leu Arg
145                 150                 155                 160
```

Leu Arg Gly Gly

<210> SEQ ID NO 27
<211> LENGTH: 164
<212> TYPE: PRT
<213> ORGANISM: artificial
<220> FEATURE:
<223> OTHER INFORMATION: Variant 46-A5

<400> SEQUENCE: 27

```
Met Gly Ile Val Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro His Pro
    50                  55                  60

Thr Leu Leu His Leu Val Leu Arg Leu Arg Gly Gly Ser Gly Gly Gly
65                  70                  75                  80

Gly Ser Gly Gly Gly Gly Ile Gly Met Gln Ile Phe Val Leu Thr Met
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Leu Ala Phe Ala Thr Leu His Leu Val Leu Arg
145                 150                 155                 160

Leu Arg Gly Gly
```

<210> SEQ ID NO 28
<211> LENGTH: 164
<212> TYPE: PRT
<213> ORGANISM: artificial
<220> FEATURE:
<223> OTHER INFORMATION: Variant 50-G11

<400> SEQUENCE: 28

```
Met Gly Ile Val Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro His Pro
    50                  55                  60

Thr Leu Leu His Leu Val Leu Arg Leu Arg Gly Gly Ser Gly Gly Gly
65                  70                  75                  80

Gly Ser Gly Gly Gly Gly Ile Gly Met Gln Ile Phe Val Met Thr Arg
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140
```

-continued

```
Ser Asp Tyr Asn Ile Met Asn Ala Arg Leu Leu His Leu Val Leu Arg
145                 150                 155                 160

Leu Arg Gly Gly


<210> SEQ ID NO 29
<211> LENGTH: 164
<212> TYPE: PRT
<213> ORGANISM: artificial
<220> FEATURE:
<223> OTHER INFORMATION: Variant 52-B3

<400> SEQUENCE: 29

Met Arg Ile Pro Val Tyr Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro Pro Phe
    50                  55                  60

Ala Arg Leu His Leu Val Leu Arg Leu Arg Gly Gly Ser Gly Gly Gly
65                  70                  75                  80

Gly Ser Gly Gly Gly Gly Ile Gly Met Gln Ile Phe Val His Thr Met
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Lys Pro Ile Ala Glu Leu His Leu Val Leu Arg
145                 150                 155                 160

Leu Arg Gly Gly


<210> SEQ ID NO 30
<211> LENGTH: 164
<212> TYPE: PRT
<213> ORGANISM: artificial
<220> FEATURE:
<223> OTHER INFORMATION: Variant 52-D10

<400> SEQUENCE: 30

Met Val Ile Cys Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Thr Ala Pro
    50                  55                  60

Gly Asp Leu His Leu Val Leu Arg Leu Arg Gly Gly Ser Gly Gly Gly
65                  70                  75                  80

Gly Ser Gly Gly Gly Gly Ile Gly Met Gln Ile Phe Val His Thr Met
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
```

```
        115                 120                 125

Gln Arg Leu Ile Trp Ala Gly Lys Gln Leu Glu Asp Gly Arg Thr Leu
    130                 135                 140

Ser Asp Tyr Asn Ile Lys Pro Ile Ala Glu Leu His Leu Val Leu Arg
145                 150                 155                 160

Leu Arg Gly Gly


<210> SEQ ID NO 31
<211> LENGTH: 8
<212> TYPE: PRT
<213> ORGANISM: artificial
<220> FEATURE:
<223> OTHER INFORMATION: His-Tag

<400> SEQUENCE: 31

Leu Glu His His His His His His
1               5


<210> SEQ ID NO 32
<211> LENGTH: 12
<212> TYPE: PRT
<213> ORGANISM: artificial
<220> FEATURE:
<223> OTHER INFORMATION: Glycine/serine linker

<400> SEQUENCE: 32

Ser Gly Gly Gly Gly Ser Gly Gly Gly Gly Ile Gly
1               5                   10


<210> SEQ ID NO 33
<211> LENGTH: 155
<212> TYPE: PRT
<213> ORGANISM: artificial
<220> FEATURE:
<223> OTHER INFORMATION: Ubiquitin dimer SPVF-28_1041-D11_TsX9

<400> SEQUENCE: 33

Met Gln Ile Phe Val Trp Thr Trp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Arg Lys
    50                  55                  60

Phe Pro Leu His Leu Val Leu Arg Leu Arg Gly Gly Gly Ile Gly Met
65                  70                  75                  80

Arg Ile Phe Val Thr Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Trp Ser Asn Trp
    130                 135                 140

Glu Leu His Leu Val Leu Arg Leu Arg Ala Ala
145                 150                 155


<210> SEQ ID NO 34
<211> LENGTH: 155
<212> TYPE: PRT
```

<213> ORGANISM: artificial
<220> FEATURE:
<223> OTHER INFORMATION: Ubiquitin dimer SPVF-28_1045-D10_TsX9

<400> SEQUENCE: 34

Met Gln Ile Phe Val Trp Thr Trp Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Gln Arg Lys
50 55 60

Phe Pro Leu His Leu Val Leu Arg Leu Arg Gly Gly Gly Ile Gly Met
65 70 75 80

Gln Ile Phe Val Thr Thr Gln Thr Gly Lys Thr Ile Thr Leu Glu Val
85 90 95

Glu Pro Ser Asp Thr Ile Glu Asn Val Lys Ala Lys Ile Gln Asp Lys
100 105 110

Glu Gly Ile Pro Pro Asp Gln Gln Arg Leu Ile Trp Ala Gly Lys Gln
115 120 125

Leu Glu Asp Gly Arg Thr Leu Ser Asp Tyr Asn Ile Trp Ser Asn Trp
130 135 140

Glu Leu His Leu Val Leu Arg Leu Arg Ala Ala
145 150 155

<210> SEQ ID NO 35
<211> LENGTH: 319
<212> TYPE: PRT
<213> ORGANISM: artificial
<220> FEATURE:
<223> OTHER INFORMATION: fusion protein SPVF-28_1041-D11_T0aX9

<400> SEQUENCE: 35

Met Gln Ile Phe Val Trp Thr Trp Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Gln Arg Lys
50 55 60

Phe Pro Leu His Leu Val Leu Arg Leu Arg Gly Gly Gly Ile Gly Met
65 70 75 80

Arg Ile Phe Val Thr Thr Gln Thr Gly Lys Thr Ile Thr Leu Glu Val
85 90 95

Glu Pro Ser Asp Thr Ile Glu Asn Val Lys Ala Lys Ile Gln Asp Lys
100 105 110

Glu Gly Ile Pro Pro Asp Gln Gln Arg Leu Ile Trp Ala Gly Lys Gln
115 120 125

Leu Glu Asp Gly Arg Thr Leu Ser Asp Tyr Asn Ile Trp Ser Asn Trp
130 135 140

Glu Leu His Leu Val Leu Arg Leu Arg Ala Ala Ser Gly Gly Gly Gly
145 150 155 160

Gly Ser Val Arg Ser Ser Ser Arg Thr Pro Ser Asp Lys Pro Val Ala
165 170 175

His Val Val Ala Asn Pro Gln Ala Glu Gly Gln Leu Gln Trp Leu Asn

```
            180                 185                 190

Arg Arg Ala Asn Ala Leu Leu Ala Asn Gly Val Glu Leu Arg Asp Asn
        195                 200                 205

Gln Leu Val Val Pro Ser Glu Gly Leu Tyr Leu Ile Tyr Ser Gln Val
    210                 215                 220

Leu Phe Lys Gly Gln Gly Cys Pro Ser Thr His Val Leu Leu Thr His
225                 230                 235                 240

Thr Ile Ser Arg Ile Ala Val Ser Tyr Gln Thr Lys Val Asn Leu Leu
                245                 250                 255

Ser Ala Ile Lys Ser Pro Cys Gln Arg Glu Thr Pro Glu Gly Ala Glu
            260                 265                 270

Ala Lys Pro Trp Tyr Glu Pro Ile Tyr Leu Gly Gly Val Phe Gln Leu
        275                 280                 285

Glu Lys Gly Asp Arg Leu Ser Ala Glu Ile Asn Arg Pro Asp Tyr Leu
    290                 295                 300

Asp Phe Ala Glu Ser Gly Gln Val Tyr Phe Gly Ile Ile Ala Leu
305                 310                 315


<210> SEQ ID NO 36
<211> LENGTH: 318
<212> TYPE: PRT
<213> ORGANISM: artificial
<220> FEATURE:
<223> OTHER INFORMATION: fusion protein SPVF-28_1041-D11_T0uX9

<400> SEQUENCE: 36

Met Gln Ile Phe Val Trp Thr Trp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Arg Lys
    50                  55                  60

Phe Pro Leu His Leu Val Leu Arg Leu Arg Gly Gly Gly Ile Gly Met
65                  70                  75                  80

Arg Ile Phe Val Thr Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Trp Ser Asn Trp
    130                 135                 140

Glu Leu His Leu Val Leu Arg Leu Arg Ala Ala Ser Gly Gly Gly Gly
145                 150                 155                 160

Gly Ser Leu Arg Ser Ser Ser Gln Asn Ser Ser Asp Lys Pro Val Ala
                165                 170                 175

His Val Val Ala Asn His Gln Val Glu Glu Gln Leu Glu Trp Leu Ser
            180                 185                 190

Gln Arg Ala Asn Ala Leu Leu Ala Asn Gly Met Asp Leu Lys Asp Asn
        195                 200                 205

Gln Leu Val Val Pro Ala Asp Gly Leu Tyr Leu Val Tyr Ser Gln Val
    210                 215                 220

Leu Phe Lys Gly Gln Gly Cys Pro Asp Tyr Val Leu Leu Thr His Thr
225                 230                 235                 240
```

-continued

Val Ser Arg Phe Ala Ile Ser Tyr Gln Glu Lys Val Asn Leu Leu Ser
245 250 255

Ala Val Lys Ser Pro Cys Pro Lys Asp Thr Pro Glu Gly Ala Glu Leu
260 265 270

Lys Pro Trp Tyr Glu Pro Ile Tyr Leu Gly Gly Val Phe Gln Leu Glu
275 280 285

Lys Gly Asp Gln Leu Ser Ala Glu Val Asn Leu Pro Lys Tyr Leu Asp
290 295 300

Phe Ala Glu Ser Gly Gln Val Tyr Phe Gly Val Ile Ala Leu
305 310 315

<210> SEQ ID NO 37
<211> LENGTH: 155
<212> TYPE: PRT
<213> ORGANISM: artificial
<220> FEATURE:
<223> OTHER INFORMATION: Ubiquitin dimer SPVF-28_1048-E10_TsX9

<400> SEQUENCE: 37

Met Gln Ile Phe Val Trp Thr His Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly His Thr Leu Ser Asp Tyr Asn Ile Pro Arg Arg
50 55 60

Ser Trp Leu His Leu Val Leu Arg Leu Arg Gly Gly Gly Ile Gly Met
65 70 75 80

Gln Ile Phe Val Ser Thr Thr Thr Gly Glu Thr Ile Thr Leu Glu Val
85 90 95

Glu Pro Ser Asp Thr Ile Glu Asn Val Lys Ala Lys Ile Gln Asp Lys
100 105 110

Glu Gly Ile Pro Pro Asp Gln Gln Arg Leu Ile Trp Ala Gly Lys Gln
115 120 125

Leu Glu Asp Gly Arg Thr Leu Ser Asp Tyr Asn Ile Ala Asp Pro Arg
130 135 140

Trp Leu His Leu Val Leu Arg Leu Arg Ala Ala
145 150 155

<210> SEQ ID NO 38
<211> LENGTH: 155
<212> TYPE: PRT
<213> ORGANISM: artificial
<220> FEATURE:
<223> OTHER INFORMATION: Ubiquitin dimer SPVF-28_1041-E6_TsX9

<400> SEQUENCE: 38

Met Gln Ile Phe Val Trp Thr His Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Pro Arg Arg
50 55 60

Ser Trp Leu His Leu Val Leu Arg Leu Arg Gly Gly Gly Ile Gly Met
65 70 75 80

-continued

```
Gln Ile Phe Val Ser Thr Thr Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Arg
        115                 120                 125

Leu Glu Asp Gly Arg Thr Leu Ser Asp Tyr Asn Ile Ala Asp Pro Arg
    130                 135                 140

Trp Leu His Leu Val Leu Arg Leu Arg Ala Ala
145                 150                 155


<210> SEQ ID NO 39
<211> LENGTH: 155
<212> TYPE: PRT
<213> ORGANISM: artificial
<220> FEATURE:
<223> OTHER INFORMATION: Ubiquitin dimer SPVF-28_1041-H10_TsX9

<400> SEQUENCE: 39

Met Gln Ile Phe Val Trp Thr Asn Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Glu His Gly
    50                  55                  60

Lys Trp Leu His Leu Val Leu Arg Leu Arg Gly Gly Gly Ile Gly Met
65                  70                  75                  80

Gln Ile Phe Val Asn Thr Thr Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Phe Ile Gly His
    130                 135                 140

Trp Leu His Leu Val Leu Arg Leu Arg Ala Ala
145                 150                 155


<210> SEQ ID NO 40
<211> LENGTH: 158
<212> TYPE: PRT
<213> ORGANISM: artificial
<220> FEATURE:
<223> OTHER INFORMATION: Ubiquitin dimer SPVF-28_1056-B6_TsX6

<400> SEQUENCE: 40

Met Gln Ile Phe Val His Thr His Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asn Arg Asp
    50                  55                  60

Lys Arg Leu His Leu Val Leu Arg Leu Arg Ala Ala Ser Gly Gly Gly
65                  70                  75                  80
```

-continued

```
Gly Ile Gly Met Gln Ile Phe Val Asn Thr Asn Thr Gly Glu Thr Ile
                85                  90                  95

Thr Leu Glu Val Glu Pro Ser Asp Thr Ile Glu Asn Val Lys Ala Lys
            100                 105                 110

Ile Gln Asp Lys Glu Gly Ile Pro Pro Asp Gln Gln Arg Leu Ile Trp
        115                 120                 125

Ala Gly Lys Arg Leu Glu Asp Gly Arg Thr Leu Ser Asp Tyr Asn Ile
    130                 135                 140

Asp Trp Arg Trp Leu His Leu Val Leu Arg Leu Arg Ala Ala
145                 150                 155


<210> SEQ ID NO 41
<211> LENGTH: 154
<212> TYPE: PRT
<213> ORGANISM: artificial
<220> FEATURE:
<223> OTHER INFORMATION: Ubiquitin dimer SPVF-28_1051-B7_TsX9

<400> SEQUENCE: 41

Met Gln Ile Phe Val His Thr Thr Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Thr Leu Thr
    50                  55                  60

Pro Thr Leu His Leu Val Leu Arg Leu Arg Gly Gly Gly Ile Gly Met
65                  70                  75                  80

Gln Ile Phe Val Leu Thr Leu Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Asp Trp Arg Trp
    130                 135                 140

Leu His Leu Val Leu Arg Leu Arg Ala Ala
145                 150


<210> SEQ ID NO 42
<211> LENGTH: 155
<212> TYPE: PRT
<213> ORGANISM: artificial
<220> FEATURE:
<223> OTHER INFORMATION: Ubiquitin dimer SPVF-28_1035-E6_TsX9

<400> SEQUENCE: 42

Met Gln Ile Phe Val His Thr Phe Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile His Glu Arg
    50                  55                  60

Glu Ile Leu His Leu Val Leu Arg Leu Arg Gly Gly Gly Ile Gly Met
65                  70                  75                  80
```

Gln Ile Phe Val Ser Thr Pro Thr Gly Lys Thr Ile Thr Leu Glu Val
85 90 95

Glu Pro Ser Asp Thr Ile Glu Asn Val Lys Ala Lys Ile Gln Asp Lys
100 105 110

Glu Gly Ile Pro Pro Asp Gln Gln Arg Leu Ile Trp Ala Gly Lys Gln
115 120 125

Leu Glu Asp Gly Arg Thr Leu Ser Asp Tyr Asn Ile Gly Val Glu Met
130 135 140

Leu Leu His Leu Val Leu Arg Leu Arg Ala Ala
145 150 155

<210> SEQ ID NO 43
<211> LENGTH: 154
<212> TYPE: PRT
<213> ORGANISM: artificial
<220> FEATURE:
<223> OTHER INFORMATION: Ubiquitin dimer SPVF-28_1049-D4_TsX9

<400> SEQUENCE: 43

Met Gln Ile Phe Val His Thr Asp Thr Gly Lys Thr Ile Thr Leu Glu
1 5 10 15

Val Glu Pro Ser Asp Thr Ile Glu Asn Val Lys Ala Glu Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile His Asn Trp
50 55 60

Arg Asn Leu His Leu Val Leu Arg Leu Arg Gly Gly Gly Ile Gly Met
65 70 75 80

Gln Ile Phe Val Ile Thr Ile Thr Gly Lys Thr Ile Thr Leu Glu Val
85 90 95

Glu Pro Ser Asp Thr Ile Glu Asn Val Lys Ala Lys Ile Gln Asp Lys
100 105 110

Glu Gly Ile Pro Pro Asp Gln Gln Arg Leu Ile Trp Ala Gly Lys Gln
115 120 125

Leu Lys Asp Gly Arg Thr Leu Ser Asp Tyr Asn Ile Asp Trp Arg Trp
130 135 140

Leu His Leu Val Leu Arg Leu Arg Ala Ala
145 150

<210> SEQ ID NO 44
<211> LENGTH: 164
<212> TYPE: PRT
<213> ORGANISM: artificial
<220> FEATURE:
<223> OTHER INFORMATION: Ubiquitin dimer SPWF-28_1071-C8_TsX2

<400> SEQUENCE: 44

Met Trp Ile Arg Val Pro Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile His Met Pro
50 55 60

Asp Ile Leu His Leu Val Leu Arg Leu Arg Gly Gly Ser Gly Gly Gly
65 70 75 80

Gly Ser Gly Gly Gly Gly Ile Gly Met Gln Ile Phe Val Trp Thr Met
85 90 95

Thr Gly Lys Thr Ile Thr Leu Glu Val Glu Pro Ser Asp Thr Ile Glu
100 105 110

Asn Val Lys Ala Lys Ile Gln Asp Lys Glu Gly Ile Pro Pro Asp Gln
115 120 125

Gln Arg Leu Ile Trp Ala Gly Lys Gln Leu Glu Asp Gly Arg Thr Leu
130 135 140

Ser Asp Tyr Asn Ile His Leu His Met Arg Leu His Leu Val Leu Arg
145 150 155 160

Leu Arg Gly Gly

<210> SEQ ID NO 45
<211> LENGTH: 164
<212> TYPE: PRT
<213> ORGANISM: artificial
<220> FEATURE:
<223> OTHER INFORMATION: Ubiquitin dimer SPWF-28_1071-C12_TsX2

<400> SEQUENCE: 45

Met Thr Ile Trp Val His Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Asn Phe Lys
50 55 60

Leu Ser Leu His Leu Val Leu Arg Leu Arg Gly Gly Ser Gly Gly Gly
65 70 75 80

Gly Ser Gly Gly Gly Gly Ile Gly Met Gln Ile Phe Val Ser Thr Phe
85 90 95

Thr Gly Lys Thr Ile Thr Leu Glu Val Glu Pro Ser Asp Thr Ile Glu
100 105 110

Asn Val Lys Ala Lys Ile Gln Asp Lys Glu Gly Ile Pro Pro Asp Gln
115 120 125

Gln Arg Leu Ile Trp Ala Gly Lys Gln Leu Glu Asp Gly Arg Thr Leu
130 135 140

Ser Asp Tyr Asn Ile His Tyr Leu Pro Lys Leu His Leu Val Leu Arg
145 150 155 160

Leu Arg Gly Gly

<210> SEQ ID NO 46
<211> LENGTH: 172
<212> TYPE: PRT
<213> ORGANISM: artificial
<220> FEATURE:
<223> OTHER INFORMATION: Ubiquitin dimer SPWF-28_1071-H7_TsX2

<400> SEQUENCE: 46

Met Trp Ile Arg Val Pro Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Arg Arg Val

```
    50                  55                  60

Asn Tyr Leu His Leu Val Leu Arg Leu Arg Gly Gly Ser Gly Gly Gly
65                  70                  75                  80

Gly Ser Gly Gly Gly Gly Ile Gly Met Gln Ile Phe Val Trp Thr Ser
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Tyr Thr Tyr Met Arg Leu His Leu Val Leu Arg
145                 150                 155                 160

Leu Arg Gly Gly Leu Glu His His His His His His
                165                 170


<210> SEQ ID NO 47
<211> LENGTH: 164
<212> TYPE: PRT
<213> ORGANISM: artificial
<220> FEATURE:
<223> OTHER INFORMATION: Ubiquitin dimer with linker SGGGGSGGGGIG
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (150)..(154)
<223> OTHER INFORMATION: Xaa can be any naturally occurring amino acid

<400> SEQUENCE: 47

Met Thr Ile Trp Val His Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asn Phe Lys
    50                  55                  60

Leu Ser Leu His Leu Val Leu Arg Leu Arg Gly Gly Ser Gly Gly Gly
65                  70                  75                  80

Gly Ser Gly Gly Gly Gly Ile Gly Met Gln Ile Phe Val Xaa Thr Xaa
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Xaa Xaa Xaa Xaa Xaa Leu His Leu Val Leu Arg
145                 150                 155                 160

Leu Arg Gly Gly


<210> SEQ ID NO 48
<211> LENGTH: 5
```

<212> TYPE: PRT
<213> ORGANISM: artificial
<220> FEATURE:
<223> OTHER INFORMATION: Glycine/serine linker

<400> SEQUENCE: 48

Ser Gly Gly Gly Gly
1 5

<210> SEQ ID NO 49
<211> LENGTH: 7
<212> TYPE: PRT
<213> ORGANISM: artificial
<220> FEATURE:
<223> OTHER INFORMATION: Glycine/serine linker

<400> SEQUENCE: 49

Ser Gly Gly Gly Gly Ile Gly
1 5

<210> SEQ ID NO 50
<211> LENGTH: 10
<212> TYPE: PRT
<213> ORGANISM: artificial
<220> FEATURE:
<223> OTHER INFORMATION: Glycine/serine linker

<400> SEQUENCE: 50

Ser Gly Gly Gly Gly Ser Gly Gly Gly Gly
1 5 10

<210> SEQ ID NO 51
<211> LENGTH: 164
<212> TYPE: PRT
<213> ORGANISM: artificial
<220> FEATURE:
<223> OTHER INFORMATION: 1111-B4_21231

<400> SEQUENCE: 51

Met Gln Ile Phe Val Gly Thr Val Ala Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Lys Arg Asn
50 55 60

Pro Glu Leu His Leu Val Leu Arg Leu Arg Ala Ala Ser Gly Gly Gly
65 70 75 80

Gly Ser Gly Gly Gly Gly Ile Gly Met Gln Ile Phe Val Arg Thr Met
85 90 95

Thr Gly Lys Thr Ile Thr Leu Glu Val Glu Pro Ser Asp Thr Ile Glu
100 105 110

Asn Val Lys Ala Lys Ile Gln Asp Lys Glu Gly Ile Pro Pro Asp Gln
115 120 125

Gln Arg Leu Ile Trp Ala Gly Lys Gln Leu Glu Asp Gly Arg Thr Leu
130 135 140

Ser Asp Tyr Asn Ile Glu Thr Gly Val Val Leu His Leu Val Leu Arg
145 150 155 160

Leu Arg Ala Ala

<210> SEQ ID NO 52

-continued

<211> LENGTH: 164
<212> TYPE: PRT
<213> ORGANISM: artificial
<220> FEATURE:
<223> OTHER INFORMATION: 1111-C9

<400> SEQUENCE: 52

```
Met Gln Ile Phe Val Gly Thr Val Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Lys Arg Asn
    50                  55                  60

Pro Glu Leu His Leu Val Leu Arg Leu Arg Ala Ala Ser Gly Gly Gly
65                  70                  75                  80

Gly Ser Gly Gly Gly Gly Ile Gly Met Gln Ile Phe Val Arg Thr Met
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Glu Thr Gly Val Val Leu His Leu Val Leu Arg
145                 150                 155                 160

Leu Arg Ala Ala
```

<210> SEQ ID NO 53
<211> LENGTH: 155
<212> TYPE: PRT
<213> ORGANISM: artificial
<220> FEATURE:
<223> OTHER INFORMATION: 1111-E10

<400> SEQUENCE: 53

```
Met Gln Ile Phe Val Glu Thr Phe Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Trp His
    50                  55                  60

Pro Glu Leu His Leu Val Leu Arg Leu Arg Gly Gly Gly Ile Gly Met
65                  70                  75                  80

Gln Ile Phe Val Arg Thr Glu Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Leu Met Gly Tyr
    130                 135                 140

Val Leu His Leu Val Leu Arg Leu Arg Ala Ala
145                 150                 155
```

<210> SEQ ID NO 54
<211> LENGTH: 155
<212> TYPE: PRT
<213> ORGANISM: artificial
<220> FEATURE:
<223> OTHER INFORMATION: 1111-F6

<400> SEQUENCE: 54

```
Met Gln Ile Phe Val Pro Thr Trp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Pro Arg
    50                  55                  60

Thr Leu Leu His Leu Val Leu Arg Leu Arg Gly Gly Gly Ile Gly Met
65                  70                  75                  80

Gln Ile Phe Val Tyr Thr Thr Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Leu Leu Val Ala
    130                 135                 140

Leu Leu His Leu Val Leu Arg Leu Arg Ala Ala
145                 150                 155
```

<210> SEQ ID NO 55
<211> LENGTH: 155
<212> TYPE: PRT
<213> ORGANISM: artificial
<220> FEATURE:
<223> OTHER INFORMATION: 1111-H12

<400> SEQUENCE: 55

```
Met Gln Ile Phe Val Glu Thr Phe Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Trp His
    50                  55                  60

Pro Glu Leu His Leu Val Leu Arg Leu Arg Gly Gly Glu Ile Gly Met
65                  70                  75                  80

Gln Ile Phe Val Arg Thr Met Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Glu Thr Gly Val
    130                 135                 140

Val Leu His Leu Val Leu Arg Leu Arg Ala Ala
145                 150                 155
```

<210> SEQ ID NO 56
<211> LENGTH: 155
<212> TYPE: PRT
<213> ORGANISM: artificial
<220> FEATURE:
<223> OTHER INFORMATION: 1111-H2

<400> SEQUENCE: 56

```
Met Gln Ile Phe Val Glu Thr Phe Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Trp His
    50                  55                  60

Pro Glu Leu His Leu Val Leu Arg Leu Arg Gly Gly Gly Ile Gly Met
65                  70                  75                  80

Gln Ile Phe Val Arg Thr Met Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Glu Thr Gly Val
    130                 135                 140

Val Leu His Leu Val Leu Arg Leu Arg Ala Ala
145                 150                 155
```

<210> SEQ ID NO 57
<211> LENGTH: 88
<212> TYPE: PRT
<213> ORGANISM: artificial
<220> FEATURE:
<223> OTHER INFORMATION: 6-A12

<400> SEQUENCE: 57

```
Met Phe Ile Tyr Val Val Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro His Tyr
    50                  55                  60

Pro Arg Leu Gln Leu Val Leu Arg Leu Arg Gly Gly Ser Gly Gly Gly
65                  70                  75                  80

Gly Ser Gly Gly Gly Gly Ile Gly
                85
```

<210> SEQ ID NO 58
<211> LENGTH: 88
<212> TYPE: PRT
<213> ORGANISM: artificial
<220> FEATURE:
<223> OTHER INFORMATION: 16-A4

<400> SEQUENCE: 58

```
Met Tyr Ile Val Val Leu Thr Leu Thr Gly Lys Thr Ile Thr Leu Glu
1               5                   10                  15
```

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Ile Pro Gln
50 55 60

Met Ala Leu His Leu Val Leu Arg Leu Arg Gly Gly Ser Gly Gly Gly
65 70 75 80

Gly Ser Gly Gly Gly Gly Ile Gly
85

<210> SEQ ID NO 59
<211> LENGTH: 88
<212> TYPE: PRT
<213> ORGANISM: artificial
<220> FEATURE:
<223> OTHER INFORMATION: 7-D1

<400> SEQUENCE: 59

Met Met Ile Tyr Val Leu Thr Leu Thr Gly Lys Thr Ile Thr Leu Glu
1 5 10 15

Val Glu Pro Ser Asp Thr Ile Glu Asn Val Lys Ala Glu Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Pro Thr Asp
50 55 60

Ala Leu Leu His Leu Val Leu Arg Leu Arg Gly Gly Ser Gly Gly Gly
65 70 75 80

Gly Ser Gly Gly Gly Gly Ile Gly
85

<210> SEQ ID NO 60
<211> LENGTH: 88
<212> TYPE: PRT
<213> ORGANISM: artificial
<220> FEATURE:
<223> OTHER INFORMATION: 14-D11

<400> SEQUENCE: 60

Met Leu Ile Ile Val Gly Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Pro Thr Val
50 55 60

Asn Ala Leu His Leu Val Leu Arg Leu Arg Gly Gly Ser Gly Gly Gly
65 70 75 80

Gly Ser Gly Gly Gly Gly Ile Gly
85

<210> SEQ ID NO 61
<211> LENGTH: 88
<212> TYPE: PRT
<213> ORGANISM: artificial
<220> FEATURE:
<223> OTHER INFORMATION: 12-E6

<400> SEQUENCE: 61

```
Met Leu Ile Gly Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Arg Gly
    50                  55                  60

Thr Ala Leu His Leu Val Leu Arg Leu Arg Gly Gly Ser Gly Gly Gly
65                  70                  75                  80

Gly Ser Gly Gly Gly Gly Ile Gly
                85
```

<210> SEQ ID NO 62
<211> LENGTH: 88
<212> TYPE: PRT
<213> ORGANISM: artificial
<220> FEATURE:
<223> OTHER INFORMATION: 12-G9

<400> SEQUENCE: 62

```
Met Phe Ile Trp Val Val Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Arg Ser Thr
    50                  55                  60

Thr Met Leu His Leu Val Leu Arg Leu Arg Gly Gly Ser Gly Gly Gly
65                  70                  75                  80

Gly Ser Gly Gly Gly Gly Ile Gly
                85
```

<210> SEQ ID NO 63
<211> LENGTH: 76
<212> TYPE: PRT
<213> ORGANISM: artificial
<220> FEATURE:
<223> OTHER INFORMATION: 1144-D1

<400> SEQUENCE: 63

```
Met Gln Ile Phe Val Lys Thr Leu Thr Gly Lys Thr Ile Thr Leu Glu
1               5                   10                  15

Val Glu Pro Ser Asp Thr Ile Glu Asn Val Glu Ala Lys Ile Gln Asp
            20                  25                  30

Lys Glu Gly Ile Pro Pro Asp Gln Gln His Leu Thr Phe Ala Gly Lys
        35                  40                  45

Gln Leu Gly Asp Gly Arg Thr Leu Ser Asp Tyr Asn Ile Gln Lys Glu
    50                  55                  60

Ser Thr Leu Ser Leu Leu Leu Gly Val Trp Ala Ala
65                  70                  75
```

<210> SEQ ID NO 64
<211> LENGTH: 88
<212> TYPE: PRT
<213> ORGANISM: artificial
<220> FEATURE:
<223> OTHER INFORMATION: 1144-E9

<400> SEQUENCE: 64

Met Phe Ile Tyr Val Val Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro His Tyr
    50                  55                  60

Pro Arg Leu Gln Leu Lys Leu Lys His Ser Ala Ala Ser Gly Gly Gly
65                  70                  75                  80

Gly Ser Gly Gly Gly Gly Ile Gly
                85

<210> SEQ ID NO 65
<211> LENGTH: 118
<212> TYPE: PRT
<213> ORGANISM: artificial
<220> FEATURE:
<223> OTHER INFORMATION: 1076-H4

<400> SEQUENCE: 65

Met Phe Ile Tyr Val Val Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro His Tyr
    50                  55                  60

Pro Arg Leu Gln Leu Gln Leu Lys His Asp Ala Ala Asn Glu Ser Gly
65                  70                  75                  80

Gly Gly Gly Ser Gly Gly Gly Gly Ile Gly Asn Glu Gly Gly Ala Ala
                85                  90                  95

Trp Arg Asp Glu His Ile Glu Arg Asx Glu Trp Ser Ser Thr Glu Ile
            100                 105                 110

Asn Gly Glu Asx Ala Thr
        115

<210> SEQ ID NO 66
<211> LENGTH: 88
<212> TYPE: PRT
<213> ORGANISM: artificial
<220> FEATURE:
<223> OTHER INFORMATION: 1081-B11

<400> SEQUENCE: 66

Met Phe Ile Tyr Val Val Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro His Tyr
    50                  55                  60

Pro Arg Leu Gln Leu Tyr Leu Lys Ser Asp Ala Ala Ser Gly Gly Gly
65                  70                  75                  80

Gly Ser Gly Gly Gly Gly Ile Gly
85

<210> SEQ ID NO 67
<211> LENGTH: 88
<212> TYPE: PRT
<213> ORGANISM: artificial
<220> FEATURE:
<223> OTHER INFORMATION: 1081-H11

<400> SEQUENCE: 67

Met Phe Ile Tyr Val Val Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Pro His Tyr
50 55 60

Pro Arg Leu Gln Leu Ser Leu Lys Asp Asp Ala Ala Ser Gly Gly Gly
65 70 75 80

Gly Ser Gly Gly Gly Gly Ile Gly
85

<210> SEQ ID NO 68
<211> LENGTH: 88
<212> TYPE: PRT
<213> ORGANISM: artificial
<220> FEATURE:
<223> OTHER INFORMATION: 1082-A10

<400> SEQUENCE: 68

Met Phe Ile Tyr Val Val Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Pro His Tyr
50 55 60

Pro Arg Leu Gln Leu Ser Leu Lys Asp Asp Ala Ala Ser Gly Gly Gly
65 70 75 80

Gly Ser Gly Gly Gly Gly Ile Gly
85

<210> SEQ ID NO 69
<211> LENGTH: 88
<212> TYPE: PRT
<213> ORGANISM: artificial
<220> FEATURE:
<223> OTHER INFORMATION: 1082-A11

<400> SEQUENCE: 69

Met Phe Ile Tyr Val Val Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Pro His Tyr
50 55 60

Pro Arg Leu Gln Leu Lys Leu Gln Ser Gln Ala Ala Ser Gly Gly Gly
65 70 75 80

Gly Ser Gly Gly Gly Gly Ile Gly
85

<210> SEQ ID NO 70
<211> LENGTH: 88
<212> TYPE: PRT
<213> ORGANISM: artificial
<220> FEATURE:
<223> OTHER INFORMATION: 1088-A5

<400> SEQUENCE: 70

Met Phe Ile Tyr Val Val Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Pro His Tyr
50 55 60

Pro Arg Leu Gln Leu Lys Leu Lys Leu Ala Ala Ala Ser Gly Gly Gly
65 70 75 80

Gly Ser Gly Gly Gly Gly Ile Gly
85

<210> SEQ ID NO 71
<211> LENGTH: 88
<212> TYPE: PRT
<213> ORGANISM: artificial
<220> FEATURE:
<223> OTHER INFORMATION: 1091-A2

<400> SEQUENCE: 71

Met Phe Ile Tyr Val Val Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Pro His Tyr
50 55 60

Pro Arg Leu Gln Leu His Leu His Leu His Ala Ala Ser Gly Gly Gly
65 70 75 80

Gly Ser Gly Gly Gly Gly Ile Gly
85

<210> SEQ ID NO 72
<211> LENGTH: 88
<212> TYPE: PRT
<213> ORGANISM: artificial
<220> FEATURE:
<223> OTHER INFORMATION: 1094-D9

<400> SEQUENCE: 72

Met Phe Ile Tyr Val Val Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys

-continued

```
        35                  40                  45

Gln Leu Glu Asp Gly Arg Thr Leu Ser Asp Tyr Asn Ile Pro His Tyr
    50                  55                  60

Pro Arg Leu Gln Leu Lys Leu Leu His Ser Ala Ala Ser Gly Gly Gly
65                  70                  75                  80

Gly Ser Gly Gly Gly Gly Ile Gly
                85


<210> SEQ ID NO 73
<211> LENGTH: 76
<212> TYPE: PRT
<213> ORGANISM: artificial
<220> FEATURE:
<223> OTHER INFORMATION: 6-A12

<400> SEQUENCE: 73

Met Gln Ile Phe Val Val Thr Glu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Leu Thr Thr
    50                  55                  60

Gly Pro Leu His Leu Val Leu Arg Leu Arg Gly Gly
65                  70                  75


<210> SEQ ID NO 74
<211> LENGTH: 76
<212> TYPE: PRT
<213> ORGANISM: artificial
<220> FEATURE:
<223> OTHER INFORMATION: 16-A4

<400> SEQUENCE: 74

Met Gln Ile Phe Val Val Thr Glu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Leu Arg Thr
    50                  55                  60

Gly Pro Leu His Leu Val Leu Arg Leu Arg Gly Gly
65                  70                  75


<210> SEQ ID NO 75
<211> LENGTH: 76
<212> TYPE: PRT
<213> ORGANISM: artificial
<220> FEATURE:
<223> OTHER INFORMATION: 7-D1

<400> SEQUENCE: 75

Met Gln Ile Phe Val Val Thr Ser Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45
```

Gln Leu Glu Asp Gly Arg Thr Leu Ser Asp Tyr Asn Ile Leu Thr His
    50                  55                  60

Gly Pro Leu His Leu Val Leu Arg Leu Arg Gly Gly
65                  70                  75

<210> SEQ ID NO 76
<211> LENGTH: 76
<212> TYPE: PRT
<213> ORGANISM: artificial
<220> FEATURE:
<223> OTHER INFORMATION: 14-D11

<400> SEQUENCE: 76

Met Gln Ile Phe Val Val Thr Ala Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Leu Arg Thr
    50                  55                  60

Gly Pro Leu His Leu Val Leu Arg Leu Arg Gly Gly
65                  70                  75

<210> SEQ ID NO 77
<211> LENGTH: 76
<212> TYPE: PRT
<213> ORGANISM: artificial
<220> FEATURE:
<223> OTHER INFORMATION: 12-E6

<400> SEQUENCE: 77

Met Gln Ile Phe Val Val Thr Glu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Leu Ala Thr
    50                  55                  60

Gly Pro Leu His Leu Val Leu Arg Leu Arg Gly Gly
65                  70                  75

<210> SEQ ID NO 78
<211> LENGTH: 76
<212> TYPE: PRT
<213> ORGANISM: artificial
<220> FEATURE:
<223> OTHER INFORMATION: 12-G9

<400> SEQUENCE: 78

Met Gln Ile Phe Val Val Thr Glu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Leu Arg Thr
    50                  55                  60

Gly Pro Leu His Leu Val Leu Arg Leu Arg Gly Gly
65                  70                  75

<210> SEQ ID NO 79
<211> LENGTH: 76
<212> TYPE: PRT
<213> ORGANISM: artificial
<220> FEATURE:
<223> OTHER INFORMATION: 1144-D1

<400> SEQUENCE: 79

```
Met Gln Ile Phe Val Glu Thr Asp Thr Gly Lys Thr Ile Thr Leu Glu
1               5                   10                  15

Val Glu Pro Ser Asp Thr Ile Glu Asn Val Glu Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Thr Asp
    50                  55                  60

Ala Ala Leu His Leu Val Leu Arg Leu Arg Ala Ala
65                  70                  75
```

<210> SEQ ID NO 80
<211> LENGTH: 76
<212> TYPE: PRT
<213> ORGANISM: artificial
<220> FEATURE:
<223> OTHER INFORMATION: 1144-E9

<400> SEQUENCE: 80

```
Met Gln Ile Phe Val Glu Thr Ile Thr Gly Lys Thr Ile Thr Leu Glu
1               5                   10                  15

Val Glu Pro Ser Asp Thr Ile Glu Asn Val Glu Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Tyr Asp Gln
    50                  55                  60

Leu Ser Leu His Leu Val Leu Arg Leu Arg Ala Ala
65                  70                  75
```

<210> SEQ ID NO 81
<211> LENGTH: 76
<212> TYPE: PRT
<213> ORGANISM: artificial
<220> FEATURE:
<223> OTHER INFORMATION: 1076-H4

<400> SEQUENCE: 81

```
Met Gln Ile Phe Val Val Thr Glu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Leu Thr Thr
    50                  55                  60

Gly Pro Leu His Leu Val Leu Arg Leu Arg Ala Ala
65                  70                  75
```

<210> SEQ ID NO 82
<211> LENGTH: 76
<212> TYPE: PRT

<213> ORGANISM: artificial
<220> FEATURE:
<223> OTHER INFORMATION: 1081-B11

<400> SEQUENCE: 82

Met Gln Ile Phe Val Val Thr Glu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Leu Thr Thr
50 55 60

Gly Pro Leu His Leu Val Leu Arg Leu Arg Ala Ala
65 70 75

<210> SEQ ID NO 83
<211> LENGTH: 76
<212> TYPE: PRT
<213> ORGANISM: artificial
<220> FEATURE:
<223> OTHER INFORMATION: 1081-H11

<400> SEQUENCE: 83

Met Gln Ile Phe Val Val Thr Glu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Leu Thr Thr
50 55 60

Gly Pro Leu His Leu Val Leu Arg Leu Arg Ala Ala
65 70 75

<210> SEQ ID NO 84
<211> LENGTH: 76
<212> TYPE: PRT
<213> ORGANISM: artificial
<220> FEATURE:
<223> OTHER INFORMATION: 1082-A10

<400> SEQUENCE: 84

Met Gln Ile Phe Val Val Thr Glu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Leu Thr Thr
50 55 60

Gly Pro Leu His Leu Val Leu Arg Leu Arg Ala Ala
65 70 75

<210> SEQ ID NO 85
<211> LENGTH: 76
<212> TYPE: PRT
<213> ORGANISM: artificial
<220> FEATURE:
<223> OTHER INFORMATION: 1082-A11

<400> SEQUENCE: 85

Met Gln Ile Phe Val Val Thr Glu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Leu Thr Thr
    50                  55                  60

Gly Pro Leu His Leu Val Leu Arg Leu Arg Ala Ala
65                  70                  75

<210> SEQ ID NO 86
<211> LENGTH: 76
<212> TYPE: PRT
<213> ORGANISM: artificial
<220> FEATURE:
<223> OTHER INFORMATION: 1088-A5

<400> SEQUENCE: 86

Met Gln Ile Phe Val Val Thr Glu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Leu Thr Thr
    50                  55                  60

Gly Pro Leu His Leu Val Leu Arg Leu Arg Ala Ala
65                  70                  75

<210> SEQ ID NO 87
<211> LENGTH: 76
<212> TYPE: PRT
<213> ORGANISM: artificial
<220> FEATURE:
<223> OTHER INFORMATION: 1091-A2

<400> SEQUENCE: 87

Met Gln Ile Phe Val Val Thr Glu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Leu Thr Thr
    50                  55                  60

Gly Pro Leu His Leu Val Leu Arg Leu Arg Ala Ala
65                  70                  75

<210> SEQ ID NO 88
<211> LENGTH: 76
<212> TYPE: PRT
<213> ORGANISM: artificial
<220> FEATURE:
<223> OTHER INFORMATION: 1094-D4

<400> SEQUENCE: 88

Met Gln Ile Phe Val Val Thr Glu Thr Gly Lys Thr Ile Thr Leu Glu
1               5                   10                  15

Val Glu Pro Ser Asp Thr Ile Glu Asn Val Lys Ala Lys Ile Gln Asp 20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Leu Thr Thr
50 55 60

Gly Pro Leu His Leu Val Leu Arg Leu Arg Ala Ala
65 70 75

<210> SEQ ID NO 89
<211> LENGTH: 164
<212> TYPE: PRT
<213> ORGANISM: artificial
<220> FEATURE:
<223> OTHER INFORMATION: SPWF-15_6-A12

<400> SEQUENCE: 89

Met Phe Ile Tyr Val Val Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Pro His Tyr
50 55 60

Pro Arg Leu Gln Leu Val Leu Arg Leu Arg Gly Gly Ser Gly Gly Gly
65 70 75 80

Gly Ser Gly Gly Gly Gly Ile Gly Met Gln Ile Phe Val Val Thr Glu
85 90 95

Thr Gly Lys Thr Ile Thr Leu Glu Val Glu Pro Ser Asp Thr Ile Glu
100 105 110

Asn Val Lys Ala Lys Ile Gln Asp Lys Glu Gly Ile Pro Pro Asp Gln
115 120 125

Gln Arg Leu Ile Trp Ala Gly Lys Gln Leu Glu Asp Gly Arg Thr Leu
130 135 140

Ser Asp Tyr Asn Ile Leu Thr Thr Gly Pro Leu His Leu Val Leu Arg
145 150 155 160

Leu Arg Gly Gly

<210> SEQ ID NO 90
<211> LENGTH: 164
<212> TYPE: PRT
<213> ORGANISM: artificial
<220> FEATURE:
<223> OTHER INFORMATION: SPWF-15_16-D4_Th

<400> SEQUENCE: 90

Met Tyr Ile Val Val Leu Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Ile Pro Gln
50 55 60

Met Ala Leu His Leu Val Leu Arg Leu Arg Gly Gly Ser Gly Gly Gly
65 70 75 80

Gly Ser Gly Gly Gly Gly Ile Gly Met Gln Ile Phe Val Val Thr Glu
85 90 95

Thr Gly Lys Thr Ile Thr Leu Glu Val Glu Pro Ser Asp Thr Ile Glu
100 105 110

Asn Val Lys Ala Lys Ile Gln Asp Lys Glu Gly Ile Pro Pro Asp Gln
115 120 125

Gln Arg Leu Ile Trp Ala Gly Lys Gln Leu Glu Asp Gly Arg Thr Leu
130 135 140

Ser Asp Tyr Asn Ile Leu Arg Thr Gly Pro Leu His Leu Val Leu Arg
145 150 155 160

Leu Arg Gly Gly

<210> SEQ ID NO 91
<211> LENGTH: 164
<212> TYPE: PRT
<213> ORGANISM: artificial
<220> FEATURE:
<223> OTHER INFORMATION: SPWF-9_1-B7_th

<400> SEQUENCE: 91

Met Met Ile Ser Val Tyr Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Asp Asp Gly Arg Thr Leu Ser Asp Tyr Asn Ile Arg Ser Arg
50 55 60

Gly Leu Leu His Leu Val Leu Arg Leu Arg Gly Gly Ser Gly Gly Gly
65 70 75 80

Gly Ser Gly Gly Gly Gly Ile Gly Met Gln Ile Phe Val Leu Thr His
85 90 95

Thr Gly Lys Thr Ile Thr Leu Glu Val Glu Pro Ser Asp Thr Ile Glu
100 105 110

Asn Val Lys Ala Lys Ile Gln Asp Lys Glu Gly Ile Pro Pro Asp Gln
115 120 125

Gln Arg Leu Ile Trp Ala Gly Lys Gln Leu Glu Asp Gly Arg Thr Leu
130 135 140

Ser Asp Tyr Asn Ile Ser His Ser Arg Thr Leu His Leu Val Leu Arg
145 150 155 160

Leu Arg Gly Gly

<210> SEQ ID NO 92
<211> LENGTH: 164
<212> TYPE: PRT
<213> ORGANISM: artificial
<220> FEATURE:
<223> OTHER INFORMATION: SPWF-9_6-A2_th

<400> SEQUENCE: 92

Met Ala Ile Val Val Tyr Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Trp Ala Gly Lys
35 40 45

Gln Leu Glu Asp Gly Arg Thr Leu Ser Asp Tyr Asn Ile Pro Met Pro
50 55 60

Val Leu Leu His Leu Val Leu Arg Leu Arg Gly Gly Ser Gly Gly Gly

-continued

```
65                  70                  75                  80

Gly Ser Gly Gly Gly Gly Ile Gly Met Gln Ile Phe Val Asn Thr Ser
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Asp Gln Gln Arg Ile Leu His Leu Val Leu Arg
145                 150                 155                 160

Leu Arg Gly Gly


<210> SEQ ID NO 93
<211> LENGTH: 164
<212> TYPE: PRT
<213> ORGANISM: artificial
<220> FEATURE:
<223> OTHER INFORMATION: SPVF-4_16-B2_ts

<400> SEQUENCE: 93

Met Gln Ile Phe Val Asp Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Leu Ile Glu
    50                  55                  60

Trp Leu Leu His Leu Val Leu Arg Leu Arg Gly Gly Ser Gly Gly Gly
65                  70                  75                  80

Gly Ser Gly Gly Gly Gly Ile Gly Met Gln Ile Phe Val Asp Thr Leu
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Gly Ala Asp Ala Pro Leu His Leu Val Leu Arg
145                 150                 155                 160

Leu Arg Gly Gly


<210> SEQ ID NO 94
<211> LENGTH: 164
<212> TYPE: PRT
<213> ORGANISM: artificial
<220> FEATURE:
<223> OTHER INFORMATION: SPVF-4_9-C6_ts

<400> SEQUENCE: 94

Met Gln Ile Phe Val Asp Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45
```

-continued

```
Gln Leu Glu Asp Gly Arg Thr Leu Ser Asp Tyr Asn Ile Thr Phe Asn
    50                  55                  60

Pro Gln Leu His Leu Val Leu Arg Leu Arg Gly Gly Ser Gly Gly Gly
65                  70                  75                  80

Gly Ser Gly Gly Gly Gly Ile Gly Met Gln Ile Phe Val Trp Thr Thr
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Pro His Trp Arg Ile Leu His Leu Val Leu Arg
145                 150                 155                 160

Leu Arg Gly Gly


<210> SEQ ID NO 95
<211> LENGTH: 101
<212> TYPE: PRT
<213> ORGANISM: artificial
<220> FEATURE:
<223> OTHER INFORMATION: Amino acid core region of MIA-2

<400> SEQUENCE: 95

Met Leu Glu Ser Thr Lys Leu Leu Ala Asp Leu Lys Lys Cys Gly Asp
1               5                   10                  15

Leu Glu Cys Glu Ala Leu Ile Asn Arg Val Ser Ala Met Arg Asp Tyr
            20                  25                  30

Arg Gly Pro Asp Cys Arg Tyr Leu Asn Phe Thr Lys Gly Glu Glu Ile
        35                  40                  45

Ser Val Tyr Val Lys Leu Ala Gly Glu Arg Glu Asp Leu Trp Ala Gly
    50                  55                  60

Ser Lys Gly Lys Glu Phe Gly Tyr Phe Pro Arg Asp Ala Val Gln Ile
65                  70                  75                  80

Glu Glu Val Phe Ile Ser Glu Glu Ile Gln Met Ser Thr Lys Glu Ser
                85                  90                  95

Asp Phe Leu Cys Leu
            100


<210> SEQ ID NO 96
<211> LENGTH: 12
<212> TYPE: PRT
<213> ORGANISM: artificial
<220> FEATURE:
<223> OTHER INFORMATION: Glycine/serine linker

<400> SEQUENCE: 96

Ser Gly Gly Gly Gly Ser Gly Gly Gly Gly Ile Gly
1               5                   10
```

METHOD FOR IDENTIFYING HETERO-MULTIMERIC MODIFIED UBIQUITIN PROTEINS WITH BINDING CAPABILITY TO LIGANDS

FIELD OF THE INVENTION

The present invention refers to a method for identifying hetero-multimeric ubiquitin with binding capability to a ligand. Furthermore, the invention provides DNA libraries encoding for a population of said hetero-multimeric ubiquitin proteins as well as protein libraries obtained by expression of said DNA libraries, cells, and phages containing said DNA or proteins, polynucleotides encoding for said fusion proteins and vectors comprising said polynucleotides. Further new binding proteins based on hetero-multimeric ubiquitins being able to bind specifically with high affinity to selected ligands are provided.

BACKGROUND OF THE INVENTION

There is a growing demand for binding molecules consisting of amino acids which are not immunoglobulins. While until now antibodies represent the best-established class of binding molecules there is still a need for new binding molecules in order to target ligands with high affinity and specificity since immunoglobulin molecules suffer from major drawbacks. Although they can be produced quite easily and may be directed to almost any target, they have a quite complex molecular structure. There is an ongoing need to substitute antibodies by smaller molecules which can be handled in an easy way. These alternative binding agents can be beneficially used for instance in the medical fields of diagnosis, prophylaxis and treatment of diseases.

Proteins having relatively defined 3-dimensional structures, commonly referred to as protein scaffolds, may be used as starting material for the design of said alternative binding agents. These scaffolds typically contain one or more regions which are amenable to specific or random sequence variation, and such sequence randomisation is often carried out to produce a library of proteins from which the specific binding molecules may be selected. Molecules with a smaller size than antibodies and a comparable or even better affinity towards a target antigen are expected to be superior to antibodies in terms of pharmacokinetic properties and immunogenicity.

A number of previous approaches do use protein scaffolds as starting material of binding proteins. For example, in WO 99/16873 modified proteins of the lipocalin family (so-called Anticalins) exhibiting binding activity for certain ligands were developed. The structure of peptides of the lipocalin family is modified by amino acid replacements in their natural ligand binding pocket using genetic engineering methods. Like immunoglobulins, the Anticalins can be used to identify or bind molecular structures. In a manner analogously to antibodies, flexible loop structures are modified; these modifications enable the recognition of ligands different from the natural ones.

WO 01/04144 describes the artificial generation of a binding domain on the protein surface. in beta sheet structural proteins per se lacking a binding site, By means of this de novo generated artificial binding domain e.g. variations in γ-crystallin—an eye lens structural protein—can be obtained which interact with ligands with high affinity and specificity. In contrast to the modification of binding sites which are already present and formed from flexible loop structures as mentioned above for Anticalins, these binding domains are generated de novo on the surface of beta sheets. However, WO 01/04144 only describes the alteration of relatively large proteins for the generation of novel binding properties. Due to their size the proteins according to WO 01/04144 can be modified on the genetic engineering level only by methods which require some effort. Furthermore, in the proteins disclosed so far only a relatively small proportion by percentage of the total amino acids was modified in order to maintain the overall structure of the protein. Therefore, only a relatively small region of the protein surface is available which can be utilized for the generation of binding properties that did not exist previously. Moreover, WO 01/04144 discloses only the generation of a binding property to γ-crystallin.

WO 04/106368 describes the generation of artificial binding proteins on the basis of ubiquitin proteins. Ubiquitin is a small, monomeric, and cytosolic protein which is highly conserved in sequence and is present in all known eukaryotic cells from protozoans to vertebrates. In the organism, it plays a crucial role in the regulation of the controlled degradation of cellular proteins. For this purpose, the proteins destined for degradation are covalently linked to ubiquitin or polyubiquitin chains during their passage through a cascade of enzymes and are selectively degraded because of this label. According to recent results, ubiquitin or the labelling of proteins by ubiquitin, respectively, plays an important role also in other cellular processes such as the import of several proteins or the gene regulation thereof.

Besides the clarification of its physiological function, ubiquitin is a research object primarily because of its structural and protein-chemical properties. The polypeptide chain of ubiquitin consists of 76 amino acids folded in an extraordinarily compact α/β structure (Vijay-Kumar, 1987): almost 87% of the polypeptide chain is involved in the formation of the secondary structural elements by means of hydrogen bonds. Prominent secondary structures are three and a half alpha-helical turns as well as an antiparallel β sheet consisting of four strands. The characteristic arrangement of these elements—an antiparallel β sheet exposed of the protein surface onto the back side of which an alpha helix is packed which lies vertically on top of it—is generally considered as so-called ubiquitin-like folding motif. A further structural feature is a marked hydrophobic region in the protein interior between the alpha helix and the β sheet.

Because of its small size, artificial preparation of ubiquitin can be carried out both by chemical synthesis and by means of biotechnological methods. Due to the favourable folding properties, ubiquitin can be produced by genetic engineering using microorganisms such as *Escherichia coli* in relatively large amounts either in the cytosol or in the periplasmic space. Because of the oxidizing conditions predominating in the periplasm the latter strategy generally is reserved for the production of secretory proteins. Due to the simple and efficient bacterial preparation ubiquitin can be used as a fusion partner for other foreign proteins to be prepared for which the production is problematic. By means of fusion to ubiquitin an improved solubility and thereby an improved production yield can be achieved.

Compared to antibodies or other alternative scaffolds, artificial binding proteins on the basis of ubiquitin proteins (also referred to as Affilin®) have the advantages of a small size and high stability, high affinity, high specificity, cost effective microbial manufacturing, and adjustment of serum half life. However, there is still a need to further develop those proteins in terms of immunogenic potential, fast and predictive preclinical development track and new therapeutic approaches. While WO 05/05730 generally describes the use of ubiquitin scaffolds in order to obtain artificial binding proteins, no solution is provided on how to modify and on how to efficiently select such a modified ubiquitin protein in order to obtain an even higher and more specific affinity binding to ligands like haptens and antigens, e.g. proteins and peptides and epitopes thereof.

The methods described in WO 05/05730 refer to monomers of modified ubiquitin proteins or to coupled proteins of modified ubiquitin. The coupled forms are generated by screening and selecting one, two or more modified ubiquitin proteins and combining them afterwards either by genetic or chemical methods to obtain coupled forms which enable for example multispecific binding of different kinds of ligands by one coupled ubiquitin molecule. In one example, site-directed coupling of two identical ubiquitin-based proteins (homo-dimers) is described in order to increase the binding affinity compared to a single modified ubiquitin molecule It is an object of the present invention to provide a method on how to identify multimeric ubiquitin proteins with high binding capability to a ligand. It is a further object of the present invention to provide a method for identifying new binding proteins based on modified ubiquitin being able to bind specifically with high affinity to selected ligands.

The above-described objects are solved by the subject-matter of the enclosed independent claims. Preferred embodiments of the invention are included in the dependent claims as well as in the following description, examples and figures.

SUMMARY OF THE INVENTION

More specifically, the inventors provide a method for identifying a hetero-multimeric modified ubiquitin with binding capability to a ligand, comprising the following steps:

a) providing a population of hetero-multimeric modified ubiquitin proteins originating from monomeric modified ubiquitin proteins, said population comprising hetero-multimeric proteins comprising two or more differently modified ubiquitin monomers or at least one modified ubiquitin monomer linked together in a head-to-tail arrangement wherein at least two of each of said monomers of said hetero-multimeric protein are differently modified at least by substitutions of surface exposed amino acids in at least three amino acids located in positions 2, 4, 6, 8, 62, 63, 64, 65, 66, and 68 of SEQ ID NO: 1, said modified monomeric protein having an amino acid sequence identity of at least 80% or at least 90% or at least 95% to the unmodified ubiquitin protein;

b) providing a potential ligand to said population of differently modified proteins;

c) contacting said population of differently modified proteins with said ligand;

d) identifying a modified hetero-multimeric protein by a screening process, wherein said modified multimeric protein binds to said ligand with a specific binding affinity of Kd in a range of $10^{-7}$-$10^{-12}$ M and exhibits a monovalent binding activity with respect to said ligand; and optionally e) isolating said hetero-multimeric modified ubiquitin protein with said binding affinity.

DEFINITIONS OF IMPORTANT TERMS USED IN THE APPLICATION

The term "ubiquitin protein" covers the ubiquitin in accordance with SEQ ID NO: 1 and modifications thereof according to the following definition. Ubiquitin is highly conserved in eukaryotic organisms. For example, in all mammals investigated up to now ubiquitin has the identical amino acid sequence. Particularly preferred are ubiquitin molecules from humans, rodents, pigs, and primates. Additionally, ubiquitin from any other eukaryotic source can be used. For instance ubiquitin of yeast differs only in three amino acids from the sequence of SEQ ID NO: 1. Generally, the ubiquitin proteins covered by said term "ubiquitin protein" show an amino acid identity of more than 70%, preferably more than 75% or more than 80%, of more than 85%, of more than 90%, of more than 95%, of more than 96% or up to a sequence identity of 97% to SEQ ID NO: 1.

For determining the extent of sequence identity of a derivative of the ubiquitin to the amino acid sequence of SEQ ID NO: 1, for example, the SIM Local similarity program (Xiaoquin Huang and Webb Miller, "Advances in Applied Mathematics, vol. 12: 337-357, 1991) or Clustal, W. can be used (Thompson et al., Nucleic Acids Res., 22(22): 4673-4680, 1994.). Preferably, the extent of the sequence identity of the modified protein to SEQ ID NO: 1 is determined relative to the complete sequence of SEQ ID NO: 1.

In the present specification, the terms "ligand" and "target" and "binding partner" are used synonymously and can be exchanged. A ligand is any molecule capable of binding with an affinity as defined herein to the hetero-multimeric modified ubiquitin protein.

The "hetero-multimeric fusion protein" or "hetero-multimeric protein" of the invention is considered as a protein which comprises one or more different modified monomeric ubiquitin proteins. A "hetero-multimer" of the invention is, therefore, considered as a fusion of at least two differently modified monomeric ubiquitin proteins with two interacting binding domain regions providing together a monovalent binding property for a specific binding partner. Hetero-dimers or hetero-trimers are preferred.

According to the invention, at least two differently modified ubiquitin monomers which bind to one ligand are to be linked by head-to-tail fusion to each other using e.g. genetic methods. The differently modified fused ubiquitin monomers bind in a monovalent manner and are only effective if both binding domain regions ("BDR") act together. The modified and linked ubiquitin monomers which form the heteromeric protein bind to the same epitope via a single contiguous binding region. This contiguous region of the heteromer is formed by both binding determining regions of the at least two modules formed by at least two differently modified ubiquitin monomers.

A "head to-tail fusion" is to be understood as fusing two or more proteins together by linking them in the direction N—C—N—C— depending on the number of units contained in the multimer. In this head-to-tail fusion, the ubiquitin monomers can be connected directly without any linker. Alternatively, the fusion of ubiquitin monomers can be performed via linkers, for example, a linker [A1] having at least the amino acid sequence GIG or having at least the amino acid sequence SGGGG or any other linker, for example GIG, SGGGG, SGGGGIG, SGGGGSGGGGIG or SGGGGSGGGG. Also other linkers for the genetic fusion of two ubiquitin monomers are known in the art and can be used. Summarily, the hetero-multimeric umodified ubiquitin proteins are provided by a fusion of two, three or more differently modified monomeric ubiquitin proteins in order to obtain a fusion protein of modified ubiquitin monomers In a further embodiment, at least one of the ubiquitin monomers is not modified while at least one of the other ubiquitin molecules is modified.

The term "population" refers to a library which is a mixture of heterogeneous polypeptides encoded by heterogenous nucleic acids. The library is composed of members, which have a single polypeptide encoded by a nucleic acid sequence. Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Preferably, each individual organism or cell contains only one member of the library. Advantageously, the nucleic acids are incorporated into expression vectors, in order to allow production of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

Said population of hetero-multimeric ubiquitin proteins is provided for example by genetically fusing DNA libraries encoding each for differently modified monomeric proteins, or, in an alternative version, wherein at least one of said monomeric ubiquitin proteins is modified, translating the DNA into hetero-multimeric fusion proteins, displaying said proteins and screening the displayed proteins on the presence of modified hetero-multimeric ubiquitin proteins comprising monomeric ubiquitin proteins being linked together in a head-to-tail arrangement wherein said modified hetero-multimeric ubiquitin proteins bind to said ligand with a specific binding affinity of Kd in a range of $10^{-7}$-$10^{-12}$ M and exhibit a monovalent binding activity with respect to said ligand. In order to obtain a hetero-dimeric ubiquitin protein, two DNA libraries either encoding each or at least one for a differently modified monomeric protein are fused, in order to obtain a hetero-trimeric ubiquitin protein, three DNA libraries encoding each or at least one for a differently modified monomeric protein are fused, etc. Further alternatives may be used to provide libraries for screening. One example is chemical synthesis of the proteins e.g. by solid state technology and introducing variations in their amino acid composition. Further options may be considered and found to be useful by the skilled artisan. Therefore, the invention is not to be understood to be limited to the examples described herein.

The invention accordingly discloses a method by which a repertoire of polypeptides is provided, according to functionality as determined by the ability to bind a ligand, and a subset of polypeptides obtained as a result of selection is then employed for further rounds of selection according to the ability to bind the target ligand in order to accumulate and increase the binding affinity to the ligand.

The invention permits the person skilled in the art to remove, from a chosen repertoire of polypeptides, those polypeptides which are incapable of binding to the target ligand with the affinity specified in the claims. The invention permits the person skilled in the art to enrich a chosen repertoire of polypeptides for those polypeptides which are functional and meet the affinity requirements.

One of the most important key points of the invention lies in the selection of the modified hetero-multimeric ubiquitin proteins with monovalent binding affinity with respect to the target and subsequent determination of the modified amino acids responsible for the binding affinity.

A further advantage of multimerization, preferably dimerization, lies in the increase of the number of amino acid residues that can be modified to generate a new high affinity binding property. The advantage is that while even more amino acids are modified, the protein-chemical integrity is maintained without decreasing the overall stability of the scaffold of said newly created binding protein to a target. On the one hand the total number of residues which can be modified in order to generate a novel binding site for a given target is increased as the modified residues can be allocated to two or three or more monomeric ubiquitin proteins. The number of modifications can so be two times or x-times corresponding to the number of modified monomeric ubiquitin molecules. Summarizing, a modular structure of the ubiquitin-based binding protein allows increasing the overall number of modified amino acids as said modified amino acids are included on two or three or more monomeric ubiquitin molecules. The present method provides for the identification of hetero-multimeric ubiquitin molecules having one monovalent specificity (for one single epitope).

"Monovalent" has to be understood as the capability that both binding regions created in the first and the second (and optionally further) monomeric unit of the modified dimeric (optionally trimeric or generally multimeric) ubiquitin together bind ED-B in a synergistic and combined manner, i.e. both binding regions act together to form a monovalent binding activity. Taking each binding region of both the first and the second modified ubiquitin in said hetero-dimeric molecule separately will apparently bind ED-B with a much lower efficiency and affinity than the dimeric molecule. Both binding regions form a unique binding site which is formed as a contiguous region of amino acids on the surface of the hetero-dimeric modified ubiquitin protein so that said modified ubiquitin is feasible to bind much more efficient to ED-B than each monomeric protein taken alone. It is particularly important that according to the present invention the two monomeric proteins are not linked together after having screened the most potent binding ubiquitin molecules but that already the screening process is performed in the presence of the hetero-dimeric ubiquitins. After having received the sequence information on the most potent binding ubiquitin molecules, these molecules may be obtained by any other method, e.g. by chemical synthesis or by genetic engineering methods, e.g. by linking the two already identified monomeric ubiquitin units together. It is to be understood that all examples provided herein for dimeric modified ubiquitin proteins may also be altered to trimeric or generally multimeric modified ubiquitin protein.

Thus, the use of hetero-multimers, in particular hetero-dimers, having a common binding site for binding partners opens up the possibility to introduce an increased number of modified residues which do not unduly influence the protein-chemical integrity of the final binding molecule, since the overall amount of those modified residues is distributed over the two or more monomeric units which are forming the di- or multimer. Said hetero-multimeric modified ubiquitin proteins are present in a library of proteins.

After e.g. at least two different DNA libraries encoding for monomeric modified ubiquitin proteins have been established by differently modifying selected codons in each of the monomeric ubiquitin units, these libraries are genetically fused to obtain DNA molecules encoding for hetero-multimeric modified ubiquitin proteins. The DNA of these libraries is translated into proteins and the modified hetero-multimeric proteins obtained thereby are contacted according to the invention with a target molecule to enable binding of the partners to each other if a binding affinity does exist. The preferred modified ubiquitin is a hetero-dimer.

It is a crucial aspect of the invention that the contacting and screening process is performed already with respect to the hetero-multimeric, e.g. hetero-dimeric, modified ubiquitin protein. This process enables screening on those ubiquitin proteins which provide a monovalent binding activity to the target.

It is particularly important that according to the present invention the monomeric modified ubiquitin proteins are not linked together after having selected by screening the most potent binding ubiquitin molecules but that already the screening process is performed in the presence of the hetero-multimeric ubiquitins. However, it has to be noted that after having received the sequence information on the most potent hetero-multimeric ubiquitin binding molecules, these molecules may also be obtained by any other method, e.g. by chemical synthesis or by genetic engineering methods, e.g. by linking the two already identified differently modified monomeric ubiquitin units together to form a hetero-dimeric binding protein.

Contacting according to the invention is preferably performed by means of a suitable presentation and selection method such as the phage display, ribosomal display, TAT phage display, mRNA display or cell surface display, yeast surface display or bacterial surface display methods, preferably by means of the ribosome or phage display method. For complete disclosure, reference is made also to the following references: Hoess, Curr. Opin. Struct. Biol. 3 (1993), 572-579; Wells and Lowmann, Curr. Opin. Struct. Biol. 2 (1992), 597-604; Kay et al., Phage Display of Peptides and Proteins-A Laboratory Manual (1996), Academic Press. The methods mentioned above are known to those skilled in the art and can be used according to the invention including modifications thereof.

The determination whether the modified protein has a quantifiable binding affinity with respect to a predetermined binding partner can be performed according to the invention preferably by one or more of the following methods: ELISA, surface plasmon resonance spectroscopy, size exclusion chromatography, fluorescence anisotropy, fluorescence spectroscopy, FACS, isothermal titration calorimetry, and analytical ultracentrifugation. Other methods available in the art can be used also by the expert within his general knowledge.

A "hetero-multimer" is considered as a protein herein which comprises at least two different monomeric ubiquitin proteins. The "hetero-dimers" of the invention are considered as a fusion of two differently modified monomeric ubiquitin proteins. Both exhibit a combined monovalent binding property for the specific binding partner. It is emphasized that the modified multimeric, e.g. dimeric, ligand binding ubiquitin protein of the invention is not obtained by separately screening each monomeric ubiquitin protein and combining at least two of them afterwards but by screening for multimeric, optionally dimeric proteins consisting of a first and a second or a further monomeric unit which exhibit together a monovalent binding activity of said ligand. It is to be expected that each of said subunits exhibit a quite limited binding affinity towards the ligand while only the combined multimeric or dimeric modified ubiquitin protein will have the excellent binding properties described herein.

In one embodiment, the method relates to identifying a modified hetero-dimeric ubiquitin protein wherein two monomeric ubiquitin units are linked together in a head-to-tail arrangement, wherein each monomer of said dimeric protein is differently modified by substitutions of at least 3, preferably at least 6 amino acids in positions 2, 4, 6, 8, 62, 63, 64, 65, 66, and 68 of SEQ ID NO: 1 (each of them being surface-exposed) wherein said substitutions comprise (1) in the first monomeric unit substitutions at least in amino acid positions 6, 8, 63, 64, 65, and 66; and in the second monomeric unit substitutions at least in amino acid positions 6, 8, 62, 63, 64, 65, and 66; optionally additionally in amino acid position 2, or (2) in the first monomeric unit substitutions at least in amino acid positions 2, 4, 6, 62, 63, 64, 65, and 66; and in the second monomeric unit substitutions at least in amino acid positions 6, 8, 62, 63, 64, 65, and 66; optionally additionally in amino acid position 2, and optionally further modifications, preferably substitutions of other amino acids, said modified monomeric ubiquitin unit having an amino acid identity to SEQ ID NO: 1 of at least one of the group of 80%, at least 83%, at least 85%, at least 83% and at least 90%, said protein having a specific binding affinity to a ligand of $Kd=10^{-7}$-$10^{-12}$ M and exhibits a monovalent binding activity with respect to said ligand.

In further embodiments of the invention, 6, 7, 8, 9 or all of the amino acids in positions 2, 4, 6, 8, 62, 63, 64, 65, 66, and 68 of SEQ ID NO: 1 are modified in each monomeric ubiquitin unit. It is to be understood that the present invention allows a combination of each of these variations in each of the monomeric units, e.g. in the first and the second unit. For instance the first monomeric unit can comprise 6 modifications while the second unit comprises 7 or 8 modifications, the first unit may comprise 8 modifications and the second unit 7 modifications etc. Each of the amino acids listed above can be selected in the first and second unit and both units are then combined. Preferred substitutions are described herein below.

DETAILED DESCRIPTION OF THE INVENTION

Methods of Displaying the Modified Hetero-Multimeric Ubiquitin Proteins

Phage and ribosome display procedures adapted to this application are described in the following and in the Examples. They are recited as examples for a selection procedure according to the invention to detect variations of ubiquitin which show the binding properties to a potential ligand as described herein. In the same manner e.g. methods for the presentation on bacteria (bacterial surface display; Daugherty et al., 1998, Protein Eng. 11(9):825-832) or yeast cells (yeast surface display; Kieke et al., 1997 Protein Eng. 10(11):1303-10) or cell-free selection systems such as the ribosome display (Hanes and Plückthun, 1997 Proc Natl Acad Sci USA. 94(10):4937-4942; He and Taussig, 1997_Nucleic Acids Res analytical ultracentrifugation, 25(24):5132-5134) or the cis display (Odegrip et al., 2004 Proc Natl Acad Sci USA. 101 (9):2806-2810) or the mRNA display can be applied. In the latter case a transient physical linkage of genotype and phenotype is achieved by coupling of the protein variation to the appropriate mRNA via the ribosome.

In the phage display procedure described herein recombinant variations of ubiquitin are presented on a filamentous phage while the coding DNA of the presented variation is present at the same time packed in a single-stranded form in the phage envelope. Thus, in the frame of an affinity enrichment variations having certain properties can be selected from a library and their genetic information can be amplified by infection of suitable bacteria or added to another cycle of enrichment, respectively. Presentation of the mutated ubiquitin on the phage surface is achieved by genetic fusion to an amino-terminal signal sequence-preferably the Pe1B signal sequence—and a capsid or surface protein of the phage-preferred is the carboxyterminal fusion to the capsid protein pIII or a fragment thereof. Furthermore, the encoded fusion protein can contain further functional elements such as e.g. an affinity tag or an antibody epitope for detection and/or purification by affinity chromatography or a protease recognition sequence for specific cleavage of the fusion protein in the course of the affinity enrichment. Furthermore, an amber stop codon can be present for example between the gene for the ubiquitin variation and the coding region of the phage capsid protein or the fragment thereof which is not recognized during translation in a suitable suppressor strain partially due to the introduction of one amino acid.

The bacterial vector suitable for the selection procedure in the context of the isolation of ubiquitin variations with binding properties to a given target and into which the gene cassette for the fusion protein described is inserted is referred to as phagemid. Among others, it contains the intergenic region of a filamentous phage (e.g. M13 or f1) or a portion thereof which in the case of a superinfection of the bacterial cell carrying the phagemid by means of helper phages such as e.g. M13K07 results in the packaging of a covalently closed strand of phagemid DNA into a phage capsid. The phage particles generated in this manner are secreted by the bacterium and present the respective ubiquitin variation encoded on their surface due to its fusion to the capsid protein pIII or the fragment thereof—on their surface. Native pIII capsid proteins are present in the phage particle so that its ability to re-infect suitable bacterial strains and therefore the possibility to amplify the corresponding DNA is retained. Thus, the physical linkage between the phenotype of the ubiquitin variation—i.e. its potential binding property—and its genotype is ensured.

Phage particles obtained can be selected with respect to the binding of the ubiquitin variation presented thereon to any target, for example, ED-B, TNFalpha, MIA-2, NGF, IgG or other targets, by means of methods known to those skilled in the art. For this purpose, the presented ubiquitin variations can be transiently immobilized to target substance bound e.g. on microtiter plates and can be specifically eluted after non-binding variations have been separated. The elution is preferably performed by basic solutions such as e.g. 100 mM triethylamine. Alternatively, the elution can be performed under acidic conditions, by proteolysis or direct addition of infected bacteria. The phage particles obtained in this manner can be re-amplified and enriched by successive cycles of selection and amplification of ubiquitin variants with binding properties to for example, ED-B, TNFalpha, MIA-2, NGF, IgG or any other targets.

A variation of phage display is the Tat Phage display technique (Paschke, M. and W. Hohne (2005). Gene 350(1): 79-88; see also EP 1567643). With this method the ubiquitin variant which is encoded by the phagemid is secreted via the twin arginine translocation (Tat) system which exports folded proteins that have already attained their native conformation already in the cytoplasm (Brüser 2007 Appl Microbiol Biotechnol 76(1): 35-45). A requirement for secretion is the fusion to a specific N-terminal signal peptide which directs the ubiquitin variant towards the Tat pore. After entering the periplasmic space the N-terminal signal peptide is removed by a signal peptidase. In the periplasmic space the ubiquitin variant is then covalently linked to capsid protein pIII or a C-terminal fragment thereof which gets secreted from cytoplasma through the Sec pathway as well as other phage proteins, too. This linkage between ubiquitin and pIII is realized by the high-affinity interaction of the Jun leucine zipper at the N-terminus of the pIII protein and Fos leucine zipper at the C-terminus of the ubiquitin variant. Additional cysteines at the N- and C-termini of each of the leucine zippers enable a covalent link between both proteins and as a consequence, they also enable a covalent link between displayed ubiquitin and its encoding gene product within the phage particle.

Further characterization of the ubiquitin variations obtained in this way can be performed when still in the form of the phagemid, i.e. fused to the phage, or after cloning of the corresponding gene cassette into a suitable expression vector in the form of a soluble protein. The appropriate methods are known to those skilled in the art or described in the literature. The characterization can comprise e.g. the determination of the DNA sequence and thus of the primary sequence of the variations isolated. Furthermore, the affinity and specificity of the variations isolated can be detected e.g. by means of biochemical standard methods such as ELISA or surface plasmon resonance, size exclusion chromatography, fluorescence anisotropy, fluorescence spectroscopy, FACS, isothermal titration calorimetry or analytical ultracentrifugation, In view of the stability analysis, for example spectroscopic methods in connection with chemical or physical unfolding are known to those skilled in the art. Other well known methods are CD spectroscopy, protein fluorescence spectroscopy and NMR spectroscopy In a further embodiment of the invention, ribosomal display procedure variations of ubiquitin are prepared by means of a cell-free transcription/translation system and presented as a complex with the corresponding mRNA as well as the ribosome. For this purpose, a DNA library as described above is used as a basis in which the genes of variations are present in form of fusions with the corresponding regulatory sequences for expression and protein biosynthesis. Due to the deletion of the stop codon at the 3' end of the gene library as well as suitable experimental conditions (low temperature, high $Mg^{2+}$ concentration) the ternary complex consisting of the nascent protein, the mRNA and the ribosome is maintained during in vitro transcription/translation.

After a protein library containing hetero-dimeric modified ubiquitin proteins has been established by differently modifying of selected amino acids in each of the monomeric ubiquitin units, the modified dimeric proteins are contacted according to the invention with the target to enable binding of the partners to each other if a binding affinity does exist. These protein libraries may be in the form of a display method library displaying or using any other method presenting the modified proteins in a manner enabling the contact between the modified proteins and the target protein, wherein said display method is optionally a phage display, ribosomal display, TAT phage display, cell surface display, yeast display, bacterial display or mRNA display method.

Potential Ligands and Targets of the Modified Hetero-Multimeric Ubiquitin Proteins The present invention has been successfully established on the following representative antigens: ED-B, TNF-alpha, MIA-2, NGF, and IgG. It is to be understood that these antigens have only been selected to show that the presently described methods can be successfully carried out by a person skilled in the art without undue burden after having received the information provided herein. The invention is not restricted to these specific antigens but can be performed on all or at least most of ligands and target molecules known in the art. Those targets can be selected by the skilled artisan within his general knowledge of the art. The following provides general definitions of ligands and targets as well as of antigens and haptens and provides also selected examples of further potential target molecules, According to the invention, antigen shall refer to a substance capable of being bound by the presently described modified ubiquitin which function is comparable to an antibody. Alternative terms used herein are “ligands”, “binding partner”, or “target”. The modified ubiquitin proteins of the invention provide binding molecules which act in a similar way as an antibody avoiding at the same time its disadvantages. The term antigen comprises haptens, peptides, proteins, sugars, DNA etc. From the Roche Lexikon Medizin (4th edition; Urban & Fischer/Elsevier GmbH) the following definitions of antigen and hapten can be obtained which are also used in the present description:

Antigen (AG): Designation for any substance recognized as foreign ("not self") by the immune system. Initiates in most case an immune reaction leading to immunity (="immunogen"); in the case of allergy (="allergen") and atopy ("atopigen"), respectively, this immune reaction is exaggerated. The AG induces a humoral (antigen-antibody reaction) and/or cellular defense reaction (see below immunity). If the AG is tolerated by the immune system (immune tolerance) it is also referred to as a "tolerogen". Effective as an antigen are mainly complex and higher molecular weight substances (protein bodies, polysaccharides, nucleotides and many synthetic compounds) having chemically identifiable functionalities (determinant) responsible for the immune response. Classified as 1) complete AG, mostly of higher molecular weight and able to arise an immune reaction by itself, 2) as a low molecular weight hapten (=half antigen) which acts as an immunogen only after it is coupled to a larger carrier molecule. Referred to e.g. as xeno-, allo- or isogenic, autologous AG; auto-, hetero, transplantation, anti-tumor virus AG.

Hapten: simple, low molecular weight chemical compound responsible for the specificity of an antigen (AG) or capable of specific binding of the antibody due to its structure (determinant), respectively, but unable to generate an allergy in contrast to a complete AG. It becomes a complete antigen after binding to a protein body called carrier.

A "ligand" or "target" or "binding partner" is a molecule that is recognized by the presently described modified heteromultimeric ubiquitin proteins. Examples of ligands that can be employed in the practice of the present invention include, but are not restricted to, agonists and antagonists for cell membrane receptors, toxins and venoms, viral epitopes, hormones, hormone receptors, polypeptides, peptides, enzymes, enzyme substrates, cofactors, drugs (e.g. opiates, steroids, etc.), lectins, sugars, polynucleotides, nucleic acids, oligosaccharides, proteins, and monoclonal antibodies.

Summarizing, as the binding partner for the modified proteins provided according to the invention all biologically and medically active and relevant molecules can be employed. Possible binding partners will be described in the following by way of example. It should be noted, however, that a plurality of other possible ligands can be added to this list. Similar to the relationship between antibody and antigen the list of potential binding partners can be completed by further potential ligands.

In this invention, examples for binding partners to heterodimeric ubiquitins are extradomain B of fibronectin (ED-B), a cytokine (tumor necrosis factor alpha) (TNF-$\alpha$), MIA-2, an immunoglobulin or a portion thereof, for example a whole antibody, (e.g. immunoglobulin G), and a growth factor (e.g. NGF, e.g. human nerve growth factor). The following provides brief descriptions of these ligands. However, it is emphasized that all of these ligands are well known in the art for years and are known by the experts in the respective technical fields. Therefore, the following descriptions are only brief summaries of some important parameters of these proteins for which also the amino acid sequences are known.

The extra-domain B (ED-B) of fibronectin is a small domain which is inserted by alternative splicing of the primary RNA transcript into the fibronectin molecule. ED-B is known to be involved in cancer and in psoriasis. Strikingly, high levels of ED-B expression were detected in primary lesions as well as metastatic sites of almost all human solid cancer entities, including breast, colorectal, non-small cell lung, pancreatic, hepatocellular, head and neck and human skin, as well as intracraneal meningioma, and glioblastoma." (Menrad u. Menssen, 2005). Furthermore, ED-B can be bound to diagnostic agents and be favorably used as diagnostic tool. One example is its use in molecular imaging of e.g. atherosclerotic plaques and detection of cancer, e.g. by immunoscintigraphy of cancer patients. Plenty of further diagnostic uses are conceivable.

The amino acid sequence of 91 amino acids of human extra-domain B (ED-B) of fibronectin is shown in SEQ ID NO: 2. For the expression of the protein, a start methionin has to be added. ED-B is conserved in mammals, e.g. in rodents, cattle, primates, carnivore, human etc. Examples of animals in which there is a 100% sequence identity to human ED-B are *Rattus norvegicus, Bos taurus, Mus musculus, Equus caballus, Macaca mulatta, Canis lupus familiaris*, and *Pan troglodytes*.

The protein MIA ("melanoma inhibitory activity", also called CD-RAP, "cartilage-derived retinoic acid-sensitive protein") is expressed in chondrocytes and was originally isolated due to its anti-proliferative properties in vitro. Originally it was detected in cell culture supernatant of melanoma cells and isolated there from. After purification and partial sequencing of the protein, a human MIA cDNA fragment was isolated with the help of degenerated primers and RT-PCR (reverse transcriptase polymerase chain reaction). Now the sequences for humane, murine, bovine, rat and Zebra fish of MIA are known. A related protein, MIA-2 is described in EP1410803B1 and US-2010/0212037. These documents are incorporated herein by reference.

Tumor Necrosis Factor-alpha (TNF-alpha), a pleiotropic cytokine, is produced mainly by macrophages, but other types of cells also produce it. TNF-alpha demonstrates beneficial as well as pathological activities. It has both growth stimulating effects and growth inhibitory properties, besides being self-regulatory. The beneficial functions of TNF-alpha include maintaining homeostasis by regulating the body's circadian rhythm, mounting an immune response to bacterial, viral, fungal and parasitic infections, replacing or remodeling injured tissue by stimulating fibroblast growth and, as the name suggests, killing certain tumors. TNF-alpha has been implicated as a mediator in a large variety of diseases.

Nerve growth factor (NGF) is a secreted protein that was discovered over 50 years ago as a molecule that promotes the survival and differentiation of sensory and sympathetic neurons. NGF is a member of a family of neurotrophic factors known as neurotrophins. NGF binds with high affinity to a tropomyosin receptor kinase known as TrkA. NGF is also capable of binding a receptor known as p75, a member of the tumor necrosis factor receptor superfamily, which also interacts with other neurotrophins. The beta chain of NGF is solely responsible for the nerve growth stimulating activity of NGF. The beta chain homodimerizes and is incorporated into a larger protein complex. The structure and function of NGF is reviewed in, for example, Sofroniew, M. V. et al. (2001) Annu. Rev. Neurosci. 24:1217-1281; Weismann, C. and de Vos, A. M. (2001) Cell. Mol. Life Sci. 58:748-759; Fahnestock, M. (1991) Curr. Top. Microbiol. Immunol. 165:1-26.

IgG antibodies are large molecules of about 150 kDa composed of 4 peptide chains. It contains 2 identical heavy chains of about 50 kDa and 2 identical light chains of about 25 kDa, thus tetrameric quaternary structure. The two heavy chains are linked to each other and to a light chain each by disulfide bonds. The resulting tetramer has two identical halves which together form the Y-like shape. Each end of the fork contains an identical antigen binding site. The Fc regions of IgGs bear a highly conserved N-glycosylation site. The N-glycans attached to this site are predominantly core-fucosylated diantennary structures of the complex type. Additionally, small amounts of these N-glycans also bear bisecting GlcNAc and α-2,6 linked sialic acids residues Methods of Selecting, Enriching and Characterizing the Displayed Proteins Selection of the hetero-multimeric modified ubiquitins with respect to their binding activities to a given ligand with a specific binding affinity of Kd in a range of $10^{-7}$-$10^{-12}$ M can be performed by means of methods known to those skilled in the art. For this purpose, the ubiquitin variations presented e.g. on the ribosomal complexes can be transiently immobilized to target substance bound e.g. on microtiter plates or can be bound to magnetic particles after binding in solution, respectively. Following separation of non-binding variations the genetic information of variations with binding activity can be specifically eluted in the form of the mRNA by destruction of the ribosomal complex. The elution is preferably carried out with EDTA. The mRNA obtained in this manner can be isolated and reverse transcribed into DNA using suitable methods (reverse transcriptase reaction), and the DNA obtained in this manner can be re-amplified.

By means of successive cycles of in vitro transcription/translation, selection, and amplification ubiquitin variations with binding properties for a predetermined hapten or antigen can be enriched.

The further characterization of the ubiquitin variations obtained in this manner can be performed in the form of a soluble protein as detailed above after cloning of the corresponding gene cassette into a suitable expression vector. The appropriate methods are known to those skilled in the art or described in the literature.

Preferably, the step of detection of the proteins having a binding affinity with respect to a predetermined binding partner is followed by a step of isolation and/or enrichment of the detected protein.

Following the expression of the ubiquitin protein modified according to the invention, it can be further purified and enriched by methods known per se. The selected methods depend on several factors known per se to those skilled in the art, for example the expression vector used, the host organism, the intended field of use, the size of the protein and other factors. For simplified purification the protein modified according to the invention can be fused to other peptide sequences having an increased affinity to separation materials. Preferably, such fusions are selected that do not have a detrimental effect on the functionality of the ubiquitin protein or can be separated after the purification due to the introduction of specific protease cleavage sites. Such methods are also known se to those skilled in the art.

Unmodified and Modified Ubiquitin Proteins as Starting Point for Mutagenesis

The terms "protein capable of binding" or "binding protein" refer to an ubiquitin protein comprising one binding region as further defined below. The binding region can refer to at least two binding determining regions ("BDR"). Each monomer has at least one binding determining region; at least two monomers form a multimer having at least two binding determining regions which form one binding region towards one antigen. Any such binding protein based on ubiquitin may comprise additional protein domains that are not binding domains, such as, for example, multimerization moieties, polypeptide tags, polypeptide linkers and/or non-proteinaceous polymer molecules. Some examples of non-proteinaceous polymer molecules are hydroxyethyl starch, polyethylene glycol, polypropylene glycol, or polyoxyalkylene.

Further multimerization of the hetero-multimeric modified ubiquitin proteins can be also performed for example by posttranslationally fusing the hetero-multimeric modified ubiquitin protein to effector molecules having a multimerization domain (for example, TNF-α). In a still further embodiment, further multimerization is performed by using a polyethylene glycol (PEG) linker. In a still further embodiment said multimerization domain also acts as pharmaceutically active component; one example is TNF-alpha acting both as multimerization domain and as pharmaceutical component Modified Hetero-Multimeric Ubiquitin Proteins The term "a modified ubiquitin protein" refers to modifications of the ubiquitin protein by any one of substitutions insertions or deletions of amino acids or a combination thereof while substitutions are the most preferred modifications which may be supplemented by any one of the modifications described above. The number of modifications is strictly limited as said modified monomeric ubiquitin units have an amino acid identity to SEQ ID NO: 1 of at least one of the group of 80%, at least 83%, at least 85%, at least 83% and at least 90%. At the most, the overall number of modified amino acids, preferably substitutions in a monomeric unit is, therefore, limited to 15 amino acids corresponding to 80% amino acid identity. Further alternatives are 13, 12, 11, 10, 9, 8, 7, 6, or 5 modified amino acids. The total number of modified amino acids in the dimeric ubiquitin molecule, preferably substitutions is 30 amino acids corresponding to 20% amino acid modifications based on the dimeric protein. Further alternatives are 28, 26, 24, 22, 20, 18, 16, 14, 13, 12, 11, 10, 9, 8, 7, 6, or 5 modified amino acids in the dimeric ubiquitin molecule The amino acid identity of the dimeric modified ubiquitin protein compared to a dimeric ubiquitin consisting of two unmodified monomeric ubiquitin proteins with a basic monomeric sequence of SEQ ID NO: 1 is selected from at least one of the group of 80%, at least 83%, at least 85%, at least 83% and at least 90%.

The modified ubiquitin proteins obtained by the method of the invention are recombinant engineered proteins with novel binding affinities to a target molecule or ligand or binding molecule (which expressions are used herein interchangeably).

The term "substitution" comprises also the chemical modification of amino acids by e.g. substituting or adding chemical groups or residues to the original amino acid. The substitution of amino acids in at least one surface-exposed region of the protein comprising amino acids located in at least one beta strand of the beta sheet region or positioned up to 3 amino acids adjacent to the beta strand is crucial.

Modification is performed by methods well-established and well-known in the art. A "randomly modified nucleotide or amino acid sequence" is a nucleotide or amino acid sequence which in a number of positions has been subjected to insertion, deletion or substitution by nucleotides or amino acids, the nature of which cannot be predicted. In many cases the random nucleotides (amino acids) or nucleotide (amino acid) sequences inserted will be "completely random" (e.g. as a consequence of randomized synthesis or PCR-mediated mutagenesis). However, the random sequences can also include sequences which have a common functional feature (e.g. reactivity with a ligand of the expression product) or the random sequences can be random in the sense that the ultimate expression product is of completely random sequence with e.g. an even distribution of the different amino acids.

In order to introduce the randomized fragments properly into the vectors, it is according to the invention preferred that the random nucleotides are introduced into the expression vector by the principle of site directed PCR-mediated mutagenesis. However, other options are known to the skilled person, and it is e.g. possible to insert synthetic random sequence libraries into the vectors as well.

To generate mutants or libraries by fusion PCR, for example three PCR reactions may carried out. Two PCR reactions are performed to generate partially overlapping intermediate fragments. A third PCR reaction is carried out to fuse the intermediate fragments.

The method for construction the library or mutant variants may include constructing a first set of primers around a desired restriction site (restriction site primer), a forward and reverse restriction primer and a second set of primers around, e.g., upstream and downstream of the codon of interest (the mutagenic primers), a forward and reverse mutagenic primer. In one embodiment, the primers are constructed immediately upstream and downstream respectively of the codon of interest. The restriction and mutagenic primers are used to construct the first intermediate and second intermediate fragments. Two PCR reactions produce these linear intermediate fragments. Each of these linear intermediate fragments comprise at least one mutated codon of interest, a flanking nucleotide sequence and a digestion site. The third PCR reaction uses the two intermediate fragments and the forward and reverse restriction primers to produce a fused linear product. The opposite, here to for unattached ends of the linear product are digested with a restriction enzyme to create cohesive ends on the linear product. The cohesive ends of the linear product are fused by use of a DNA ligase to produce a circular product, e.g., a circular polynucleotide sequence.

To construct the intermediate fragments, the design and synthesis of two sets of forward and reverse primers are performed, a first set containing a restriction enzymes digestion site together with its flanking nucleotide sequence, and the second set contains at least one variant codon of interest (mutagenic primers). Those skilled in the art will recognize that the number of variants will depend upon the number of variant amino acid modifications desired. It is contemplated by the inventor that if other restriction enzymes are used in the process, the exact location of this digestion site and the corresponding sequence of the forward and reverse primers may be altered accordingly. Other methods are available in the art and may be used instead.

Apart from having the randomized fragment of the expression product introduced into a scaffold in accordance with the present invention, it is often necessary to couple the random sequence to a fusion partner by having the randomized nucleotide sequence fused to a nucleotide sequence encoding at least one fusion partner. Such a fusion partner can e.g. facilitates expression and/or purification/isolation and/or further stabilization of the expression product.

For the purposes of purification, the fusion partner can include a purification tag such as His6 tag, myc tag, BSP biotinylation target sequence, of BirA, flu tag, lacZ, and GST. Furthermore, the fusion partner may include a sorting signal or a targeting sequence.

The substitution of amino acids for the generation of the novel binding domain specific to the target molecule can be performed according to the invention with any desired amino acid, i.e. for the modification to generate the novel binding property to the target molecule it is not mandatory to take care that the amino acids have a particular chemical property or a side chain, respectively, which is similar to that of the amino acids substituted so that any amino acid desired can be used for this purpose.

The step of modification of the selected amino acids is performed according to the invention preferably by mutagenesis on the genetic level, preferably by random mutagenesis, i.e. a random substitution of the selected amino acids. Preferably, the modification of ubiquitin is carried out by means of methods of genetic engineering for the alteration of a DNA belonging to the respective protein. Preferably, expression of the ubiquitin protein is then carried out in prokaryotic or eukaryotic organisms.

Substitutions are performed particularly in surface-exposed amino acids of the four beta strands of the beta sheets or surface exposed amino acids up to 3 amino acids adjacent to the beta sheet strand of ubiquitin protein. Each beta strand consists usually of 5-7 amino acids. With reference to SEQ ID NO: 1, for example, the beta strands of monomeric ubiquitin usually covers amino acid residues 2-7, 12-16, 41-45 and 65-71. Regions which may be additionally and preferably modified include positions up to 3 amino acids (i.e. 1, 2, or 3) adjacent to the beta sheet strand. The preferred regions which may be additionally and preferably modified include in particular amino acid residues 8-11, 62-64 and 72-75. The preferred regions include beta turns which link two beta strands together. One preferred beta-turn includes for example amino residues 62-64. A most preferred amino acid which is closely adjacent to the beta strand is the amino acid in position 8. In addition, further preferred examples for amino acid substitutions are positions 36, 44, 70, 71, and/or 73. For example, those regions which may be additionally and preferably modified include amino acids 62, 63, and 64 (3 amino acids), or 72, 73 (2 amino acids), or 8 (1 amino acid).

The number of amino acids which may be added or deleted is limited to 1, 2, 3, 4, 5, 6, 7, 8, 9 10, 11, 12, 13, 14 or more amino acids in a monomeric ubiquitin subunit, and 1, 2, 3, 4, 5, 6, 7, 8, 9, 10, 11, 12, 13, 14, 15, 16, 18, 20, 22, 24, 26 or 28 amino acids with respect to the hetero-dimeric ubiquitin protein, generally x-times the number of modifications in the monomeric protein. Generally, the number of insertions in a monomeric molecule comprises 1-10 amino acids and/or 1-7 deletions of amino acids. The number of substitutions is at least 6 and at the most 14 substitutions of amino acids per monomeric molecule. A dimeric molecule comprises altogether at least 12 and at most 28 substitutions, and/or altogether at least one and at most 20 insertions and/or at least one and at most 14 deletions. All numbers in between can be used and are encompassed by the invention, and all combinations of numbers of deletions, insertions and substitutions are possible provided that the overall structural integrity of the molecule is maintained. In one embodiment of the invention, the beta-sheet structure is maintained.

In optional embodiments, the amino acid residues are altered by amino acid substitutions. However, also deletions and insertions are allowable. The number of amino acids which may be added or deleted is limited to 1, 2, 3, 4, 5, 6, 7, 8, 9, or 10 amino acids in a monomeric ubiquitin subunit, and accordingly 1, 2, 3, 4, 5, 6, 7, 8, 9, 10, 11, 12, 13, 14, 15, 16 amino acids with respect to the dimeric ubiquitin protein. In one embodiment, no amino acid insertions are made. In a still further embodiment, no deletions have been performed.

Provided that the modified ubiquitin protein of the present invention comprises additionally to said substitutions specified in the claims and explained herein also deletions and/or additions of one or more amino acids, the amino acid positions given for wildtype human ubiquitin (SEQ ID NO: 1) have to be aligned with the modified ubiquitin in order to allot the corresponding proteins to each other. In case of fusion proteins (see below), the numbering (and alignment) of each of the monomeric ubiquitin subunits is done in the same way, i.e. an alignment of, for example, a dimer is started at amino acid position 1 for each respective subunit.

In the monomeric ubiquitin protein, preferably from mammals, e.g. human, at least 10% of the amino acids present in beta strands or positions up to 3 amino acids adjacent to the beta sheet strand, preferably at least 20%, further preferably at least 25%, can be modified, preferably substituted. At a maximum, preferably about 50% of the amino acids present in beta strands or positions up to 3 amino acids adjacent to the beta sheet strand, further preferably at a maximum about 40% or about 35% or up to about 30% or up to about 25% are modified, preferably substituted. In one beta strand, generally one to four amino acids are modified. In one embodiment, two of six amino acids in a beta strand, preferably in the first and in the fourth beta strand, e.g. region of amino acid residues 2-7 or 65-71, are modified.

A modified monomeric ubiquitin according to the invention used as building block for a hetero-multimer accounts for in total up to 20% of amino acids to be modified. Considering this, there is a sequence identity to SEQ ID NO: 1 of the modified ubiquitin protein to at least 80%. In further embodiments of the invention, the sequence identity on amino acid level is at least 83%, at least 85%, at least 87% and furthermore at least 90% at least 92% or at least 95% sequence identity to the amino acid sequence of SEQ ID NO: 1. The invention covers also amino acid sequence identities of more than 97% of the modified ubiquitin protein compared to the amino acid sequence of SEQ ID NO: 1.

In a further embodiment of the invention, an already pre-modified ubiquitin (wherein 3 or 4 or 5 or 6 or 7 amino acids in positions 2, 4, 6, 8, 62, 63, 64, 65, 66, and/or 68 of SEQ ID NO: 1 have been modified) is used as starting point for further modifications to generate a binding property to a target, and a ubiquitin is obtainable wherein in total up to 9, 10, 11, 12, 13, 14 and a maximum of 15 amino acids of the ubiquitin of SEQ ID NO: 1 are modified, preferably substituted. For example, further modifications could comprise modifications at amino acids 74 and 75 or at amino acid 45 to generate better stability or protein-chemical properties. According to an example, a modified monomeric ubiquitin as building block for a hetero-multimeric protein could be obtained in this manner having 14 substitutions and a deletion. on the total number of amino acids of ubiquitin this corresponds to a percentage of about 20%. This was extraordinarily surprising and could not be expected since usually a much lower percentage is already sufficient to disturb the folding of the protein.

In one embodiment of the invention, those amino acids are modified for the generation of a region having the novel binding properties which form a contiguous region on the surface of the protein. In this manner, a contiguous region can be generated which has a binding property to the targeted ligand. "Contiguous region" according to the invention refers to the following: due to the charge, the spatial structure and the hydrophobicity/hydrophilicity of their side chains, amino acids interact with their environment in the corresponding manner. The environment can be the solvent, generally water, or other molecules, e.g. spatially close amino acids. By means of structural information about the protein as well as the respective software the surface of the proteins can be characterized. For example, the interface region between the atoms of the protein and the solvent can be visualized in this way including the information about how this interface region is structured, which surface areas are accessible to the solvent or how the charges are distributed on the surface. A contiguous region can be revealed for example by visualization of this type using suitable software. Such methods are known to those skilled in the art. According to the invention, basically, also the whole surface-exposed region can be used as the contiguous region on the surface to be modified for the generation of novel binding properties. In one embodiment, for this purpose a modification can also comprise the α-helical region. In a hetero-dimeric modified ubiquitin protein, a binding-determining region comprises two of the surface-exposed regions forming together one contiguous region which comprises two times the length of one binding determining region.

The modification of amino acids in at least one surface-exposed region of the protein comprising at least one beta strand of the beta sheet region or positions up to 3 amino acids adjacent to the beta sheet strand is crucial. The "beta sheet structure" is defined by being essentially sheet-like and almost completely stretched. In contrast to alpha helices which are formed from an uninterrupted segment of the polypeptide chain, beta sheets can be formed by different regions of the polypeptide chain. In this way, regions spaced further apart in the primary structure can get into close proximity with each other. A beta strand typically has a length of 5-10 amino acids (usually 5-6 residues in ubiquitin) and has an almost completely stretched conformation. The beta strands come so close to each other that hydrogen bonds form between the C-0 group of one strand and the NH group of the other strand and vice versa. Beta-sheets can be formed from several strands and have a sheet-like structure wherein the position of the C alpha atoms alternates between above or below the sheet-like plane. The amino acid side chains follow this pattern and, thus, alternatively point towards the top or towards the bottom. Depending on the orientation of the beta strands the sheets are classified into parallel and antiparallel sheets. According to the invention both can be mutated and used for the preparation of the proteins claimed.

For the mutagenesis of the beta sheet structure, beta strand regions or positions up to 3 amino acids adjacent to the beta sheet strand are selected in the ubiquitin that are close to the surface. Surface-exposed amino acids can be identified with respect to the available X-ray crystallographic structure. If no crystal structure is available attempts can be made by means of computer analysis to predict surface-exposed beta sheet regions and the accessibility of individual amino acid positions with respect to the available primary structure or to model the 3d protein structure and to obtain information about potential surface-exposed amino acids in this manner. Further disclosure thereof can be taken e.g. from J. Mol. Biol., 1987 Apr. 5; 194(3):531-44. Vijay-Kumar S, Bugg C. E., Cook W. J.

It is, however, also possible to carry out modifications in the beta sheet or of positions up to 3 amino acids adjacent to the beta sheet strand for which the time-consuming pre-selection of amino acid positions to be mutagenized can be omitted. Those DNA regions encoding the beta sheet structures or up to 3 amino acids adjacent to the beta sheet strand are isolated from their DNA environment, subjected to random mutagenesis and are afterwards re-integrated into the DNA coding for the protein from which they were removed previously. This is followed by a selection process for mutants with the desired binding properties.

In another embodiment of the invention the beta strand regions or up to 3 amino acids adjacent to the beta sheet strand close to the surface are selected as already explained above and the amino acid positions to be mutagenized within these selected regions are identified. The amino acid positions selected in this way can then be mutagenized on the DNA level either by site-directed mutagenesis, i.e. a codon coding for a specific amino acid is substituted by a codon encoding another previously selected specific amino acid, or this substitution is carried out in the context of a random mutagenesis wherein the amino acid position to be substituted is defined but not the codon encoding the novel, not yet determined amino acid.

Surface-exposed amino acids are amino acids that are accessible to the surrounding solvent. If the accessibility of the amino acids in the protein is more than 8% compared to the accessibility of the amino acid in the model tripeptide Gly-X-Gly, the amino acids are called “surface-exposed”. These protein regions or individual amino acid positions, respectively, are also preferred binding sites for potential binding partners for which a selection shall be carried out according to the invention. In addition, reference is made to Caster et al., 1983 Science, 221, 709-713, and Shrake & Rupley, 1973 J Mol Biol. 79(2):351-371, which for complete disclosure are incorporated by reference in this application.

Variations of ubiquitin differing by amino acid substitutions in the region of the de novo generated artificial binding site from the parental protein and from each other can be generated by a targeted mutagenesis of the respective sequence segments. In this case, amino acids having certain properties such as polarity, charge, solubility, hydrophobicity or hydrophilicity can be replaced or substituted, respectively, by amino acids with respective other properties. Besides substitutions, the terms “mutagenesis” and “modified” and “replaced” comprise also insertions and deletions. On the protein level the modifications can also be carried out by chemical alteration of the amino acid side chains according to methods known to those skilled in the art.

Methods of Mutagenesis of Ubiquitin

As a starting point for the mutagenesis of the respective sequence segments, for example the cDNA of ubiquitin which can be prepared, altered, and amplified by methods known to those skilled in the art can be used. For site-specific alteration of ubiquitin in relatively small regions of the primary sequence (about 1-3 amino acids) commercially available reagents and methods are on hand (“Quick Change”, Stratagene; “Mutagene Phagemid in vitro Mutagenesis Kit”, Biorad). For the site-directed mutagenesis of larger regions specific embodiments of e.g. the polymerase chain reaction (PCR) are available to those skilled in the art. For this purpose a mixture of synthetic oligodeoxynucleotides having degenerated base pair compositions at the desired positions can be used for example for the introduction of the mutation. This can also be achieved by using base pair analogs which do not naturally occur in genomic DNA, such as e.g. inosine.

Starting point for the mutagenesis of one or more beta strands of the beta sheet region or positions up to 3 amino acids adjacent to the beta sheet strand can be for example the cDNA of ubiquitin or also the genomic DNA. Furthermore, the gene coding for the ubiquitin protein can also be prepared synthetically.

In one embodiment of the invention the mutagenesis is carried out by assembly of DNA oligonucleotides carrying the amino acid codon NNK. It should be understood, however, that also other codons (triplets) can be used. The mutations are performed in a way that the beta sheet structure is preferably maintained. Generally, the mutagenesis takes place on the outside of a stable beta sheet region exposed on the surface of the protein. It comprises both site-specific and random mutagenesis. Site-specific mutagenesis comprising a relatively small region in the primary structure (about 3-5 amino acids) can be generated with the commercially available kits of Stratagene® (QuickChange®) or Bio-Rad® (Mutagene® phagemid in vitro mutagenesis kit) (cf. U.S. Pat. No. 5,789,166; U.S. Pat. No. 4,873,192).

If more extended regions are subjected to site-specific mutagenesis a DNA cassette must be prepared wherein the region to be mutagenized is obtained by the assembly of oligonucleotides containing the mutated and the unchanged positions (Nord et al., 1997 Nat. Biotechnol. 8, 772-777; McConell and Hoess, 1995 J. Mol. Biol. 250, 460-470.). Random mutagenesis can be introduced by propagation of the DNA in mutator strains or by PCR amplification (error-prone PCR) (e.g. Pannekoek et al., 1993 Gene 128, 135 140). For this purpose, a polymerase with an increased error rate is used. To enhance the degree of the mutagenesis introduced or to combine different mutations, respectively, the mutations in the PCR fragments can be combined by means of DNA shuffling (Stemmer, 1994 Nature 370, 389-391). A review of these mutagenesis strategies with respect to enzymes is provided in the review of Kuchner and Arnold (1997) TIBTECH 15, 523-530. To carry out this random mutagenesis in a selected DNA region also a DNA cassette must be constructed which is used for mutagenesis.

Different procedures known per se available for mutagenesis are methods for site-specific mutagenesis, methods for random mutagenesis, mutagenesis using PCR or similar methods.

In a preferred embodiment of the invention the amino acid positions to be mutagenized are predetermined. The selection of amino acids to be modified is carried out to meet the limitations of present claim 1 with respect to those amino acids which have to be modified. In each case, a library of different mutants is generally established which is screened using methods known per se. Generally, a pre-selection of the amino acids to be modified can be particularly easily performed as sufficient structural information is available for the ubiquitin protein to be modified.

Methods for targeted mutagenesis as well as mutagenesis of longer sequence segments, for example by means of PCR, by chemical mutagenesis or using bacterial mutator strains also belong to the prior art and can be used according to the invention.

In one embodiment of the invention the mutagenesis is carried out by assembly of DNA oligonucleotides carrying the amino acid codon NNK. It should be understood, however, that also other codons (triplets) can be used. The mutations are performed in a way that the beta sheet structure is preferably maintained. Generally, the mutagenesis takes place on the outside of a stable beta sheet region exposed on the surface of the protein. It comprises both site-specific and random mutagenesis. Site-specific mutagenesis comprising a relatively small region in the primary structure (about 3-5 amino acids) can be generated with the commercially available kits of Stratagene® (QuickChange®) or Bio-Rad® (Mutagene® phagemid in vitro mutagenesis kit) (cf. U.S. Pat. No. 5,789,166; U.S. Pat. No. 4,873,192).

If more extended regions are subjected to site-specific mutagenesis a DNA cassette must be prepared wherein the region to be mutagenized is obtained by the assembly of oligonucleotides containing the mutated and the unchanged positions (Nord et al., 1997 Nat. Biotechnol. 8, 772-777; McConell and Hoess, 1995 J. Mol. Biol. 250, 460-470.). Random mutagenesis can be introduced by propagation of the DNA in mutator strains or by PCR amplification (error-prone PCR) (e.g. Pannekoek et al., 1993 Gene 128, 135 140). For this purpose, a polymerase with an increased error rate is used. To enhance the degree of the mutagenesis introduced or to combine different mutations, respectively, the mutations in the PCR fragments can be combined by means of DNA shuffling (Stemmer, 1994 Nature 370, 389-391). A review of these mutagenesis strategies with respect to enzymes is provided in the review of Kuchner and Arnold (1997) TIBTECH 15, 523-530. To carry out this random mutagenesis in a selected DNA region also a DNA cassette must be constructed which is used for mutagenesis.

Random substitution of amino acids according to one example of the present invention of at least 3, preferably at least 6 amino acids at positions 2, 4, 6, 8, 62, 63, 64, 65, 66 and/or 68 of monomeric ubiquitin can be performed particularly easily by means of PCR since the positions mentioned are localized close to the amino or the carboxy terminus of the protein. Accordingly, the codons to be manipulated are at the 5' and 3' end of the corresponding cDNA strand. Thus, the first oligodeoxynucleotide used for a mutagenic PCR reaction—apart from the codons at positions 2, 4, 6, and/or 8 to be mutated—corresponds in sequence to the coding strand for the amino terminus of ubiquitin. Accordingly, the second oligodeoxynucleotide—apart from the codons of positions 62, 63, 64, 65, 66, and/or 68 to be mutated—at least partially corresponds to the non-coding strand of the polypeptide sequence of the carboxy terminus. By means of both oligodeoxynucleotides a polymerase chain reaction can be performed using the DNA sequence encoding the monomeric ubiquitin protein as a template. Furthermore, the amplification product obtained can be added to another polymerase chain reaction using flanking oligodeoxynucleotides which introduce for example recognition sequences for restriction endonucleases. It is preferred according to the invention to introduce the gene cassette obtained into a vector system suitable for use in the subsequent selection procedure for the isolation of ubiquitin variations having binding properties to a predetermined hapten or antigen.

The substitution of amino acids for the generation of the novel binding domain specific to the selected ligand can be performed according to the invention with any desired amino acid, i.e. for the modification to generate the novel binding property to the selected ligand it is not mandatory to take care that the amino acids have a particular chemical property or a side chain, respectively, which is similar to that of the amino acids substituted so that any amino acid desired can be used for this purpose.

The step of modification of the selected amino acids is performed according to the invention preferably by mutagenesis on the genetic level by random mutagenesis, i.e. a random substitution of the selected amino acids. Preferably, the modification of ubiquitin is carried out by means of methods of genetic engineering for the alteration of a DNA belonging to the respective protein. Preferably, expression of the ubiquitin protein is then carried out in prokaryotic or eukaryotic organisms.

According to the invention, a modified ubiquitin protein can further preferably be prepared by chemical synthesis. In preferred embodiments, the amino acid residues are altered by amino acid substitutions. However, also deletions and insertions are allowable. Optionally, the number of amino acids to be inserted or deleted is 1 to 10, 1 to 5, 2, 3 or 4 amino acids. In one embodiment, no amino acid insertions are made. In a still further embodiment, no deletions have been performed.

After having made the modifications above, the inventors have found the amino acid modified ubiquitin sequences described in the examples which bind their targets with very high affinity (Kd values up to $10^{-10}$ M).

Regions to be Modified in Ubiquitin

The regions for modification can be basically selected as to whether they can be accessible for as the selected binding partner and whether the overall structure of the protein will presumably show tolerance to a modification.

Besides modifications in surface-exposed beta strands also modifications in other surface-exposed regions of the protein can be carried out, preferably in positions up to 3 amino acids adjacent to the beta strand. These modified regions are involved in the newly generated binding with high affinity to a target.

According to another preferred embodiment of the present invention at least 3 or 4 or 6, optionally at least 8, 10, 12 and maximal 15 surface-exposed amino acids of ubiquitin, preferably mammalian or human ubiquitin, can be modified in the monomeric ubiquitin wherein a substitution is preferred as the modification. This comprises the modification of 3, 4, 5, 6, 7, 8, 9, 10, 11, 12, 13, 14, or 15 surface-exposed amino acids of ubiquitin. These at least 3 and maximal 15 surface-exposed modified amino acids then form the region with binding affinity to the predetermined binding partner. This region is defined herein as "binding domain region" ("BDR"). In this respect, it is particularly preferred that at least 2, optionally at least 4, further optionally at least 6, 8, 10, 12 and maximal 15 of the surface-exposed amino acids are in a beta sheet region, i.e. in a beta sheet strand or distributed on several beta strands or positions up to 3 amino acids adjacent to a beta sheet strand. It is further preferred that at least 3 of all modified, preferably substituted, amino acids are directly adjacent to each other in the primary sequence.

In another optional embodiment of the present invention amino acids in one or two, preferably two of the four beta strands in the protein or positions up to 3 amino acids adjacent to preferably two of the four beta strands are modified to generate a novel binding property. Also optional is a modification in three or four of the four beta strands or positions up to 3 amino acids adjacent to three or four of the beta strands for the generation of a binding to a selected target or ligand.

It is particularly preferred that amino acids in the amino-terminal and carboxy-terminal strand or in positions up to 3 amino acids adjacent to the amino-terminal and carboxy-terminal strand are modified, preferably substituted, to generate a novel binding site to the ligand or target. In this respect, it is particularly preferred that up to 3 amino acids adjacent to the carboxy-terminal beta sheet strand are modified, preferably substituted, and up to 1 amino acid adjacent to the amino-terminal beta sheet strand is modified, preferably substituted.

According to the invention ubiquitin is modified in its amino acids, preferably by substitution, in at least three amino acids of the following positions of a mammalian ubiquitin, preferably human ubiquitin: 2, 4, 6, 8, 62, 63, 64, 65, 66, 68. These at least three amino acids from said group of amino acids form a contiguous surface-exposed region on the surface of ubiquitin which were found to be particularly suitable for the generation of modified proteins having a binding affinity that did not exist previously with respect to a specific binding partner, e.g. ED-B, TNFalpha, NGF, IgG, MIA-2, or any other target. At least three of these amino acid residues have to be modified. Optionally 3, 4, 5, 6, 7, 8, 9 or 10 of said amino acid residues are modified, preferably substituted, optionally in combination with additional amino acid residues.

For the purpose of determining the extent of sequence identity of a derivative of the ubiquitin to the amino acid sequence of SEQ ID NO: 1, for example, the SIM Local similarity program can be employed (Xiaoquin Huang and Webb Miller, "Advances in Applied Mathematics, vol. 12: 337-357, 1991), freely available from the authors and their institute for multiple alignment analysis Clustal, W. can be used (Thompson et al., Nucleic Acids Res., 22(22): 4673-4680, 1994.). Preferably, the extent of the sequence identity of the derivative to SEQ ID NO: 1 is determined relative to the complete sequence of SEQ ID NO: 1.

The methods for determining the binding affinities are known per se and can be selected for instance from the following methods: ELISA, Surface Plasmon Resonance (SPR) based technology, offered for instance by Biacore®, size exclusion chromatography, fluorescence anisotropy, fluorescence spectroscopy and isothermal titration calorimetry (ITC).

In a still further aspect, the invention relates to a fusion protein comprising a hetero-multimeric binding protein of the invention fused to a pharmaceutically and/or diagnostically active component; reference is made for instance to U.S. Pat. No. 7,838,629 the complete contents thereof is incorporated by reference.

A fusion protein of the invention may comprise non-polypeptide components, e.g. non-peptidic linkers, non-peptidic ligands, e.g. for therapeutically or diagnostically relevant radionuclides. It may also comprise small organic or non-amino acid based compounds, e.g. a sugar, oligo- or polysaccharide, fatty acid, etc. In one preferred embodiment of the invention, the ubiquitin-based binding molecule is linked to a peptidic, amino acid-based linker or ligand or a protein having therapeutically or diagnostically relevant properties.

Binding Specificities (Dissociation Constants)

The binding specificities of the fusion proteins according to the invention are as defined above for the non-fusion protein given in Kd. In accordance with the invention, the term “Kd” defines the specific binding affinity which is in accordance with the invention in the range of $10^{-7}$-$10^{-12}$ M. A value of $10^{-5}$ M and below can be considered as a quantifiable binding affinity. Depending on the application a value of $10^{-7}$ M to $10^{-11}$ M is preferred for e.g. chromatographic applications or $10^{-9}$ to $10^{-12}$ M for e.g. diagnostic or therapeutic applications. Further preferred binding affinities are in the range of $10^{-7}$ to $10^{-10}$ M, preferably to $10^{-11}$ M.

Multimerization of Ubiquitin

According to the invention at least two differently modified ubiquitin monomers genetically linked by head-to-tail fusion bind to the same epitope of the target molecule, e.g. ED-B, TNFalpha, IgG, Mia-2, NGF or any other target molecule, and are only effective if both binding domain regions act together. Or in other words, they bind to the same epitope via a single contiguous binding region which is formed by the acting together of both binding regions of the two modules.

The monomers can be connected directly or via linkers. Suitable preferred linkers are those of SEQ ID NO: 32 or [A2] having at least the sequence GIG or having at least the sequence SGGGG or any other linker, for example GIG, SGGGG, SGGGGIG, SGGGGSGGGGIG or SGGGGSGGGG. However, there are many conceivable linkers which can be used instead.

Libraries

In a further aspect, the present invention is directed to a library containing DNA encoding for modified monomeric ubiquitin proteins as defined above which forms the basis for providing the hetero-multimeric, preferrably hetero-dimeric ubiquitin proteins of the invention.

In a still further aspect of the invention, a fusion library containing DNA obtained by fusing two libraries as specified above is provided; each library encodes for differently modified monomeric ubiquitin protein units in order to obtain hetero-dimeric ubiquitin fusion proteins, the monomeric units thereof being linked together in a head-to-tail arrangement. Said library encoding for hetero-dimeric fusion proteins of ubiquitin exhibits a monovalent binding activity with respect to a given target Said linking together is performed either by using anyone of the linkers known by the skilled artisan or a linker described herein. “Differently modified” also includes the alternative of one unmodified molecule being present in the hetero-dimeric protein.

Example 1 outlines the production of a complex library. However, care must be taken regarding the quality of such a library. Quality of a library in scaffold technology is in the first place dependent from its complexity (number of individual variants) as well as functionality (structural and protein-chemical integrity of the resulting candidates). Both characteristics, however, may exert negative influences on each other: enhancing the complexity of a library by increasing the number of modified positions on the scaffold might lead to a deterioration of the protein-chemical characteristics of the variants. This might result in a decreased solubility, aggregation and/or low yields. A reason for this is the larger deviation from native scaffolds having an energetically favourable protein packaging.

Therefore, it is a balancing act to construct such a scaffold library suitably between the extreme positions of introducing as many variations as possible into the original sequence in order to optimize it for a target and, on the other hand, of conserving the original primary sequence as much as possible in order to avoid negative protein-chemical effects.

Specific Modifications in Hetero-Dimeric Ubiquitin Proteins

The hetero-dimer of ubiquitin according to the invention binding to a ligand with Kd=$10^{-7}$-$10^{-12}$ M and exhibiting a monovalent binding activity with respect to said ligand is selected from the following two alternatives:

(1) in the first monomeric unit substitutions at least in amino acid positions 6, 8, 63, 64, 65, and 66; and in the second monomeric unit substitutions at least in amino acid positions 6, 8, 62, 63, 64, 65, and 66; optionally additionally 2, and (2) in the first monomeric unit substitutions at least in amino acid positions 2, 4, 6, 62, 63, 64, 65, and 66; and in the second monomeric unit substitutions at least in amino acid positions 6, 8, 62, 63, 64, 65, and 66; optionally additionally 2.

In one embodiment, the fusion protein is a genetically fused dimer of said ubiquitin protein having amino acids substitutions in positions 6, 8, 63-66 of the first ubiquitin monomer and substitutions in amino acid residues in positions 6, 8, 62-66, and optionally in position 2 of the second ubiquitin monomer, preferably in the first ubiquitin monomer substitutions Lysine (K) to Tryptophane (W) or Phenylalanine (F) in position 6, Leucine (L) to Tryptophane or Phenylalanine (W, F) in position 8, Lysine (K) to Arginine (R) or Histidine (H) in Position 63, Glutamic acid (E) to Lysine (K), Arginine (R) or Histidine (H) in position 64, Serine (S) to Phenylalanine (F) or Tryptophane (W) in position 65 and Threonine (T) to Proline (P) in position 66;

in the second ubiquitin monomer, the substitutions

Lysine (K) to Threonine (T), Asparagine (N), Serine (S) or Glutamine (Q) in position 6, Leucine (L) to Glutamine (Q) or Threonine (T) or Asparagine (N) or Serine (S) in position 8, Glutamine (Q) to Trytophane (W) or Phenylalanine (F) in position 62, Lysine (K) to Serine (S), Threonine (T), Asparagine (N) or Glutamine (Q) in position 63, Glutamic acid (E) to Asparagine (N), Serine (S), Threonine (T), or Glutamine (Q) in position 64, Serine (S) to Phenylalanine (F) or Tryptophane (W) in position 65, and Threonine (T) to Glutamic acid (E) or Aspartic acid (D) in position 66, and Optionally Glutamine (Q) to Arginine (R), Histidine (H) or Lysine (K) in position 2 are preferred.

These alternative substitutions in each monomer can be combined with each other without any limitations provided that the resulting modified ubiquitin hetero-dimers show a specific binding affinity to said ligand of Kd=$10^{-7}$-$10^{-12}$M and exhibit a monovalent binding activity with respect to said ligand and provided that the structural stability of the ubiquitin protein is not destroyed or hampered.

Most preferred are the following substitutions:

(1) in the first monomeric unit at least K6W, LBW, K63R, E64K, S65F, and T66P;

and in the second monomeric unit at least K6T, L8Q, Q62W, K63S, E64N, S65W, and T66E; optionally additionally Q2R, or (2) in the first monomeric unit at least Q2T, F4W, K6H, Q62N, K63F, E64K, S65L, and T66S;

and in the second monomeric unit modifications at least in positions 6, 8, 62, 63, 64, 65, and 66, further optionally in the second monomeric unit at least—K6X, L8X, Q62X, K63X, E64X, S65X, and T66X; optionally additionally Q2X, wherein X can be any amino acid.

Particularly preferred are the following substitutions in the first ubiquitin monomer to generate binding proteins for ED-B:

2: Q→T, 4: F→W, 6: K→H, 62: Q→N, 63: K→F, 64: E→K, 65: S→L, 66: T→S.

Either no linker or any linker can be used to connect the two monomers head-to-tail. Preferred linkers are those of SEQ ID NO: 32 or the sequence GIG or SGGGGIG or SGGGGSGGGGIG.

In a preferred embodiment, a ubiquitin hetero-dimer with two binding determining regions acting together for binding the ligand ED-B comprises the amino acid sequence of SEQ ID NO: 33 or 34. A preferred fusion protein of the invention comprising TNF-alpha as a pharmaceutically active component has the sequence of SEQ ID NO: 35 or 36. In another embodiment, a ubiquitin hetero-dimer with two binding determining regions acting together for binding the ligand ED-B comprises the amino acid sequence of FIG. 11 corresponding to SEQ ID NO: XX.

A further preferred protein is provided by the following sequence wherein XXXX may be any amino acid (SEQ ID NO: 47).

```
MTIWVHTLTGKTITLEVEPSDTIENVKAKIQDKEGIPPDQQRLIWAGKQL
EDGRTLSDYNINFKLSLHLVLRLRGGSGGGGSGGGGIG
MQIFVXTXTGKTITLEVEPSDTIENVKAKIQDKEGIPPDQQRLIWAGKQL
EDGRTLSDYNIXXXXXLHLVLRLRGG
```

Examples of proteins with these sequences are shown in FIG. 11. As linker, SGGGGSGGGGIG was used here: It is to be understood that also other kind of linkers or no linker are feasible alternatives.

Polynucleotides, Host Cells Vectors of the Invention

In a further aspect of the invention, the present invention covers also polynucleotides which encode for a protein or fusion protein as described before. Additionally, vectors comprising said polynucleotide are covered by the invention.

In an additional aspect of the present invention, host cells are covered which comprise a protein or a fusion protein described herein and/or a polynucleotide coding for said recombinant protein or fusion protein of the invention or a vector containing said polynucleotide.

Uses of the Modified Hetero-Multimeric Ubiquitin Molecules

The modified ubiquitin proteins of the invention capable of binding a ligand with high affinity are to be used for instance for preparing diagnostic means for in vitro or in vivo use as well as therapeutic means. The proteins according to the invention can be used e.g. as direct effector molecules (modulator, antagonist, agonist) or antigen-recognizing domains.

In the field of human and veterinary medical therapy and prophylaxis pharmaceutically effective medicaments containing at least one heterodimeric ubiquitin protein modified in accordance with the invention can be prepared by methods known per se. Depending on the galenic preparation these compositions can be administered parentally by injection or infusion, systemically, rectally, intraperitoneally, intramuscularly, subcutaneously, transdermally or by other conventionally employed methods of application. The type of pharmaceutical preparation depends on the type of disease to be treated, the severity of the disease, the patient to be treated and other factors known to those skilled in the art of medicine.

Depending on the selected fusion partner the pharmaceutical composition of the invention is adapted to be directed to the treatment of diseases in which the target is abundant.

The compositions are adapted to contain a therapeutically effective dose. The quantity of the dose to be administered depends on the organism to be treated, the type of disease, the age and weight of the patient and further factors known per se.

The compositions contain a pharmaceutically or diagnostically acceptable carrier and optionally can contain further auxiliary agents and excipients known per se. These include for example but not limited to stabilizing agents, surface-active agents, salts, buffers, colouring agents etc.

The pharmaceutical composition can be in the form of a liquid preparation, a cream, a lotion for topical application, an aerosol, in the form of powders, granules, tablets, suppositories, or capsules, in the form of an emulsion or a liposomal preparation. The compositions are preferably sterile, non-pyrogenic and isotonic and contain the pharmaceutically conventional and acceptable additives known per se. Additionally, reference is made to the regulations of the U.S. Pharmacopoeia or Remington's Pharmaceutical Sciences, Mac Publishing Company (1990).

A "pharmaceutical composition" according to the invention may be present in the form of a composition, wherein the different active ingredients and diluents and/or carriers are in admixed with each other, or may take the form of a combined preparation, where the active ingredients are present in partially or totally distinct form. An example for such a combination or combined preparation is a kit-of-parts.

A "composition" according to the present invention comprises at least two pharmaceutically active compounds. These compounds can be administered simultaneously or separately with a time gap of one minute to several days. The compounds can be administered via the same route or differently; e.g. oral administration of one active compound and parenteral administration of another are possible. Also, the active compounds may be formulated in one medicament, e.g. in one infusion solution or as a kit comprising both compounds formulated separately. Also, it is possible that both compounds are present in two or more packages.

In a further embodiment, the pharmaceutical composition is in the form of a kit of parts, providing separated entities for the recombinant ubiquitin protein/fusion protein of the invention and for the one or more chemotherapeutic agents.

The modified ubiquitin proteins according to the invention may be prepared by any of the many conventional and well known techniques such as plain organic synthetic strategies, solid phase-assisted synthesis techniques or by commercially available automated synthesizers. On the other hand, they may also be prepared by conventional recombinant techniques alone or in combination with conventional synthetic techniques.

Optionally, the modifications may be performed by genetic engineering on the DNA level and expression of the modified protein in prokaryotic or eukaryotic organisms or in vitro.

In a further embodiment, said modification step includes a chemical synthesis step.

In one aspect of the invention, said population of differently modified proteins is obtained by genetically fusing two DNA libraries encoding each for differently modified monomeric ubiquitin proteins.

BRIEF DESCRIPTION OF THE FIGURES

FIG. 1 shows that the recombination of a front (first) modified ubiquitin monomer with a binding determining region referred to as BDR1 with a different modified rear (second) ubiquitin monomer with a binding determining region referred to as BDR2 to generate a hetero-dimer results in an significant increase of affinity to ED-B as well as an increase of the specificity of binding. The modified ubiquitin molecules are analyzed via Biacore®, fluorescence anisotropy, binding on cells, and tissue sections. Shown are concentration dependent ELISAs (con.-ELISA) of the binding of several hetero-dimeric ubiquitin variants to human ED-B.

FIG. 1 A shows a binding affinity of Kd=9.4 μM=9.45×$10^{-6}$ M for the monomer 41B10 (here: SPWF28-41B10th). The closed circles show the binding of the first monomer 41B10 to the fragment 67B89 which represent the extradomain-B of fibronectin. The control fragment 6789 does not contain ED-B and is shown in open circles.

FIG. 1 B shows the binding affinity of a hetero-dimeric ubiquitin. The hetero-dimer contains as first monomer of 41B10 combined with a different second monomer resulting in variant 46H9 (here: SPWF28-46H9th). The binding affinity of 46H9 is much increased compared to the monomer shown in FIG. 1 A due to the monovalent binding of both monomers to the target ED-B (Kd=131 nM=1.3×$10^{-7}$ M; here shown as 67B89, closed circles). The control fragment 6789 does not contain ED-B and is shown in open circles.

FIG. 2 shows the affinity and activity of a modified ubiquitin based ED-B binding hetero-dimer molecule fused to a cytokine.

FIG. 2A shows the high affinity of modified ubiquitin based ED-B binding hetero-dimer 24H12 (Kd 50.7 nM=5×$10^{-8}$ M). The closed circles show the binding of 24H12 to EDB; as negative control, the binding of 24H12 to BSA (bovine serum albumin) was used (open circles).

FIG. 2B shows the increased affinity of modified ubiquitin based ED-B binding heterodimer 24H12 fused to cytokine TNFalpha to result in a multimerization of the hetero-dimer 24H12 (Kd=5.6 nM=5.6×$10^{-9}$ M.)

FIG. 2C shows an analysis of exemplary candidates from a hetero-dimeric modified ubiquitin library selection, for example hetero-dimer variants 9E12, 22D1, 24H12, and 41B10. The Kd ELISA values are increased for the target ED-B compared to cytosolic fibronectin (c-FN) used as control, confirming a specific binding to the target.

FIG. 3 shows the contribution of different modified ubiquitin based variants to binding affinity and specificity. The different variants share common sequence modules which are marked with lower case letters. The variants were analyzed with respect to their ED-B binding. FIG. 3 shows different combinations of monomers resulting in modified ubiquitin-heterodimers. Hetero-dimeric variants 46-A5, 50-G11 and 46-H4 have all the same first (front) modified monomer with BDR1 (labeled with the letter "a" in the figure), but a second (rear) ubiquitin monomer modified in different positions with BDR2. Variants 52-D10 and 52-B3 have a different first (front) modified monomer compared to 46-H9 with BDR1, but the same second (rear) ubiquitin monomer with BDR2 (labeled with the letter "e").

Figure 2D:
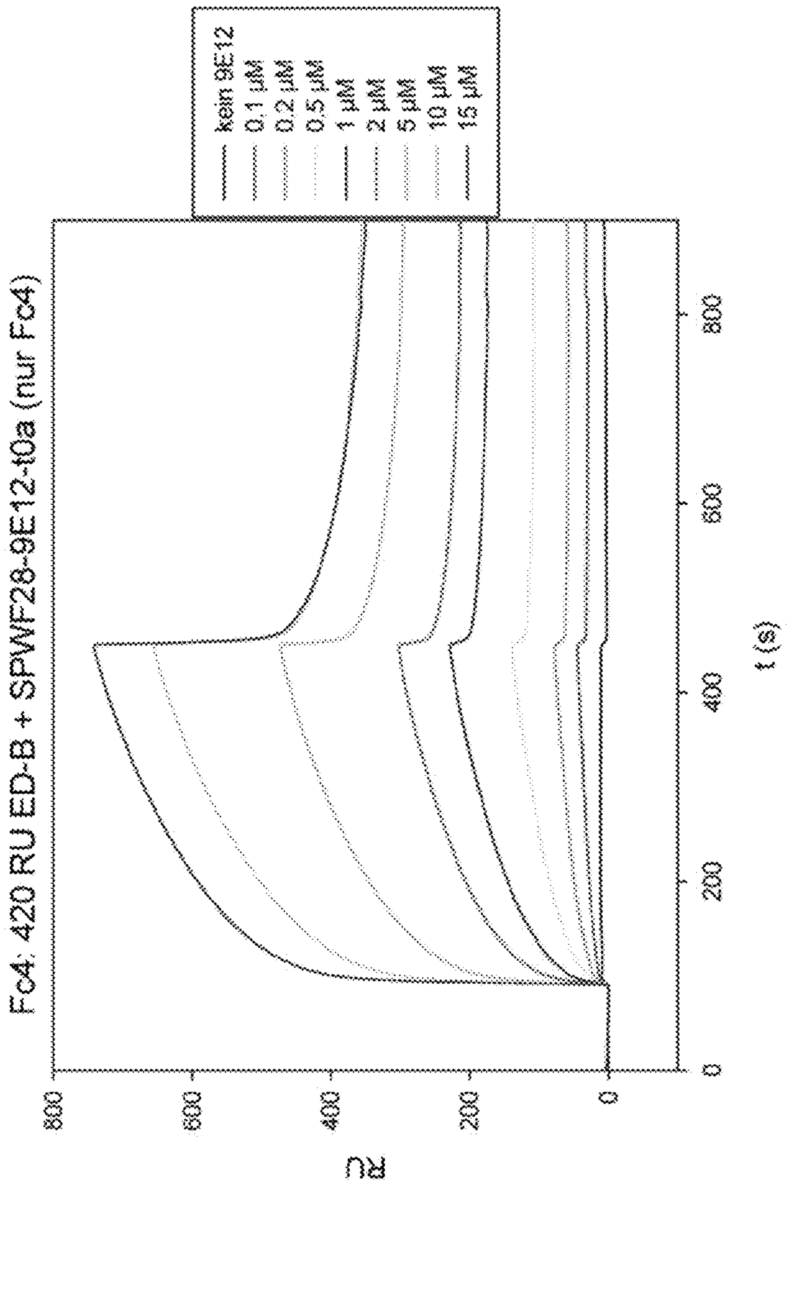
FIG. 2D shows results of an analysis of the modified hetero-dimeric ubiquitin molecule 9E12 via label-free interaction assays using Biacore®. Different concentrations of the hetero-dimeric ubiquitin variants were analyzed (see figure legend: 0-15 microM of 9E12) for binding to ED-B immobilized on a chip (Biacore) to analyze the interaction between the hetero-dimeric variant 9E12 and ED-B. A Kd could not be determined from analyzing the association and dissociation curves.
Figure 2E:
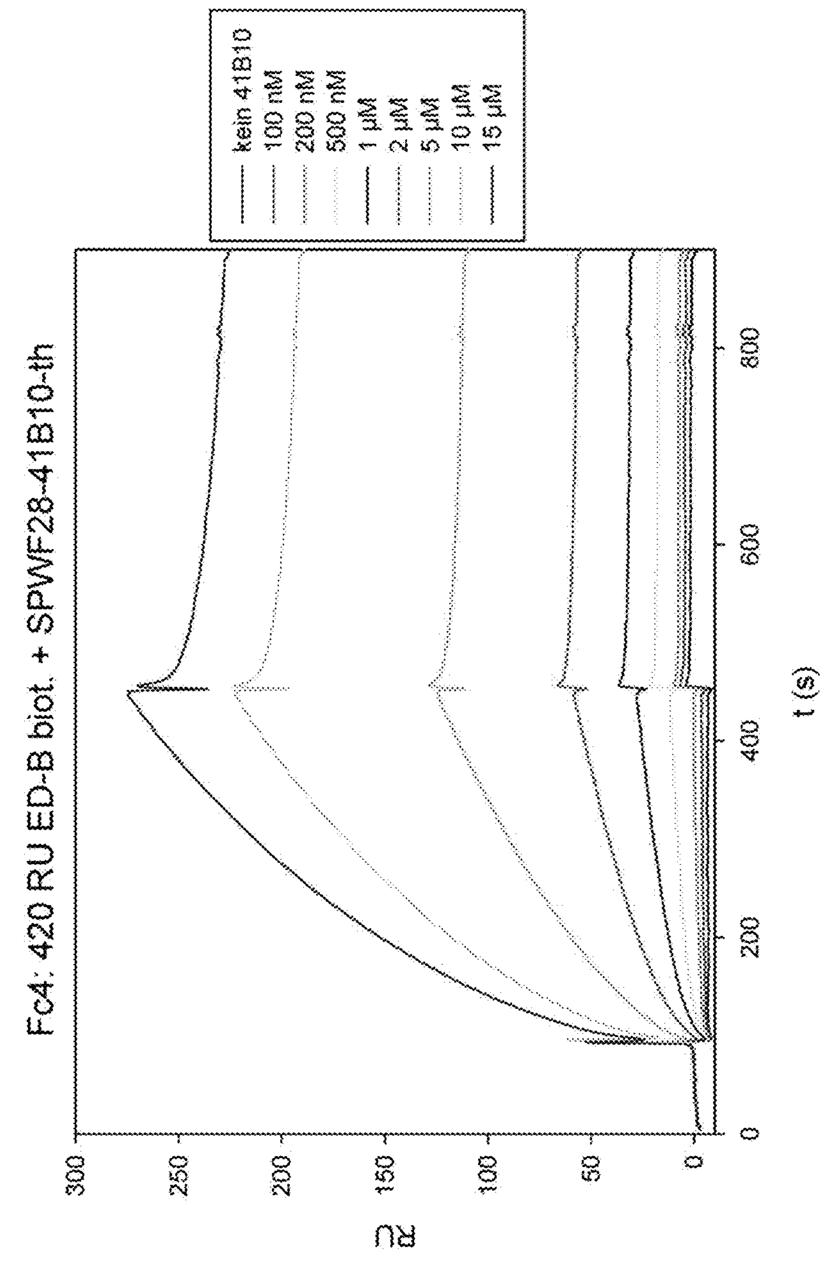
FIG. 2E shows results of an analysis of the modified hetero-dimeric ubiquitin molecule 41B10 via label-free interaction assays using Biacore®. Different concentrations of the hetero-dimeric ubiquitin variants were analyzed (see figure legend: 0-15 microM of 41B10) for binding to ED-B immobilized on a chip (Biacore) to analyze the interaction between the hetero-dimeric variant 41B10 and ED-B. Analyzing the association and dissociation curves resulted in a Kd of 623 nM (6.2×$10^{-7}$ M).

The modified ubiquitin hetero-dimers have the following sequences:

46-H4: SEQ ID NO: 25, 45-H9: SEQ ID NO: 26, 46-A5: SEQ ID NO: 27, 50-G11: SEQ ID NO: 28, 52-B3: SEQ ID NO: 29, 52-D10: SEQ ID NO: 30

The above described sequences were modified in the course of the experiments by adding a His-Tag with the sequence LEHHHHHH (SEQ ID NO: 31).

As can be seen from FIG. 3, 46-H4 has an excellent binding affinity to ED-B (Kd=189 nM); 46-A5 and 52-D10 have no binding activity while other modified ubiquitin proteins provide a minor binding activity compared 46-H4 to ED-B. Thus it can be concluded that both monomers in a hetero-dimeric variant are required for a high affinity binding to a target; both monomers show a monovalent binding to the target.

The modified ubiquitin hetero-dimer with high ED-B binding activity named 46 H9 is identified by the following amino acid replacements in both binding domain region in the two monomers as compared to wild type ubiquitin monomers:

in the first module (BDR1) (a) Q2G, F4V, K6R, Q62P, K63H, E64A, S65T, T66L in the second module (BDR2) (e) K6H, L8M, Q62K, K63P, E64I, S65A, T66E

50G11 in the first module (46H9)(a) Q2G, F4V, K6R, Q62P, K63H, E64P, S65T, T66L in the second module (c) K6M L8R, Q62M, K63N, E64A, S65R, T66L

46H4 in the first module (46H9)(a) Q2G, F4V, K6R, Q62P, K63H, E64P, S65T, T66L in the second module (d) K6G, LBW, Q62T, K63Q, E64Q, S65T, T66R

52B3 in the first module (g) Q2R, F4P, K6Y, Q62P, K63P, E64F, S65A, T66R in the second module (46H9) K6H, L8M, Q62K, K63P, E64I, S65A, T66E 52D10 (non-ED-B binder)

in the first module Q2V, F4C, K6R, Q62T, K63A, E64P, S65G, T66D in the second module (46H9) (e) K6H, L8M, Q62K, K63P, E64I, S65A, T66E 46A5 (non-ED-B binder)

in the first module (46H9)(a) Q2G, F4V, K6R, Q62P, K63H, E64P, S65T, T66L in the second module (b) K6L, L8M, Q62L, K63A, E64F, S65A, FIG. 4 shows a sequence alignment. Line 1: Two monomers of the wild type ubiquitin protein ($1^{st}$ line) are linked with a 12-amino acid linker SGGGGSGGGGIG starting at Position 77 and ending at Position 88; the second monomer with BDR2 starts at position 89 with a Methionine. This dimeric wild-type ubiquitin protein is aligned with the modified ubiquitin hetero-dimeric variant 46-H9 ($2^{nd}$ line) with different modifications in the first and in the second monomer resulting in two BDR's. Both BDRs act together in the binding of the target due to a monovalent binding to the target.

FIG. 5 shows a sequence alignment of modified ubiquitin hetero-dimeric variant 1041-D11 ($1^{st}$ line) to "Ub2_TsX9" (ubiquitin modified in position 45 in both monomers to Tryptophane, showing the linker GIG between the two monomers (position 77 to 79; the second monomer starts with a Methionine at Position 80), and an exchange from Glycine to Alanine at the last c-terminal amino acids of the $2^{nd}$ monomer. The third line shows "Ubi-Dimer wt", the wildtype ubiquitin as dimer; showing no linker alignment (thus, the second monomer starts at position 77 with a Methionin). The $4^{th}$ line shows the "Ubi-Monomer wt" which is the human wild type ubiquitin.

Figure 6:
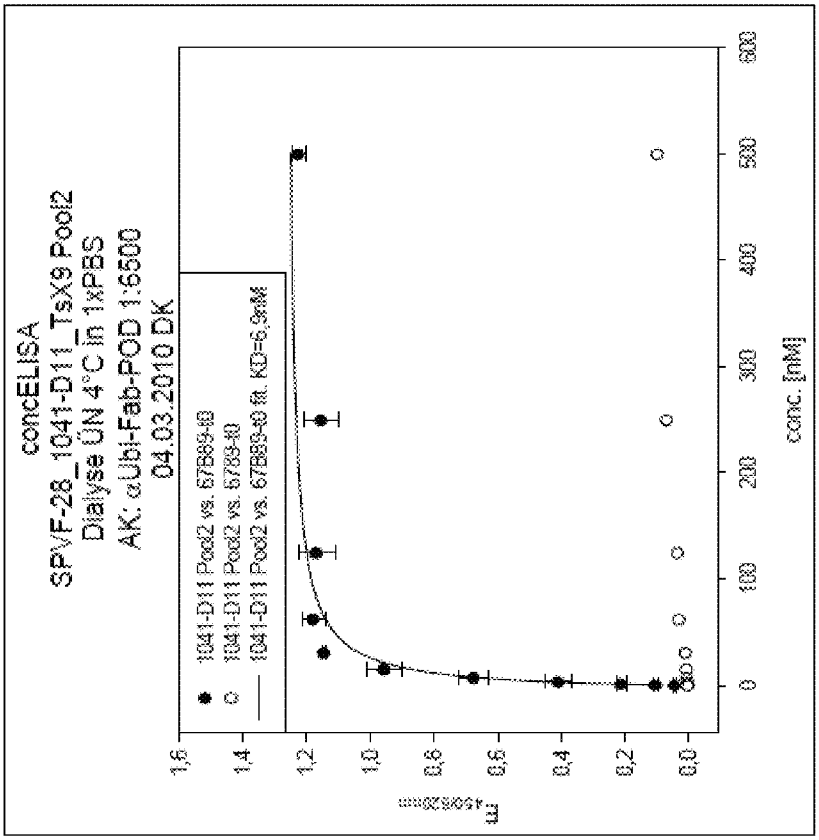

FIG. 6 shows a concentration dependent ELISA of the binding of the hetero-dimeric ubiquitin variant 1041-D11 to human ED-B. Variant 1041-D11 shows very high affinity binding to ED-B (Kd=6.9 nM=$6.9\times10^{-9}$ M). The closed dots show the affinity of the binding of hetero-dimeric ubiquitin variant 1041-D11 to an ED-B containing fibronectin fragment (referred to as 67B8940) compared to no binding of this variant to negative control (referred to as 678940) (open circles).

Figure 7:
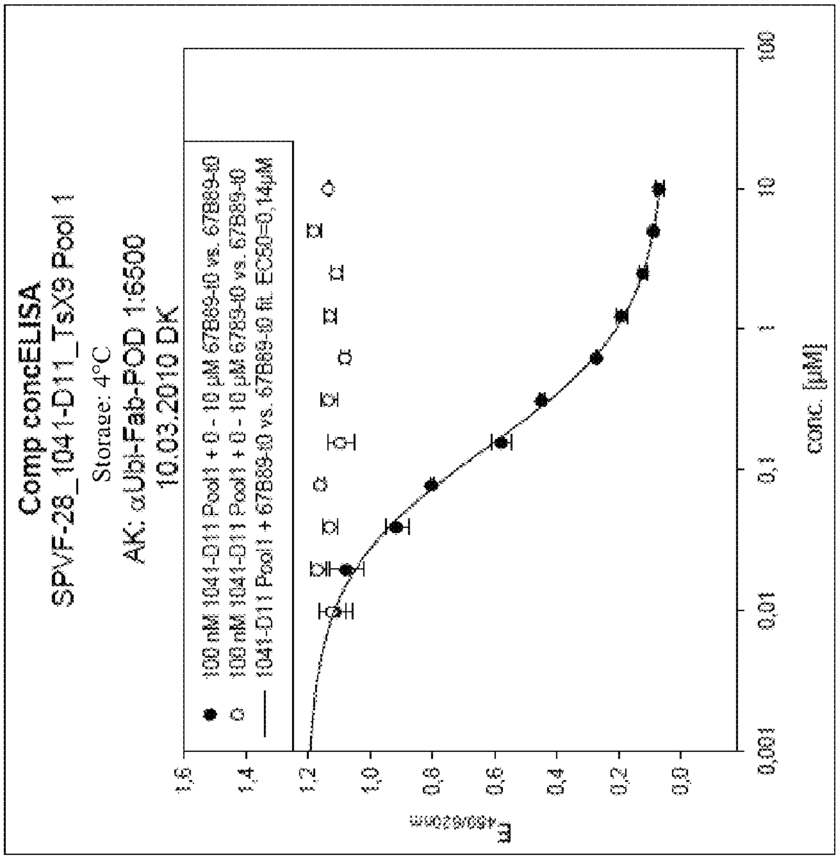

FIG. 7 shows competitive concentration dependent ELISAs of the binding of hetero-dimeric ubiquitin variant 1041-D11 to immobilized ED-B containing fibronectin fragment (67B89) in the presence of increasing amounts of free target. 1041-D11 dissociates from immobilized 67B89 with an IC50 of 140 nM of soluble 67B89 indicating that binding of 1041-D11 is not an artefact of ED-B structural deterioration due to immobilization on a hydrophobic surface used in conc-ELISA setup.

Figure 8:
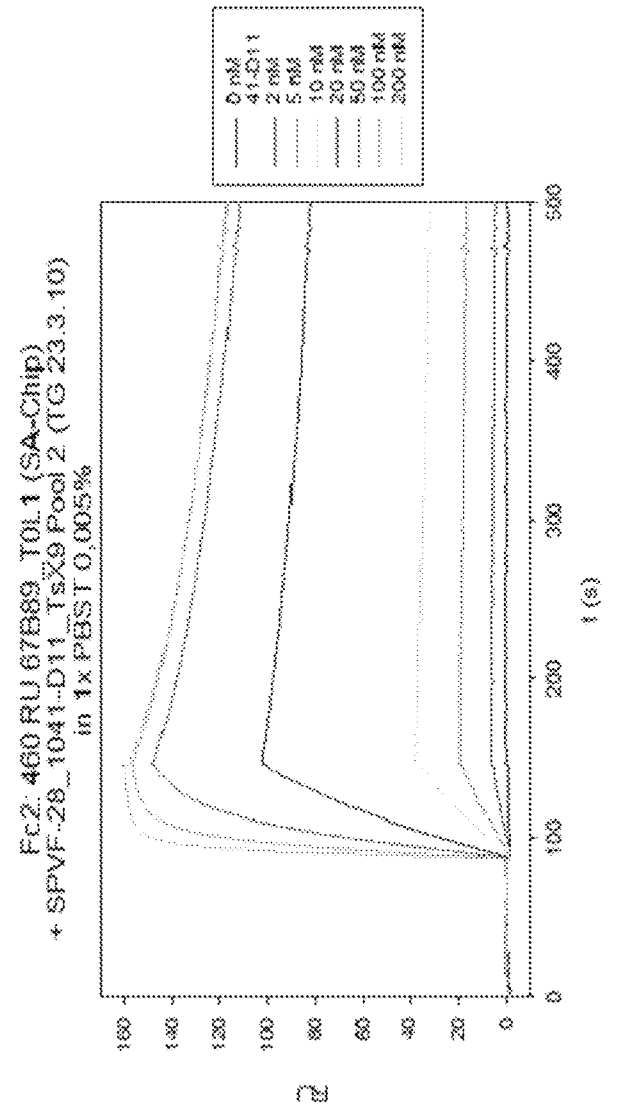

FIG. 8 shows a result of an analysis of the modified hetero-dimeric ubiquitin molecule 1041-D11 in label-free interaction assays using Biacore®. Different concentrations of the hetero-dimeric ubiquitin variant were analyzed (see figure legend: 0-200 nM of 1041-D11) for binding to an ED-B containing fibronectin fragment (referred to as 67B89) immobilized on a SA-chip (Biacore). Analyzing the association and dissociation curves resulted in a Kd of 1 nM ($1\times10^{-9}$ M) and a $k_{off}$ rate of $7.7\times10^{-4}$ $s^{-1}$ which indicates a long half time of an complex of 1041-D11 and ED-B.

Figure 9:
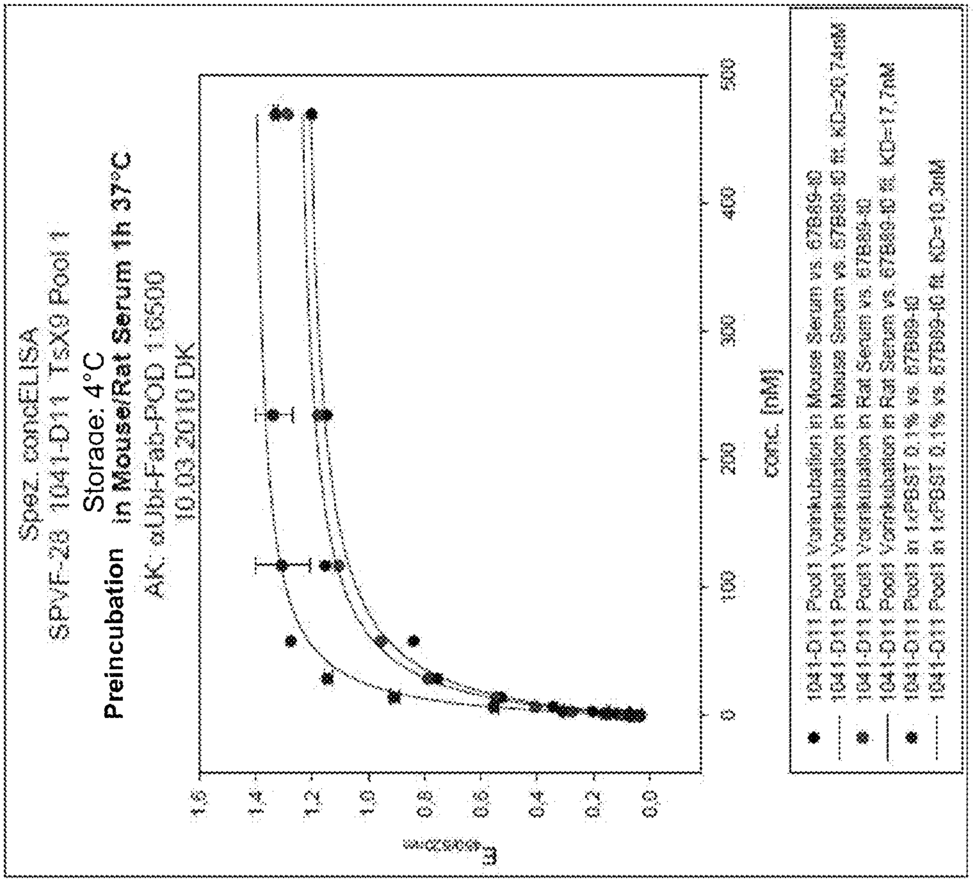

FIG. 9 shows the binding of hetero-dimeric ubiquitin variant 1041-D11 to ED-B in a concentration dependent ELISA simultaneously analyzing the serum-stability of binding activity. Shown are different conditions, such as pre-incubation for 1 h at 37° C. of the variant in mouse or rat serum or in PBST as control. The Kd-values are all between 10 and 20 nM. Thus, it can be concluded that the binding of the hetero-dimer 1041-D11 to ED-B is not significantly influenced by blood serum.

FIG. 10 shows an analysis of the complex-formation of hetero-dimeric ubiquitin variant 1041-D11 with fibronectin fragments by SE-HPLC.

FIG. 10 A shows complex formation of 1041-D11 with ED-B. Three HPLC runs are overlaid: the blue peak with a retention time of 21.651 min originates from pure 1041-D11; the black peak with a retention time of 26.289 min represents the fibronectin fragment 67B89; a mixture of 1041-D11 and 67B89 results in the red peak with a retention time of 21.407 min after SE-HPLC. The shift of the 1041-D11 peak to a lower retention time as well as the disappearance of the 67B89 peak indicates formation of a complex of 1041-D11 and soluble ED-B.

FIG. 10 B shows the overlay of three SE-HPLC runs of 1041-D11 (blue, 21.944 min), fibronectin fragment 6789 without ED-B (black, 26.289 min) and a mixture of 1041-D11 and 6789 (red line with peaks at 21.929 min and 26.289 min). Almost no shift of the 1041-D11 peak is observed. This fact together with a lack of disappearance of the 6789 peak indicates no significant binding of the ED-B free fibronectin fragment 6789.

Figure 11:
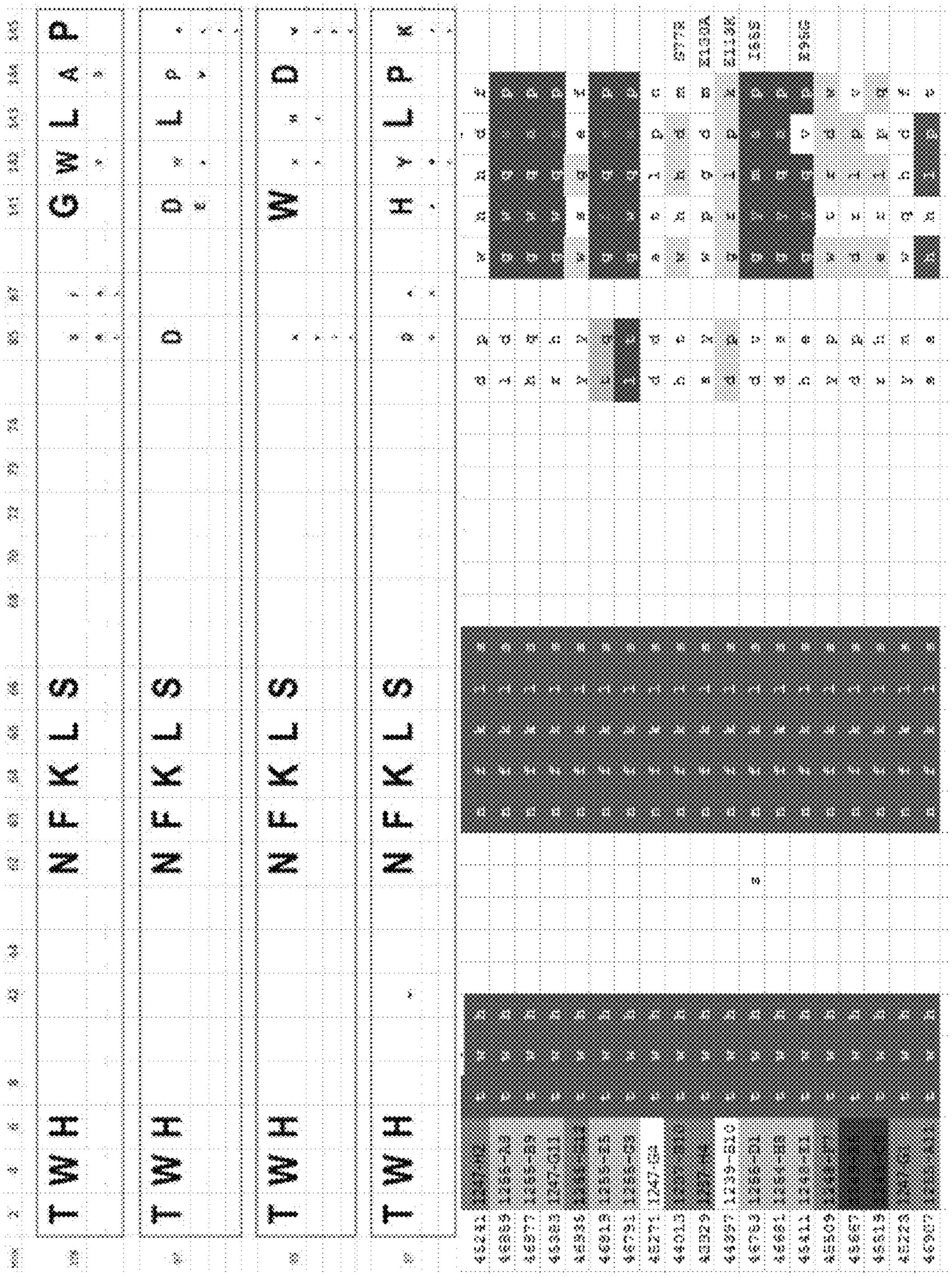

FIG. 11 shows the consensus positions and amino acid substitutions of ED-B binding variants. 16 representative hetero-dimeric sequences are shown which have been found to have surprisingly strong binding affinities to ED-B. The consensus amino acid positions are in the first monomeric binding determining region 2, 4, 6, 62, 63, 64, 65, 66 while the consensus amino acid substitutions are Q2T, F4W, K6H, Q62N, K63F, E64K, S65L, and T66S.

Figure 12:
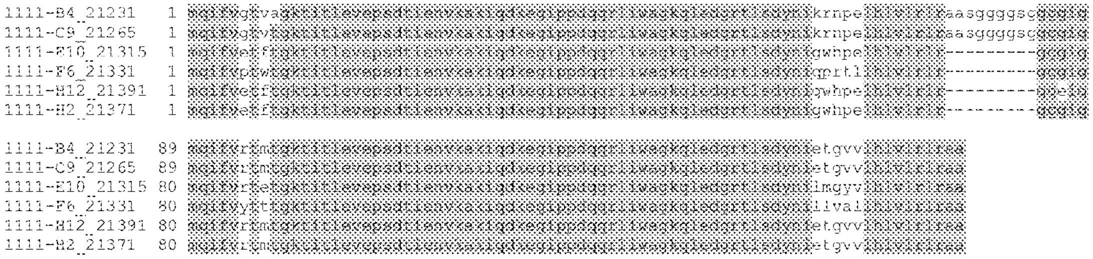

FIG. 12 shows an sequence alignment six ubiquitin-based hetero-dimeric MIA2 binding proteins. The second ubiquitin monomer starts with a Methionine in Position 89 (1111-B4, 1111-C9) or in position 80 (1111-E10, 1111-F6, 1111-H12, 1111-H2).

FIG. 13 shows the alignment of the binding determining regions BDR1 and BDR2 as well as the linkers of the ubiquitin-based hetero-dimeric MIA2 binding proteins of FIG. 12. Also shown are additional amino acid exchanges in the ubiquitin sequence.

Figure 14:
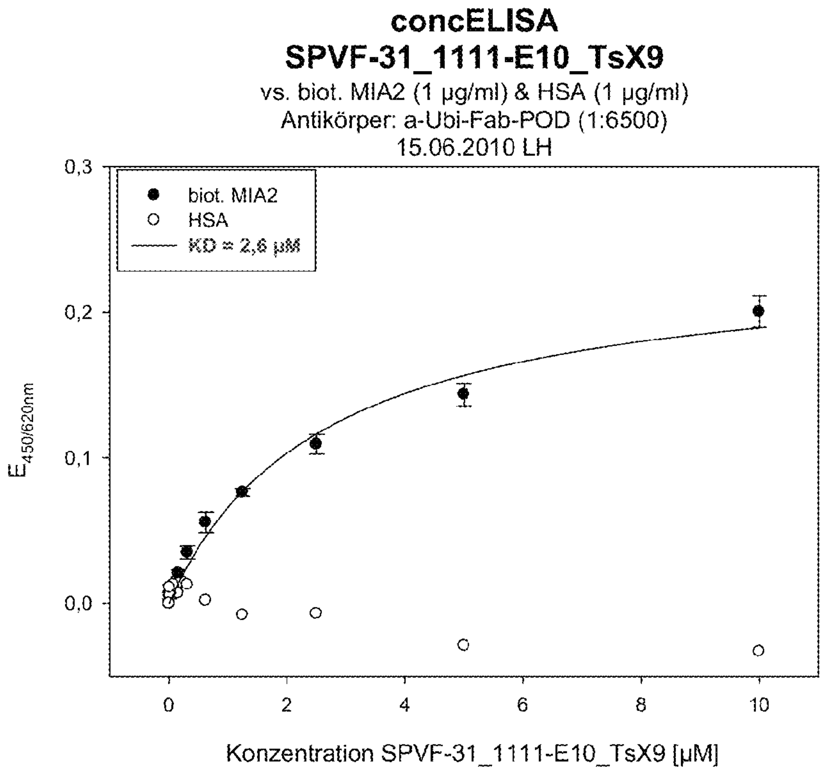

FIG. 14 shows a concentration-dependent ELISA of the binding variant 1111-E10 of FIG. 12 to biotinylated MIA-2 (biot. MIA2), Kd=2.6 microM (closed circles); control human serum albumin (HSA) (open circles).

Figure 15:
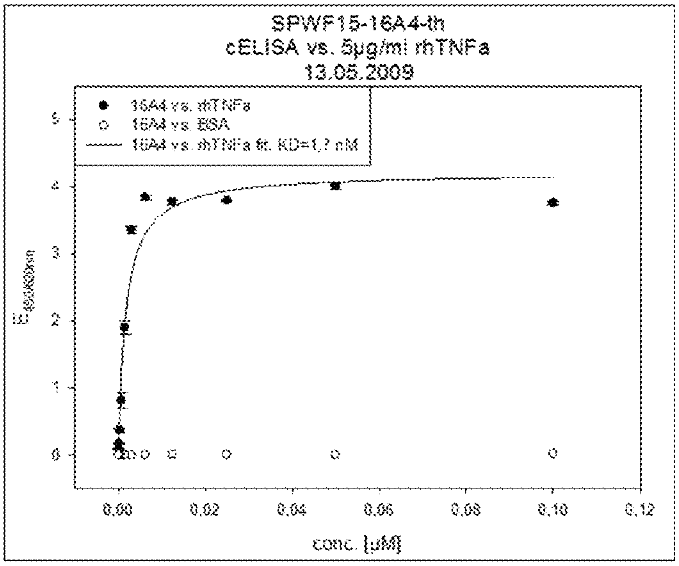

FIG. 15 A. Modifications were made in amino acid residues in a series of molecules of the first and second monomeric ubiquitin units and sequence alignments were performed to evaluate the most potent binding sites. Part A shows the sequence information for the first and Part B for the second monomeric modified ubiquitin unit.

FIG. 15 B. [KHa3] Modifications are in positions 2, 4, 6, 62-66, 68 of the first ubiquitin monomer and in positions 6, 8, 62-66 in the second monomer. Linker between the two ubiquitin monomers: SGGGGSGGGGIG.

FIG. 15 C. Shown is a concentration dependent ELISA of the binding of the hetero-dimeric ubiquitin variant SPWF-15_6-A12 to human TNFalpha. Binding protein SPWF-15_6-A12 shows very high affinity binding to TNFalpha (Kd=12 nM=$1.2\times10^{-8}$ M). The figure shows the high affinity binding against human TNFalpha (closed circles); control BSA (open circles).

FIG. 15 D. Sequence of the heterodimeric ubiquitin binding protein SPWF-15__16-D4_Th with specificity for TNFalpha. Modifications are in positions 2, 4, 6, 62-66 of the first ubiquitin monomer and in positions 6, 8, 62-66 in the second monomer. Linker between the two ubiquitin monomers: SGGGGSGGGGIG.

FIG. 15 E. Shown is a concentration dependent ELISA of the binding of the hetero-dimeric ubiquitin variant SPWF-15__16-D4_Th to human TNFalpha. Binding protein SPWF-15__6-A12 shows very high affinity binding to TNFalpha (Kd=1.7 nM=$1.7\times10^{-9}$ M). The Figure shows the binding against human TNFalpha (closed circles); control: bovine serum albumin (BSA) (open circles).

Figure 16:
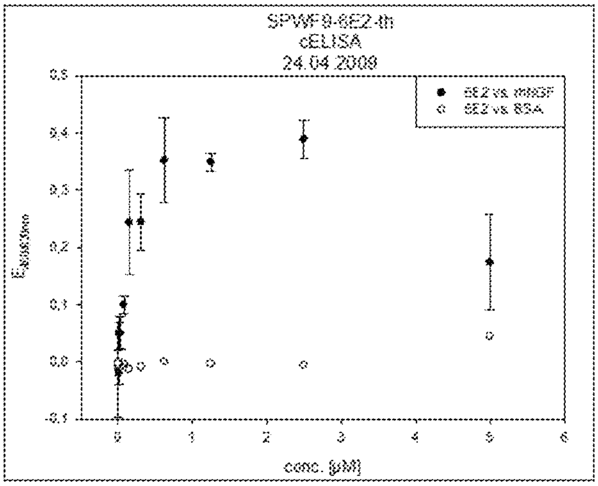

FIG. 16 shows NGF binding of modified ubiquitin-based heterodimers

FIG. 16A. Sequence of the heterodimeric ubiquitin binding protein SPWF9-1B7-th with specificity for NGF. Modifications are in positions 2, 4, 6, 62-66 and in position 51 of the first ubiquitin monomer and in positions 6, 8, 62-66 in the second monomer. Linker between the two ubiquitin monomers: SGGGGSGGGGIG.

FIG. 16B. Concentration-dependent ELISA determines the high affinity binding of Kd 0.9 μM=$9\times10^{-7}$ M) to NGF. The Figure shown the binding against recombinant human NGF (rhNGF; closed circles); control BSA (open circles).

FIG. 16C. Sequence of the heterodimeric ubiquitin binding protein SPWF9-6A2-th with specificity for NGF. Modifications are in positions 2, 4, 6, 62-66 of the first ubiquitin monomer and in positions 6, 8, 62, 64-66 in the second monomer. Linker between the two ubiquitin monomers: SGGGGSGGGGIG.

FIG. 16D. Concentration-dependent ELISA determines the high affinity binding of Kd 180 nM=$1.8\times10^{-7}$ M). to NGF. The Figure shown the binding against recombinant human NGF (rhNGF; closed circles); control BSA (open circles).

Figure 17:
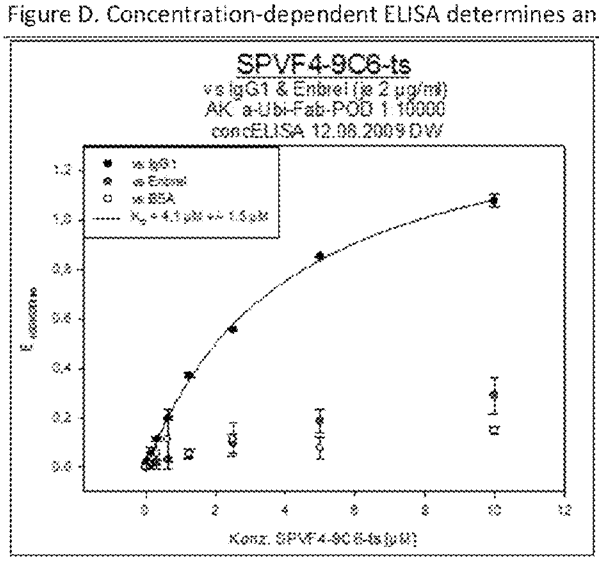

FIG. 17 Heterodimeric IgG binding proteins.

FIG. 17A. Sequence of the heterodimeric ubiquitin binding protein SPVF4-16B2-ts with specificity for IgG. Modifications are in positions 6, 62, 63, 65, 66 of the first ubiquitin monomer and in positions 6, 62-66 in the second monomer. Linker between the two ubiquitin monomers: SGGGGSGGGGIG.

FIG. 17B. Concentration-dependent ELISA determines affinity binding of Kd 3.8 μM to IgG. The Figure shown the binding against IgG (closed black circles); control BSA-1, BSA-2 and Enbrel (red, green and blue circles without fitted line). Enbrel bears the $F_c$ moiety of human IgG1. Weak binding to Enbrel indicates binding of SPVF4-16B2-ts to th $F_{ab}$ moiety of IgG.

FIG. 17C. Sequence of the heterodimeric ubiquitin binding protein SPVF4-9C6-ts with specificity for IgG. Modifications are in positions 6, 8, 62-66 of the first ubiquitin monomer and in positions 6, 8, 62-66 in the second monomer. Linker between the two ubiquitin monomers: SGGGGSGGGGIG.

FIG. 17D. Concentration-dependent ELISA determines the affinity binding of Kd 4.1 μM to IgG. The Figure shows the binding against IgG (closed black circles); control BSA (open circles) and Etanercept (trade name Enbrel) (red circles, without fitted line). Enbrel bears the $F_c$ moiety of human IgG1. Weak binding to Enbrel indicates binding of SPVF4-9C6-ts to th $F_{ab}$ moiety of IgG.

EXAMPLES

The following Examples are provided for further illustration of the invention. The invention is particularly demonstrated with respect to the modification of ubiquitin as an example. The invention, however, is not limited thereto, and the following Examples merely show the practicability of the invention on the basis of the above description. For a complete disclosure of the invention reference is made also to the literature cited in the application and in the annex which are all incorporated in their entirety into the application by reference.

Example 1

Identification of Hetero-Dimeric ED-B Binding Proteins Based on Modified Ubiquitin Proteins Library Construction and Cloning Unless otherwise indicated, established recombinant genetic methods were used, for example as described in Sambrook et al.

A random library of human ubiquitin hetero-dimers with high complexity was prepared by concerted mutagenesis of in total 15 selected amino acid positions. The modified amino acids, which were substituted by NNK triplets, comprised at least 3 amino acids selected from positions 2, 4, 6, 8, 62, 63, 64, 65, 66, 68 within the first ubiquitin monomer and at least 3 amino acids selected from positions 2, 4, 6, 8, 62, 63, 64, 65, 66, 68 within the second ubiquitin monomer. Both ubiquitin monomers were genetically linked (head to tail) by a Glycine/Serine linker with at least the sequence GIG or by Glycine/Serine linker with at least the sequence SGGGG, for example GIG, SGGGG, SGGGGIG, SGGGGSGGGGIG (SEQ ID NO: 32) or SGGGGSGGGG, but any other linker is possible.

TAT Phage Display Selection

The heterodimeric ubiquitin library was enriched against the target using, for example, TAT phage display as selection system. Other selection methods known in the art can be used. The target can be immobilized nonspecifically onto protein binding surfaces or via biotinylated residues which were covalently coupled to the protein. The immobilization via biotin onto streptavidin beads or neutravidin strips is preferred. The target-binding phages are selected either in solution or on immobilized target; for example, the biotinylated and immobilized target with phage was incubated followed by washing of the phages bound to the matrix and by elution of matrix-bound phages. In each cycle following target incubation, the beads were magnetically separated from solution and washed several times. In selection cycle one to three, ternary complexes immobilized on target-loaded magnetic beads were washed. In the fourth selection cycle washing was performed several times. In the first selection cycle the biotinylated target was immobilized to neutravidin strips whereas in cycles two to four selections in solution was performed followed by immobilization of target-phage complexes on Streptavidin-coated Dynabeads® (Invitrogen). After washing in the first two selection cycles, the beads were again magnetically separated from solution and the phages of target-binding modified ubiquitin molecules were released by elution with acidic solution. In selection cycles three and four elution of phages was carried out by competitive elution with excess target. The eluted phages were reamplified. To direct specificity of binders a protein similar to the target can be included during selection.

Alternatively to TAT Phage Display Selection: Ribosome Display Selection

The ubiquitin library was enriched against the target using, for example, ribosome display as selection system (Zahnd et al., 2007), Ohashi et al., 2007). Other selection methods known in the art can be used. The target was biotinylated according to standard methods and immobilized on Streptavidin-coated Dynabeads® (Invitrogen). Ternary complexes comprising ribosomes, mRNA and nascent ubiquitin polypeptide were assembled using the PURExpress™ In Vitro Protein Synthesis Kit (NEB). Two primary rounds of selection were performed, wherein ternary complexes were incubated followed by two similar rounds of selection. In each cycle following target incubation, the beads were magnetically separated from solution and washed with ribosome display buffer with increasing stringency. In selection cycle one to three, ternary complexes immobilized on target-loaded magnetic beads were washed. In the fourth selection cycle washing was performed several times. After washing in the first two selection cycles, the beads were again magnetically separated from solution and mRNA of target-binding modified ubiquitin molecules was released from ribosomes by addition of 50 mM EDTA. In selection cycles three and four elution of mRNA was carried out by competitive elution with excess target (Lipovsek and Pluckthun, 2004). After each cycle, RNA purification and cDNA synthesis were performed using RNeasy MinElute Cleanup Kit (Qiagen, Germany), Turbo DNA-free Kit (Applied Biosystems, USA) and Transcriptor Reverse Transcriptase (Roche, Germany).

Cloning of Enriched Pools

After the fourth selection cycle the synthesized cDNA was amplified by PCR according to method known in the art, cut with appropriate restriction nucleases and ligated into expression vector pET-20b(+) (Merck, Germany) via compatible cohesive ends.

Single Colony Hit Analysis

After transformation into NovaBlue(DE3) cells (Merck, Germany) ampicillin-resistant single colonies were grown. expression of the target-binding modified ubiquitin was achieved by cultivation in 96-well deep well plates (Genetix, UK) using auto induction medium (Studier, 2005). Cells were harvested and subsequently lysed. After centrifugation the resulting supernatants were screened by ELISA coated with target and a ubiquitin-specific Fab fragment conjugated with horseradish peroxidase (POD). As detecting reagent TMB-Plus (Biotrend, Germany) was used and the yellow colour was developed using 0.2 M $H_2SO_4$ solution and measured in a plate reader at 450 nm versus 620 nm.

Several cycles of selection display versus target were carried out. In the last two cycles of selection binding molecules were eluted with an excess of free target.

For example, hetero-dimeric modified ubiquitin binding proteins against the target ED-B were identified, such as 46H9 (SEQ ID NO: 6), 9E12 (SEQ ID NO: 7), 22D1 (SEQ ID NO: 8), 1041-D11 FIG. 5 (SEQ ID NO: 33), 1045-D10 (SEQ ID NO: 34). For example, hetero-dimeric modified ubiquitin binding proteins against other target were identified, for example against the target MIA-2 binding protein 1111-E10 FIG. 12 (SEQ ID NO: 53), against the target TNFalpha binding proteins SPWF-15_6-A12 FIG. 15B (SEQ ID NO: 57) and SPWF-15_16-D4 FIG. 15D (SEQ ID NO: 90), against the target NGF binding proteins SPWF9-1B7-th FIG. 16A (SEQ ID NO: 91) and SPWF9-6A2-th FIG. 16C (SEQ ID NO: 92) and against the target IgG binding proteins SPVF4-16B2-ts FIG. 17A (SEQ ID NO: 93) and SPVF4-9C6-ts FIG. 17C (SEQ ID NO: 94).

A sequence alignment of wild type ubiquitin monomer (Ubi monomer wt), with wild type ubiquitin dimer (ubi dimer wt) and wild type ubiquitin protein (Ub2-TsX9 in FIG. 5, with an exchange in Position 45 of each monomer and with two substitutions at the C-terminus) with the modified ubiquitin hetero-dimeric variant 1041-D11 is shown in FIG. 5. In Ub2-TsX the substitutions at the C-terminus (GG to AA) of the monomer increase the stability in serum because deubiquitinases cleave behind the GG of ubiquitin but not behind the AA. The secondary structure of the wild type ubiquitin compared to the ubiquitin with these substitutions at the C-terminus is almost identical.

The modified ubiquitins with superior ED-B binding activity referred to as 1041-D11 (shown in FIGURE X; SEQ ID NO: 36) or 1045-D10 are identified by the following amino acid replacements as compared to the wild type: in the first module: K6W, LBW, K63R, E64K, S65F, T66P; in the second module: K6T, L8Q, Q62W, K63S, E64N, S65W, T66E; optionally Q2R (in variant 1041-D11, but not in variant 1045-D10). Suitable preferred linkers for the fusion protein are linkers having at least the sequence GIG or having at least the sequence SGGGG or any other linker, for example GIG, SGGGG, SGGGGIG, SGGGGSGGGGIG or SGGGGSGGGG. However, there are many conceivable linkers which can be used instead. Further EDB binders with their consensus sequence in the first monomeric binding determining region are shown in FIG. 11.

Modified ubiquitins with superior MIA-2 binding activity are shown in FIGS. 12-14.

Modified ubiquitins with superior NGF binding activity are shown in FIG. 16.

Modified ubiquitins with superior TNFalpha binding activity are shown in FIG. 15.

Modified ubiquitins with superior IgG binding activity are shown in FIG. 17.

Example 2

Binding Analysis of Modified Ubiquitin-Based ED-B Binding Variants to Human Target

Example 2A

Binding Analysis of Modified Ubiquitin-Based Binding Variants by Concentration Dependent ELISA Binding of ubiquitin-based variants to human target was assayed by a concentration dependent ELISA. Increasing amounts of purified protein applied to NUNC-medisorp plates coated with human target, BSA or HSA and possible further controls, such as cellular fibronectin (cFN) if ED-B was used as target. Antigen coating with 50 μl protein solution (10 μg/ml) per well was performed at 4° C. overnight. After washing the plates with PBS, 0.1% Tween 20 pH 7.4 (PBST) the wells were blocked using blocking solution (PBS pH 7.4; 3% BSA; 0.5% Tween 20) at RT for 2 h. Wells were washed again three times with PBST and then three times with PBS. Coated wells were incubated with different concentrations of target binding protein at RT for 1 h. After washing the wells with PBST, anti-Ubi fab fragment (AbyD) POD conjugates were applied in an appropriate dilution in PBST. The plate was washed three times with PBST. 50 μl TMB substrate solution (KEM-EN-Tec) was added to each well and incubated for 15 min. The reaction was stopped by adding 0.2 M $H_2SO_4$. The ELISA plates were read out using the TECAN Sunrise ELISA-Reader. The photometric absorbance measurements were done at 450 nm using 620 nm as a reference wavelength. FIG. 6 shows very high affinity binding of variant 1041-D11 to ED-B (Kd=6.9 nM). This is confirmed with respect to the other target molecules MIA-2, TNFalpha, NGF and IgG by the results depicted in FIGS. 14, 15, 16 and 17, respectively. Thus, only a few modifications (up to 8 substitutions in each monomer) in the ubiquitin-wildtype result with affinities to given targets in the low micromolar range.

Example 2B

Binding Analysis of Modified Ubiquitin-Based Binding Variants by Competitive Concentration Dependent ELISA The binding analysis is described here for the target ED-B but without further experimentation, it can be used for any other target. Competitive concentration dependent ELISAs analyzed the binding of ubiquitin variant 1041-D11 to immobilized ED-B containing fibronectin fragment (67B89) in the presence of increasing amounts of free target. Conditions of the ELISA were as described for Example 2A, except that 1041-D11 protein was preincubated with ED-B (67B89) (0 μM-10 μM) or also with negative control 6789 (0 μM-10 μM) for 1 h and subsequently the mixture was given to the target 67B89 that was placed on a Medisorp-plate; following this, the variant was detected by the corresponding antibody (anti-Ubiquitin-Fab-POD; dilution 1:6500).

FIG. 7 shows that variant 1041-D11 has a very high affinity binding to ED-B (IC50=140 nM). The result shown in FIG. 6 is confirmed; only a few modifications (up to 8 substitutions in each monomer) in the ubiquitin-wildtype result in a very higher affinity binding to ED-B.

Example 2C

Binding Analysis of Modified Ubiquitin-Based ED-B Binding Variants by Concentration Dependent ELISA Simultaneously Analyzing the Serum-Stability of Binding Activity The ELISA is performed using procedures well known in the art and as described above (Example 2A and 2B). ED-B (here referred to as 67B89) is coated to microtiter plates, the variant is bound to ED-B and detected by a specific ubiquitin-antibody (Anti-Ubi-Fab-POD). The variant in this assay is treated in different ways: the variant is incubated in mouse serum for 1 h at 37° C. (see in FIG. 9, circles in blue); the variant is incubated in rat serum for 1 h at 37° C. (in FIG. 13X, circles in red); or the variant is incubated PBS for 1 h at 37° C. (in FIG. 9, circles in black). FIG. 13 shows that all Kds of variant 1041-D11 are between 10.3 nM (in PBS) to 20.74 nM (in mouse-serum).

Example 2D

Binding Analysis of Modified Ubiquitin-Based ED-B Binding Variants by Biacore Assays Different concentrations of the variant were analyzed (for example, 0-200 nM of the variant, preferably 1041-D11) for binding to an ED-B containing fibronectin fragment (referred to as 67B89) immobilized on a CM5-chip (Biacore) using methods known to those skilled in the art. The obtained data were processed via the BIA evaluation software and 1:1-Langmuir-fitting. The $K_D$ of variant 1041-D11 was 1.0 nM, as shown in FIG. 8. The kinetic binding constants were $k_{on}$=7.6*10$^5$ M$^{-1}$ s$^{-1}$; $k_{off}$=7.7*10$^{-4}$ s$^{-1}$. The $K_D$ of the fusion protein 1041-D11-TNFalpha was 1.13 nM. The kinetic binding constants were $k_{on}$=4.5*10$^5$ M$^{-1}$s$^{-1}$; $k_{off}$=5.0*10$^{-4}$ s$^{-1}$.

Example 2E

Complex-Formation Analysis of Modified Ubiquitin-Based ED-B Binding Variants by SE-HPLC For the analysis of complex formation, Tricorn Superdex 75 5/150 GL columns (GE-Healthcare) (V=3 ml) were used and a protein amount of 50 μl was applied. Further conditions: buffer: 1×PBS, pH 7.3, flow-rate: 0.3 ml/min, run: 45 min (injection of sample: after 15 min). Condition: 0.72 nmol 1041-D11 protein+0.72 nmol ED-B (herein referred to 67B89) or as negative control fibronectin (herein referred to as 6789) incubated for 1 h at RT; then applied to column for analysis of complex-formation. In FIG. 14, only the variant is shown in black, only the target ED-B is shown in blue, the variant binding building a complex with ED-B in pink. FIG. 10 A shows ED-B containing fibronectin (67B89) with the variant; FIG. 10 B is the variant with ED-B-free fibronectin (6789). The figure shows that variant 1041-D11 builds a complex together with ED-B (67B89), but it builds no complex with fibronectin (6789) confirming the specificity.

Example 3

Ubiquitin-Based Hetero-Dimeric Binding Proteins with Improved Binding to TNF-Alpha Ubiquitin-based hetero-dimeric binding proteins specific for TNF-alpha were selected according to the method of the present invention, i.e. a phage library was established which included a population of modified hetero-dimeric ubiquitin binding proteins which were screened on their binding potential with TNF-alpha. The following modifications were performed:

In the first monomer: in one or more amino acids in positions 2, 4, 6, 62-66, optionally additionally in one or more of the positions 68, 70, 72-74, optionally additional positions.

In the second monomer: modifications in one or more amino acids in positions 6, 8, 62-66

As linker, SGGGGSGGGGIG was used in most cases, except for 1144-D11 (SEQ ID NO: 79) and 1144-E9 (SEQ ID NO: 80). No linker was used for 1144-D11 and 1144-E9 between the first and the second ubiquitin monomer. Positions 75 and 76 are either AA or GG. The linker is shown in part A of FIG. 15. The binding affinities are shown in FIG. 15 B-E.

Example 4

Generation of Ubiquitin-Based Hetero-Dimeric Binding Proteins with Improved Binding to MIA2

MIA2 is a diagnostic and therapeutic marker, inter alia in the context of cirrhosis, fibrosis and cancer of the liver. Detailed information on this marker can be found in US2004076965.

Target protein for the modified ubiquitin binding proteins of the invention is the stable 101 amino acid core region of MIA-2, referred to herein as SPR30-3. SPR30-3 is the structured portion of MIA-2. It is homologous to MIA (CD-RAP), OTOR, TANGO excluding the signal peptide. Its molecular weight is 11569,198 Da.

The amino acid core region of MIA-2 is as follows (SEQ ID NO: 95):

```
MLESTKLLADLKKCGDLECEALINRVSAMRDYRGPDCRYLNFTKGEEI

SVYVKLAGEREDLWAGSKGKEFGYFPRDAVQIEEVFISEEIQMSTKES

DFLCL
```

Ubiquitin-based hetero-dimeric binding proteins specific for MIA2 were selected according to the method of the present invention, i.e. a phage library was established which included a population of modified hetero-dimeric ubiquitin binding proteins which were screened on their binding potential with MIA2. The results are as follows:

FIG. 13 shows the alignment of ubiquitin-based hetero-dimeric MIA2 binding proteins.

Variant 1111-E10 shows affinity in the micromolar range on biotinylated target and complex formation in size exclusion chromatography. The most potent binder is designated 1111-E10 with amino acid substitutions in positions 6, 8, 62, 63, 64, 65, 66 in the first monomeric ubiquitin unit (BDR1) and different substitutions in positions 6, 8, 62, 63, 64, 65, 66 in the second monomeric ubiquitin unit (BDR2).

The first monomeric ubiquitin unit (BDR1) shows the same substitutions as in 1111-H2 and 1111-H12. Variants 1111-H2 and 1111-H12 can, therefore, be seen as a combination of BDR1 and BDR2 differing only by one substituted amino acid.

The following further potent binding molecules have been evaluated: 1111-C9, 1111-B4 and 1111-F6. These binders were either insoluble or did not show any binding to SPR30-3 of MIA2 in ELISA and on SEC. The variants 1111-E10 and 1111-C9, respectively and 1111-B4 were enriched (the additional substitution T9A in 1111-B4 occurred several times). 1111-F6 was not enriched but seemed to be an interesting candidate due to its high signal in a Hit-ELISA; this binder appeared, however, to be insoluble.

FIG. 14 shows a concentration-dependent ELISA with the binding variant 1111-E10 to biotinylated MIA-2 (biot. MIA2), Kd=2.6 microMolar (closed circles); control HSA (open circles). This variant 1111-E10 has been proven as the best binding molecule to MIA2. The sequence is as follows:

```
                                      (SEQ ID NO: 53)
MQIFVETFTGKTITLEVEPSDTIENVKAKIQDKEGIPPDQQRLIWAGK

QLEDGRTLSDYNIGWHPELHLVLRLRGGGIGMQIFVRTETGKTITLEV

EPSDTIENVKAKIQDKEGIPPDQQRLIWAGKQLEDGRTLSDYNILMGY

VLHLVLRLRAA
```

The linkers used are attached in the attached sequence listing as:

| | | |
|---|---|---|
| 1111-B4_21231 | sggggsggggig | SEQ ID NO: 96 |
| 1111-C9_21265 | sggggsggggig | SEQ ID NO: 96 |
| 1111-E10_21315 | gig | |
| 1111-F6_21331 | gig | |
| 1111-H12_21391 | eig[KHa4] | |
| 1111-H2_21371 | gig | |

-continued

PUBLICATIONS

1. Birchler, M., F. Viti, L. Zardi, B. Spiess, and D. Neri. 1999. Selective targeting and photocoagulation of ocular angiogenesis mediated by a phage-derived human antibody fragment. Nat Biotechnol 17:984-8.
2. Brenmoehl, J., M. Lang, M. Hausmann, S, N. Leeb, W. Falk, J. Scholmerich, M. Goke, and G. Rogler. 2007. Evidence for a differential expression of fibronectin splice forms ED-A and ED-B in Crohn's disease (CD) mucosa. Int J Colorectal Dis 22:611-23.
3. Dubin, D., J. H. Peters, L. F. Brown, B. Logan, K. C. Kent, B. Berse, S. Berven, B. Cercek, B. G. Sharifi, R. E. Pratt, and et al. 1995. Balloon catheterization induced arterial expression of embryonic fibronectins. Arterioscler Thromb Vasc Biol 15:1958-67.
4. Goodsell, D. S. 2001. FUNDAMENTALS OF CANCER MEDICINE: The Molecular Perspective: Antibodies. The Oncologist 6:547-548.
5. Kaczmarek, J., P. Castellani, G. Nicolo, B. Spina, G. Allemanni, and L. Zardi. 1994. Distribution of oncofetal fibronectin isoforms in normal, hyperplastic and neoplastic human breast tissues. Int J Cancer 59:11-6.
6. Menrad, A., and H. D. Menssen. 2005. ED-B fibronectin as a target for antibody-based cancer treatments. Expert Opin Ther Targets 9:491-500.
7. Pujuguet, P., A. Hammann, M. Moutet, J. L. Samuel, F. Martin, and M. Martin. 1996. Expression of fibronectin ED-A+ and ED-B+ isoforms by human and experimental colorectal cancer. Contribution of cancer cells and tumor-associated myofibroblasts. Am J Pathol 148:579-92.
8. Trachsel, E., M. Kaspar, F. Bootz, M. Detmar, and D. Neri. 2007. A human mAb specific to oncofetal fibronectin selectively targets chronic skin inflammation in vivo. J Invest Dermatol 127:881-6.
9. Van Vliet, A., H. J. Baelde, L. J. Vleming, E. de Heer, and J. A. Bruijn. 2001. Distribution of fibronectin isoforms in human renal disease. J Pathol 193:256-62.
10. Lipovsek, D., and Pluckthun, A. (2004). In-vitro protein evolution by ribosome display and mRNA display. J. Immunol. Methods 290, 51-67.
11. Ohashi, H., Shimizu, Y., Ying, B. W., and Ueda, T. (2007). Efficient protein selection based on ribosome display system with purified components. Biochem Biophys. Res. Commun 352, 270-276.
12. Studier, F. W. (2005). Protein production by auto-induction in high density shaking cultures. Protein Expr Purif 41, 207-234.
13. Zahnd, C., Amstutz, P., and Plückthun, A. (2007). Ribosome display: selecting and evolving proteins in vitro that specifically bind to a target. Nat. Methods 4, 269-279.
14. Paschke, M. and W. Hohne (2005). Gene 350(1): 79-88
15. Brüser 2007 Appl Microbiol Biotechnol 76(1): 35-45

The invention claimed is:

1. A method for identifying a hetero-multimeric modified ubiquitin with binding capability to a ligand with a binding affinity, with respect to the ligand, that did not exist previously, comprising the following steps:

a) providing a population of hetero-multimeric modified ubiquitin originating from monomeric modified ubiquitin proteins, said population comprising hetero-multimeric proteins comprising two or more ubiquitin monomers linked together in a head-to-tail arrangement wherein at least one of said monomers of said hetero-multimeric protein is differently modified at least by substitutions of surface exposed amino acids in at least three amino acids located in positions 2, 4, 6, 8, 62, 63, 64, 65, 66, and 68 of SEQ ID NO: 1, said modified monomeric protein having an amino acid sequence identity of at least 80%, at least 90%, or at least 95% to the unmodified ubiquitin protein;

b) providing a potential ligand to said population of differently modified proteins;

c) contacting said population of differently modified proteins with said ligand;

d) identifying a hetero-multimeric modified protein by a screening process, wherein said modified hetero-multimeric protein binds to said ligand with a specific binding affinity of Kd in a range of $10^{-7}$-$10^{-12}$ M and exhibits a monovalent binding activity with respect to said ligand; and optionally e) isolating said hetero-multimeric modified ubiquitin with said binding affinity, wherein a hetero-multimeric modified ubiquitin that binds to a ligand with a binding affinity, with respect to the ligand, that did not exist previously is identified.

2. The method of claim 1, wherein said hetero-multimeric protein is a hetero-dimeric or hetero-trimeric protein.

3. The method of claim 1, wherein said modified monomeric protein further comprises one or more insertions of 1 to 10 amino acids and/or one or more deletions of 1 to 7 amino acids as compared to SEQ ID NO: 1, further optionally wherein said modified monomeric ubiquitin protein comprises at least 6 and at most 14 substitutions of amino acids as compared to SEQ ID NO: 1, and further wherein as compared to SEQ ID NO: 1, said modified hetero-dimeric ubiquitin protein comprises:

(i) at least 12 and at most 28 substitutions; and/or (ii) at least 1 and at most 20 insertions; and/or (iii) at least 1 and at most 14 deletions.

4. The method of claim 1, wherein said modified monomeric ubiquitin protein is obtained by genetically engineering of DNA encoding for ubiquitin, and expressing of said protein in prokaryotic or eukaryotic organisms or in vitro.

5. The method of claim 1, wherein said screening process is a display method, optionally selected from the group consisting of a phage display method, a ribosomal display method, a TAT phage display method, a yeast display method, a bacterial display method, a cell surface display method, or an mRNA display method.

6. The method of claim 1, wherein said ligand is an antigen or hapten.

7. The method of claim 1, wherein a further 1 to 7 additional amino acids are substituted in at least one of the monomeric ubiquitin proteins, which further 1 to 7 additional amino acids are optionally selected from one or more of the amino acids in positions 36, 44, 70, 71, and optionally additionally 62, 63, and 64 or 72 and 73 or 8 of SEQ ID NO: 1.

8. The method of claim 1, wherein said population of hetero-multimeric fusion proteins of ubiquitin is provided by genetically fusing two DNA libraries each encoding differently modified monomeric proteins, translating the DNA into hetero-multimeric fusion proteins, displaying said proteins and screening the displayed proteins for the presence of modified hetero-multimeric ubiquitin proteins comprising monomeric ubiquitin proteins being linked together in a head-to-tail arrangement wherein said modified hetero-multimeric ubiquitin proteins bind to said ligand with a specific binding affinity of Kd in a range of $10^{-7}$-$10^{-12}$ M and exhibit a monovalent binding activity with respect to said ligand or wherein said population of hetero-multimeric fusion proteins of ubiquitin is provided by chemical synthesis of the proteins.

9. A DNA library containing DNA encoding for a population of hetero-multimeric ubiquitin fusion proteins originating from monomeric ubiquitins, each multimeric protein comprising two or more modified ubiquitin monomers linked together in a head-to-tail arrangement, wherein:

(i) at least two of each of said monomers of said multimeric protein are differently modified at least by substitutions of surface exposed amino acids in at least three amino acids located in positions 2, 4, 6, 8, 62, 63, 64, 65, 66, and 68 of SEQ ID NO: 1;

(ii) the multimeric protein binds to a ligand with a binding affinity, with respect to the ligand, that did not exist previously; and (iii) said modified monomeric protein having has an amino acid sequence identity of at least 80%, at least 90%, or at least 95% to SEQ ID NO: 1.

10. A protein library obtained by expression of the DNA library of claim 9.

11. A prokaryotic or eukaryotic cell or a population of phages containing the DNA or protein library according to claim 9 or 10.

12. A polynucleotide encoding for a fusion protein of said protein library of claim 10.

13. A vector comprising a polynucleotide according to claim 12.

* * * * *